United States Patent
Bassett et al.

(10) Patent No.: US 11,008,297 B2
(45) Date of Patent: May 18, 2021

(54) BIO-BASED, MULTI-AROMATIC COMPOUNDS, AND METHODS OF MAKING AND USING SAME

(71) Applicants: ROWAN UNIVERSITY, Glassboro, NJ (US); The United States of America as represented by the Secretary of the Army, Washington, DC (US)

(72) Inventors: Alexander W. Bassett, Mullica Hill, NJ (US); Joseph F. Stanzione, III, Wilmington, DE (US); John J. La Scala, Wilmington, DE (US); Joshua M. Sadler, Middle River, MD (US); Owen M. Stecca, Middletown, DE (US)

(73) Assignees: Rowan University, Glassboro, NJ (US); The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 16/613,857

(22) PCT Filed: May 15, 2018

(86) PCT No.: PCT/US2018/032656
§ 371 (c)(1),
(2) Date: Nov. 15, 2019

(87) PCT Pub. No.: WO2018/213236
PCT Pub. Date: Nov. 22, 2018

(65) Prior Publication Data
US 2020/0199087 A1  Jun. 25, 2020

Related U.S. Application Data

(60) Provisional application No. 62/506,273, filed on May 15, 2017, provisional application No. 62/527,319, filed on Jun. 30, 2017.

(51) Int. Cl.
| | |
|---|---|
| *C07D 307/42* | (2006.01) |
| *C07D 407/14* | (2006.01) |
| *C07C 43/23* | (2006.01) |
| *C07C 69/54* | (2006.01) |

(52) U.S. Cl.
CPC ........... *C07D 307/42* (2013.01); *C07C 43/23* (2013.01); *C07C 69/54* (2013.01); *C07D 407/14* (2013.01)

(58) Field of Classification Search
CPC .... C07D 307/42; C07D 407/14; C07C 43/23; C07C 69/54

USPC .......................................................... 549/502
See application file for complete search history.

(56) References Cited

U.S. PATENT DOCUMENTS

| | | | |
|---|---|---|---|
| 4,024,106 A | * | 5/1977 | Mader ..................... C07C 45/46 524/338 |
| 4,778,936 A | | 10/1988 | Mizuno et al. |
| 5,032,487 A | * | 7/1991 | Ono ......................... G03C 8/08 430/218 |
| 6,537,546 B2 | | 3/2003 | Echigo et al. |
| 8,058,333 B1 | | 11/2011 | Chang et al. |
| 8,816,135 B2 | | 8/2014 | Yoshitomo et al. |
| 2005/0004406 A1 | | 1/2005 | Carvill et al. |
| 2005/0014086 A1 | | 1/2005 | Eswaran et al. |
| 2010/0274006 A1 | | 10/2010 | Amanokura et al. |
| 2012/0129963 A1 | | 5/2012 | Benedetti et al. |
| 2014/0186872 A1 | | 7/2014 | Feve et al. |
| 2014/0275435 A1 | | 9/2014 | Holmberg et al. |
| 2015/0370166 A1 | | 12/2015 | Takemura et al. |

FOREIGN PATENT DOCUMENTS

| | | | |
|---|---|---|---|
| CN | 103145568 | * | 6/2013 |
| JP | 2014189526 | * | 10/2014 |
| JP | 6097113 | * | 2/2017 |
| WO | 2015140818 A1 | | 9/2015 |
| WO | 2015183892 A1 | | 12/2015 |

OTHER PUBLICATIONS

Amorati et al., Journal of the chemical society, perkin Pranslations 2 (2001), (11), 2142-2146.*
Fache, et al., "Vanillin, a key-intermediate of biobased polymers", European Polymer Journal, vol. 68, Mar. 28, 2015, pp. 488-502.
Gopalakrishnan, et al., "Synthesis and Thermal Properties of Polyurethanes from Cardanol-furfural Resin", J Chem Pharma Res, vol. 2, No. 3, 2010, pp. 193-205.
Xu, et al., "Development of a Novel Spectrophotometric Method Based on Diazotization-Coupling Reaction for Detrminatino of Bisphenol A", J Brazilian Chem Soc, vol. 28, No. 8, Dec. 2016, pp. 1475-1482.

* cited by examiner

*Primary Examiner* — Niloofar Rahmani
(74) *Attorney, Agent, or Firm* — Saul Ewing Arnstein & Lehr LLP; Domingos J. Silva

(57) ABSTRACT

The present invention relates to the unexpected discovery of novel multi-aromatic, multi-substituted compounds. In certain embodiments, the compounds of the invention are generated by condensing at least two phenolic- and/or aniline-containing monomers and an aromatic, aliphatic or heteroaromatic aldehyde- and/or ketone-containing monomer. In other embodiments, at least one monomer is isolated from a bio-based resource. In yet other embodiments, the compounds of the invention are bis- or poly-phenolic compounds.

7 Claims, 7 Drawing Sheets

Where n equals 0, 2, 4, and/or 6 or mixtures thereof

BIO-BASED, MULTI-AROMATIC COMPOUNDS, AND METHODS OF MAKING AND USING SAME

CROSS-REFERENCE TO RELATED APPLICATIONS

The present application is a 35 U.S.C. § 371 national phase application of, and claims priority to, International Application No. PCT/US2018/032656, filed May 15, 2018, which claims priority under 35 U.S.C. § 119(e) to U.S. Provisional Application No. 62/506,273, filed May 15, 2017, and U.S. Provisional Application No. 62/527,319, filed Jun. 30, 2017, all of which are incorporated herein by reference in their entireties.

STATEMENT REGARDING FEDERALLY SPONSORED RESEARCH OR DEVELOPMENT

This invention was made with government support under grant numbers W911NF-14-2-0086 and W911NF-16-2-0225 awarded by the U.S. Army Research Laboratory, and grant number WP-2402 awarded by Strategic Environmental Research and Development Program (SERDP, U.S. Department of Defense). The government has certain rights in the invention.

BACKGROUND OF THE INVENTION

Intermolecular condensation is a chemical reaction whereby two or more distinct molecules react to form a larger molecule, along with loss of one or more small molecules. Common examples of such small molecules are water, acetic acid, hydrogen chloride, methanol, or ethanol. The reaction of two amino acids to form a dipeptide is a common example of an intermolecular condensation, which involves loss of water. Sequential intermolecular condensations involving polyfunctional monomers can give rise to overall polymerization of those monomers. Reactions useful for promoting intermolecular condensation include nucleophilic acyl substitution, aldol or Claisen-Schmidt condensation, Claisen condensation, Darzens reaction or glycidic ester condensation, Dieckmann condensation, Knoevenagel condensation, Pechmann condensation, Rap-Stoermer condensation, Thorpe reaction, and acyloin condensation.

Bisphenol A [4,4'-(propane-2,2-diyl)diphenol; also known as BPA] is an industrially useful chemical that can be generated through intermolecular condensation of phenol and acetone. BPA is often used as starting material to prepare plastics and epoxy resins. BPA-based plastic is clear and tough, and is made into a variety of consumer goods, such as water bottles, sports equipment, CDs and DVDs. Epoxy resins containing BPA are used to line water pipes, and as internal coatings for food and beverage cans. BPA is one of the most widely chemicals produced worldwide, with about 4 million tons of BPA being used yearly to manufacture polycarbonate plastic.

Unfortunately, BPA has estrogen mimicking, hormone-like properties, which can cause hormone disruption in those consumers exposed to this chemical. As a result, some countries have banned or limited the use of BPA-based products. For example, the European Union and Canada have banned the use of BPA in baby bottles, and public pressure in the U.S. has led to virtual termination of use of BPA in baby bottles and infant Formula packaging. Studies have suggested that BPA can accumulate in humans and can be associated with reproductive, neurological and developmental problems, as well as thyroid hormone disruption, obesity and metabolic disease.

In view of the increasing awareness of BPA liabilities, the chemical industry eagerly waits for an adequate and safe replacement for BPA in consumer products. In particular, there is great interest in developing novel materials using starting materials that are available in nature and or are byproducts of natural product processing. Such materials would address important aims of modern materials science: utilize natural resources that would otherwise be discarded, minimize use of petroleum-based starting materials, and develop products with novel and useful properties.

There is thus a need in the art for novel processes that allow for the generation of useful compounds from naturally available starting materials. Such compounds could find use in the chemical industry, for example as polymerization building blocks, coatings, dyes, and surfactants. The present invention fulfills these needs.

BRIEF SUMMARY OF THE INVENTION

The invention provides certain compounds, or a salt or solvate thereof. The invention further provides methods of making compounds of the invention, or salts or solvates thereof. The invention further provides methods of evaluating the pH of a system.

In certain embodiments, the compound of the invention is a compound of Formula (Ia), or a salt or solvate thereof:

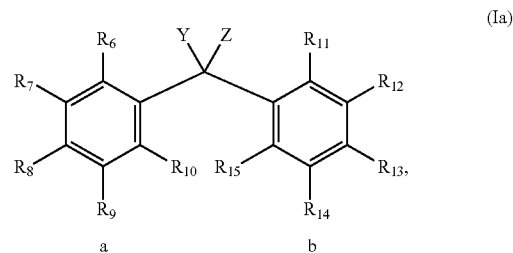

wherein in (Ia): Z is H; each one of $R_6$-$R_{15}$ is independently selected from the group consisting of H, —OH, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, wherein at least one selected from the group consisting of $R_6$-$R_{10}$ is —OH (or a protected version thereof), and wherein at least one selected from the group consisting of $R_{11}$-$R_{15}$ is —OH (or a protected version thereof); Y is

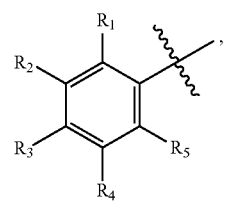

wherein each one of $R_1$-$R_5$ is independently selected from the group consisting of H, —OH, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl.

In certain embodiments, the compound of the invention is a compound of Formula (Ib), or a salt or solvate thereof:

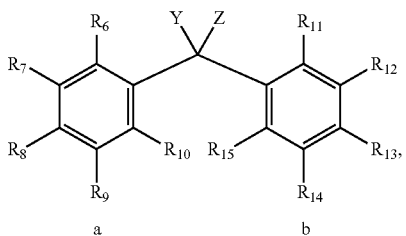

(Ib)

wherein in (Ib): Z is H; each one of $R_6$-$R_{15}$ is independently selected from the group consisting of H, —OH, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, wherein at least one selected from the group consisting of $R_6$-$R_{10}$ is —OH (or a protected version thereof), and wherein at least one selected from the group consisting of $R_{11}$-$R_{15}$ is —OH (or a protected version thereof); Y is selected from the group consisting of:

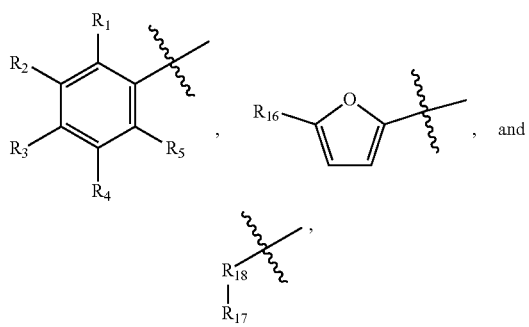

wherein: each one of $R_1$-$R_5$ and $R_{17}$ is independently selected from the group consisting of H, —OH, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, $R_{18}$ is a $C_1$-$C_6$ alkylene group, and $R_{16}$ is selected from the group consisting of H, —$CH_2OH$, —$CH_2O(C_1$-$C_6$ alkyl), —$CH_2$(halogen), —$CH_2NH_2$, $C_1$-$C_{20}$ alkyl, $C_1$-$C_6$ alkoxy, $C_1$-$C_6$ acyloxy, furyl, benzyl, substituted furyl, and substituted benzyl.

In certain embodiments, the compound of the invention is a compound of Formula (Ic), or a salt or solvate thereof:

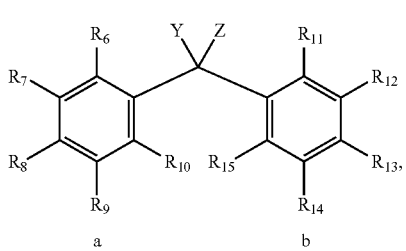

(Ic)

wherein in (Ic): Z is selected from the group consisting of —$CH_3$ and —$CH_2CH_3$; each one of $R_6$-$R_{15}$ is independently selected from the group consisting of H, —OH, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, wherein at least one selected from the group consisting of $R_6$-$R_{10}$ is —OH (or a protected version thereof), and wherein at least one selected from the group consisting of $R_{11}$-$R_{15}$ is —OH (or a protected version thereof); Y is selected from the group consisting of:

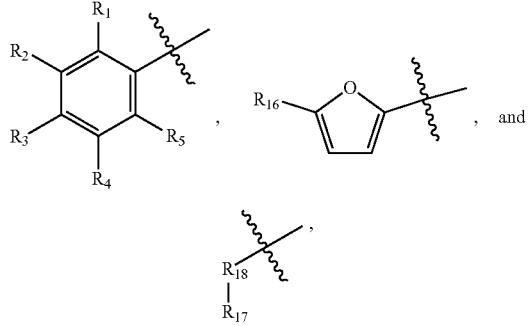

wherein: each one of $R_1$-$R_5$ and $R_{17}$ is independently selected from the group consisting of H, —OH, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, $R_{18}$ is a $C_1$-$C_6$ alkylene group, and $R_{16}$ is selected from the group consisting of H, —$CH_2OH$, —$CH_2O(C_1$-$C_6$ alkyl), —$CH_2$(halogen), —$CH_2NH_2$, $C_1$-$C_{20}$ alkyl, $C_1$-$C_6$ alkoxy, $C_1$-$C_6$ acyloxy, furyl, benzyl, substituted furyl, and substituted benzyl.

In certain embodiments, the compound of the invention is a compound of Formula (Id), or a salt or solvate thereof:

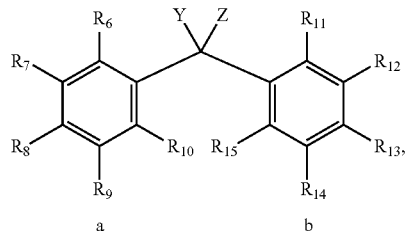

(Id)

wherein in (Id): Z is selected from the group consisting of H, —$CH_3$ and —$CH_2CH_3$; each one of $R_6$-$R_{15}$ is independently selected from the group consisting of H, —OH, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, wherein at least one selected from the group consisting of $R_6$-$R_{10}$ is —$NH_2$ (or a protected version thereof), and wherein at least one selected from the group consisting of $R_{11}$-$R_{15}$ is —$NH_2$ (or a protected version thereof); Y is selected from the group consisting of:

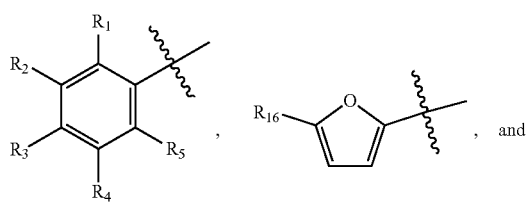

-continued

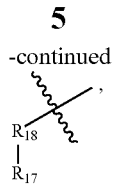

wherein: each one of $R_1$-$R_5$ and $R_{17}$ is independently selected from the group consisting of H, —OH, $C_1$-$C_{20}$ alkyl, $C_1$-$C_6$ alkoxy, $C_1$-$C_6$ acyloxy, halogen, —NH$_2$, furyl, benzyl, substituted furyl, and substituted benzyl, $R_{18}$ is a $C_1$-$C_6$ alkylene group, and $R_{16}$ is selected from the group consisting of H, —CH$_2$OH, —CH$_2$O($C_1$-$C_6$ alkyl), —CH$_2$(halogen), —CH$_2$NH$_2$, $C_1$-$C_{20}$ alkyl, $C_1$-$C_6$ alkoxy, $C_1$-$C_6$ acyloxy, furyl, benzyl, substituted furyl, and substituted benzyl.

In certain embodiments, the compound of the invention is a compound of Formula (Ie), or a salt or solvate thereof:

(Ie)

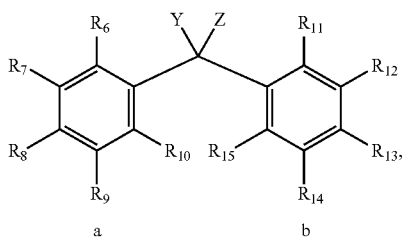

wherein in (Ie): Z is H; each one of $R_6$-$R_{15}$ is independently selected from the group consisting of H, —OH, $C_1$-$C_{20}$ alkyl, $C_1$-$C_6$ alkoxy, $C_1$-$C_6$ acyloxy, —NH$_2$, furyl, benzyl, substituted furyl, and substituted benzyl, wherein rings a and b are independently substituted with at least one electron donating group and no strong electron withdrawing groups and (Ie) has greater electron donating character than the corresponding unsubstituted analogue of (Ie); wherein at least one selected from the group consisting of $R_6$-$R_{10}$ is —OH or —NH$_2$ (or a protected version thereof), and wherein at least one selected from the group consisting of $R_{11}$-$R_{15}$ is —OH or —NH$_2$ (or a protected version thereof); Y is selected from the group consisting of:

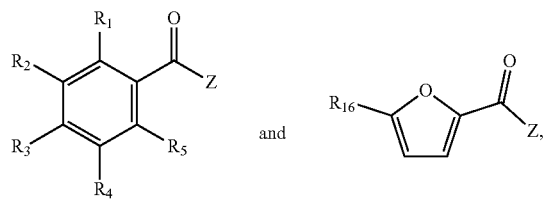

wherein: each one of $R_1$-$R_5$ is independently selected from the group consisting of H, —OH, $C_1$-$C_{20}$ alkyl, $C_1$-$C_6$ alkoxy, $C_1$-$C_6$ acyloxy, —NH$_2$, furyl, benzyl, substituted furyl, and substituted benzyl, wherein at least one of $R_1$-$R_5$ is electron donating group and none of $R_1$-$R_5$ is strongly electron withdrawing, and $R_{16}$ is selected from the group consisting of H, —CH$_2$OH, —CH$_2$O($C_1$-$C_6$ alkyl), —CH$_2$(halogen), —CH$_2$NH$_2$, $C_1$-$C_{20}$ alkyl, $C_1$-$C_6$ alkoxy, $C_1$-$C_6$ acyloxy, furyl, benzyl, substituted furyl, and substituted benzyl.

In certain embodiments, the compound of the invention is a compound of Formula (IIa), or a salt or solvate thereof:

(IIa)

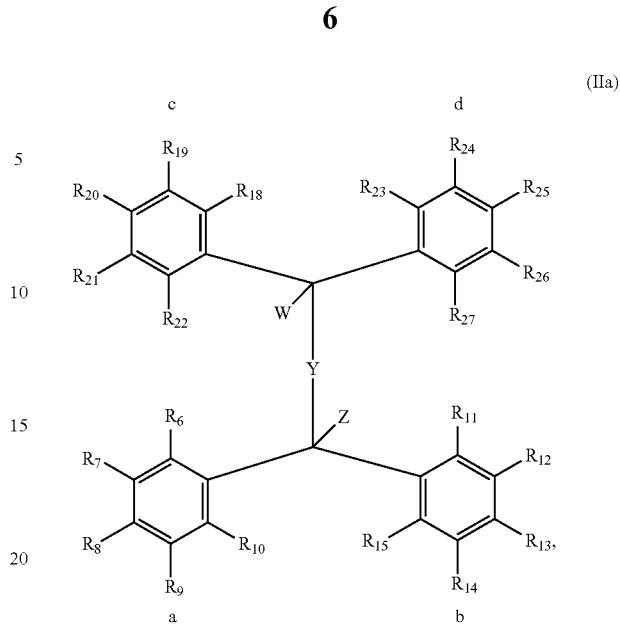

wherein in (IIa): Z and W are independently selected from the group consisting of H, —CH$_3$, and —CH$_2$CH$_3$; each one of $R_6$-$R_{15}$ and $R_{18}$-$R_{27}$ is independently selected from the group consisting of H, —OH, $C_1$-$C_{20}$ alkyl, $C_1$-$C_6$ alkoxy, $C_1$-$C_6$ acyloxy, halogen, —NH$_2$, furyl, benzyl, substituted furyl, and substituted benzyl, wherein at least one selected from the group consisting of $R_6$-$R_{10}$ is —OH or —NH$_2$ (or a protected version thereof), wherein at least one selected from the group consisting of $R_{11}$-$R_{15}$ is —OH or —NH$_2$ (or a protected version thereof), wherein at least one selected from the group consisting of $R_{18}$-$R_{22}$ is —OH or —NH$_2$ (or a protected version thereof), and wherein at least one selected from the group consisting of $R_{23}$-$R_{27}$ is —OH or —NH$_2$ (or a protected version thereof); Y is selected from the group consisting of:

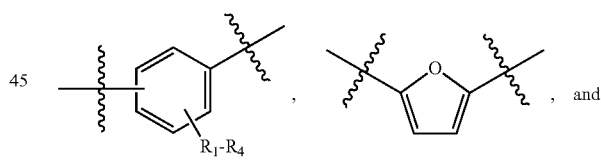, and

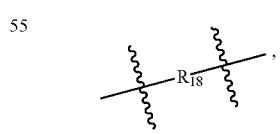

wherein: each one of $R_1$-$R_4$ is independently selected from the group consisting of H, $C_1$-$C_{20}$ alkyl, $C_1$-$C_6$ alkoxy, $C_1$-$C_6$ acyloxy, halogen, furyl, benzyl, substituted furyl, and substituted benzyl, and $R_{18}$ is a $C_1$-$C_6$ alkylene group.

In certain embodiments, the compound of the invention is a compound of Formula (IIb), or a salt or solvate thereof:

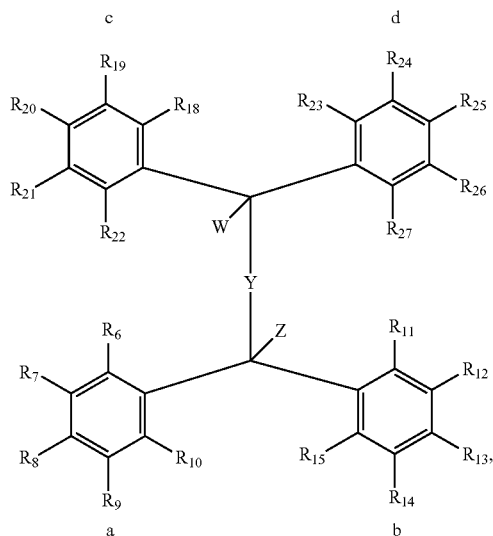

(IIb)

wherein in (IIb): Z and W are both H; each one of $R_6$-$R_{15}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, —$NH_2$, furyl, benzyl, substituted furyl, and substituted benzyl, wherein rings a and b are independently substituted with at least one electron donating group and no strong electron withdrawing groups and (IIb) has greater electron donating character than the corresponding unsubstituted analogue of (IIb); wherein at least one selected from the group consisting of $R_6$-$R_{10}$ is —OH or —$NH_2$ (or a protected version thereof), and wherein at least one selected from the group consisting of $R_{11}$-$R_{15}$ is —OH or —$NH_2$ (or a protected version thereof); Y is selected from the group consisting of

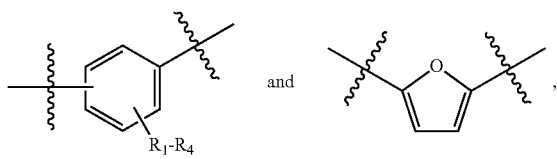

and wherein: each one of $R_1$-$R_4$ is independently selected from the group consisting of H, $C_1$-$C_{20}$ alkyl (in certain embodiments, $C_1$-$C_6$ alkyl), $C_1$-$C_6$ alkoxy, $C_1$-$C_6$ acyloxy, furyl, benzyl, substituted furyl, and substituted benzyl, wherein at least one of $R_1$-$R_4$ is electron donating group and none of $R_1$-$R_4$ is strongly electron withdrawing.

In certain embodiments, the compound of the invention is a compound of Formula (V), or a salt or solvate thereof:

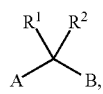

(V)

wherein in (V): $R^1$ and $R^2$ are independently selected from the group consisting of H and $C_1$-$C_{12}$ alkyl, or $R^1$ and $R^2$ combine to form =O; ring A is selected from the group consisting of:

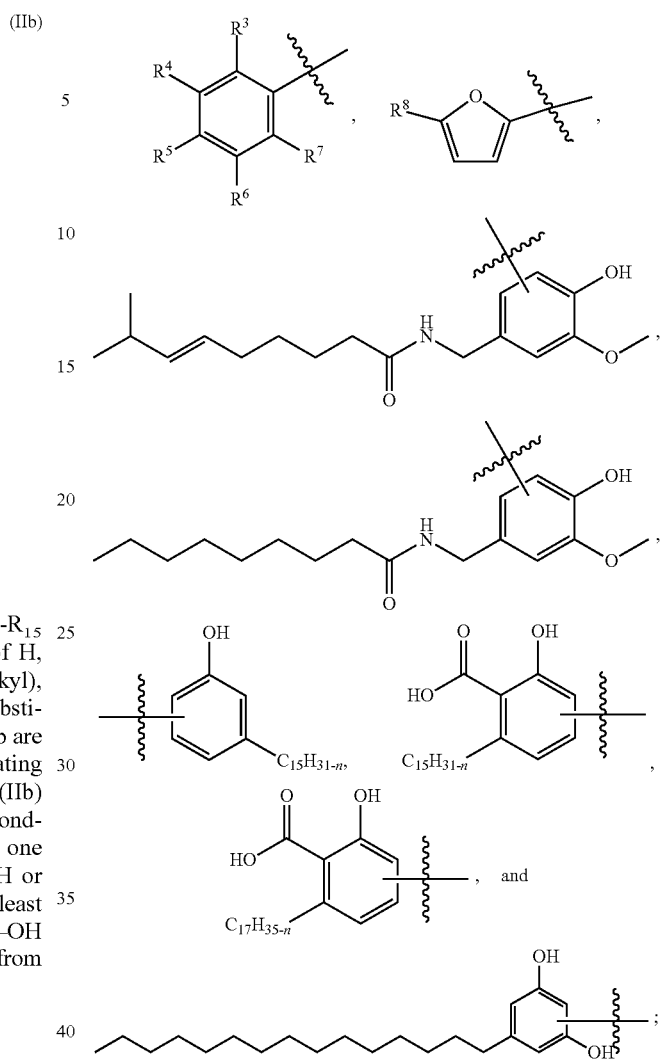

ring B is selected from the group consisting of:

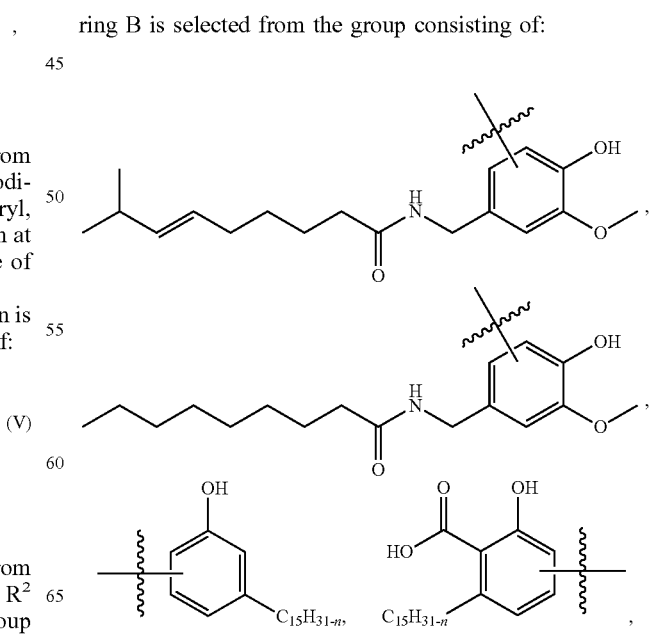

-continued

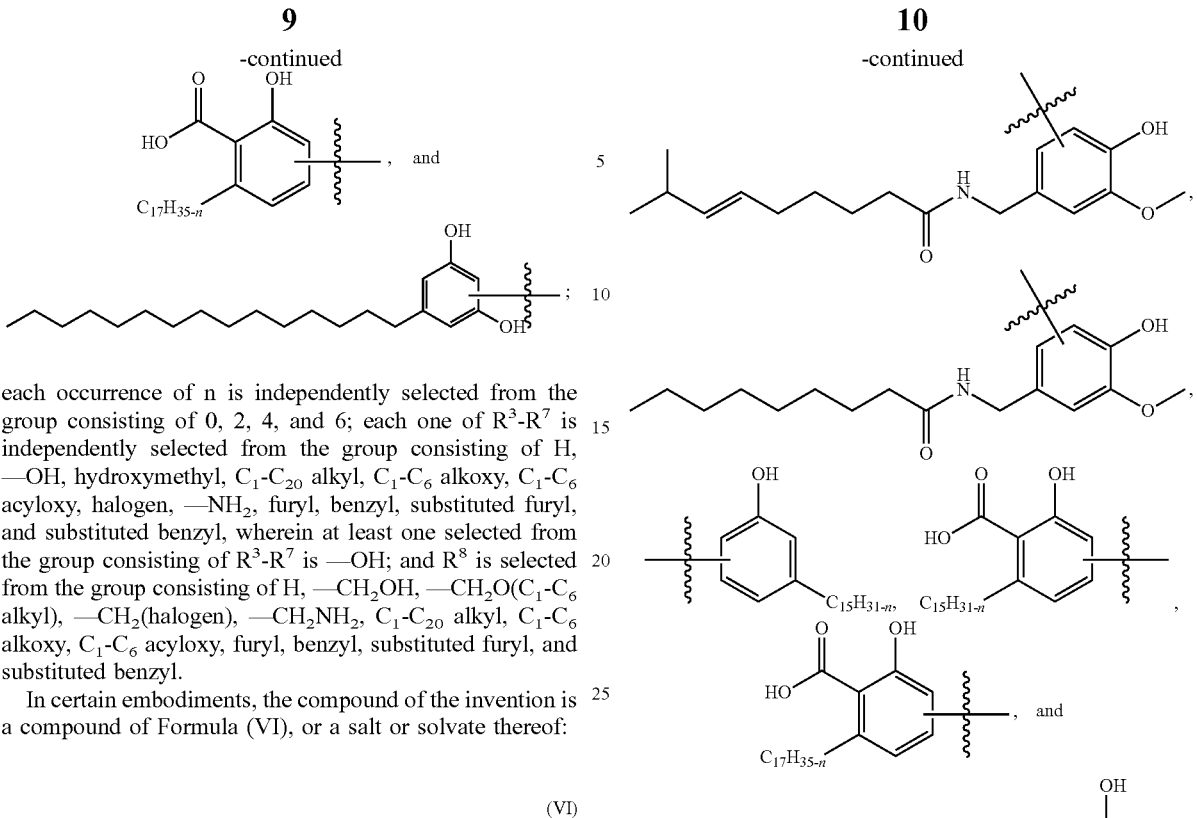

each occurrence of n is independently selected from the group consisting of 0, 2, 4, and 6; each one of $R^3$-$R^7$ is independently selected from the group consisting of H, —OH, hydroxymethyl, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, wherein at least one selected from the group consisting of $R^3$-$R^7$ is —OH; and $R^8$ is selected from the group consisting of H, —$CH_2OH$, —$CH_2O(C_1$-$C_6$ alkyl), —$CH_2$(halogen), —$CH_2NH_2$, $C_1$-$C_{20}$ alkyl, $C_1$-$C_6$ alkoxy, $C_1$-$C_6$ acyloxy, furyl, benzyl, substituted furyl, and substituted benzyl.

In certain embodiments, the compound of the invention is a compound of Formula (VI), or a salt or solvate thereof:

(VI)

wherein in (VI): m is 1 or 2, wherein if m is equal to 2, then each

unit is covalently linked to another

unit through a —C($R^1$)($R^2$)— bond; n is 0, 1, or 2; X is A or B; each occurrence of $R^1$ and $R^2$ are independently selected from the group consisting of H and $C_1$-$C_{12}$ alkyl, or $R^1$ and $R^2$ bound to the same carbon combine to form =O; each ring A is independently selected from the group consisting of:

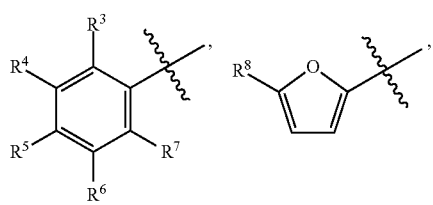

each ring B is independently selected from the group consisting of:

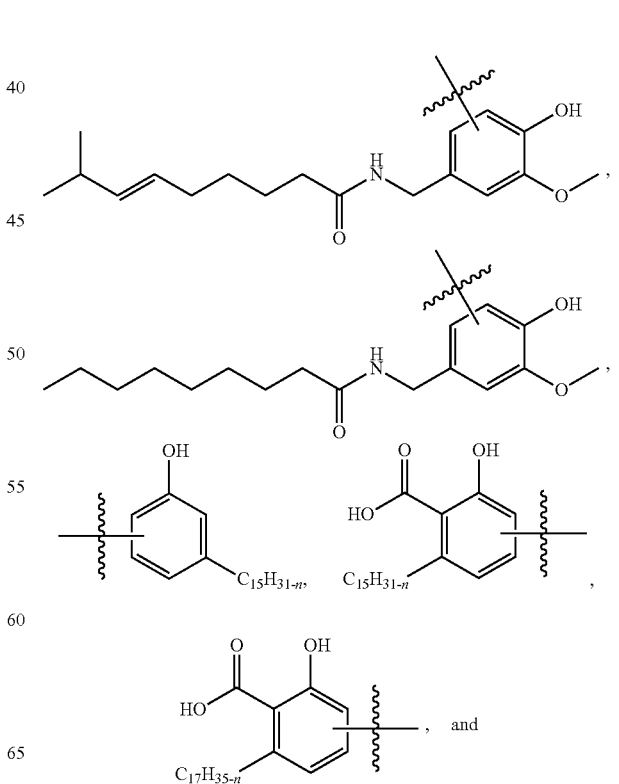

-continued

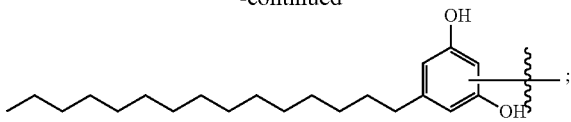

each occurrence of n is independently selected from the group consisting of 0, 2, 4, and 6; each one of $R^3$-$R^7$ is independently selected from the group consisting of H, —OH, hydroxymethyl, $C_1$-$C_{20}$ alkyl, $C_1$-$C_6$ alkoxy, $C_1$-$C_6$ acyloxy, halogen, —$NH_2$, furyl, benzyl, substituted furyl, and substituted benzyl, wherein at least one selected from the group consisting of $R^3$-$R^7$ is —OH; and $R^8$ is selected from the group consisting of H, —$CH_2OH$, —$CH_2O(C_1$-$C_6$ alkyl), —$CH_2$(halogen), —$CH_2NH_2$, $C_1$-$C_{20}$ alkyl, $C_1$-$C_6$ alkoxy, $C_1$-$C_6$ acyloxy, furyl, benzyl, substituted furyl, and substituted benzyl.

In certain embodiments, in (Ia), (Ib), (Ic), (Id), (Ie), (IIa) or (IIb) at least one of $R_{1-5}$ is not H. In other embodiments, in (Ia), (Ib), (Ic), (Id), (Ie), (IIa) or (IIb) at least one of $R_1$-$R_5$ is OH. In yet other embodiments, in (Ia), (Ib), (Ic), (Id), (Ie), (IIa) or (IIb) at least one of $R_1$-$R_5$ is $C_1$-$C_6$ alkoxy. In yet other embodiments, in (Ia), (Ib), (Ic), (Id), or (Ie) at least one of $R_1$-$R_5$, $R_6$-$R_{10}$, and $R_{11}$-$R_{15}$ is $C_1$-$C_{20}$ aliphatic hydrocarbyl. In yet other embodiments, in (Ia), (Ib), (Ic), (Id), or (Ie) at least one of $R_1$-$R_5$, $R_6$-$R_{10}$, and $R_{11}$-$R_{15}$ is $C_{31-n}$, wherein n is 0, 2, 4 or 6. In yet other embodiments, in (IIa) or (IIb) at least one of $R_1$-$R_5$, $R_6$-$R_{10}$, $R_{11}$-$R_{15}$, $R_{18}$-$R_{22}$, and $R_{23}$-$R_{27}$ is $C_1$-$C_{20}$ aliphatic hydrocarbyl. In yet other embodiments, in (IIa) or (IIb) at least one of $R_1$-$R_5$, $R_6$-$R_{10}$, $R_{11}$-$R_{15}$, $R_{18}$-$R_{22}$, and $R_{23}$-$R_{27}$ is $C_{15}H_{31-n}$, wherein n is 0, 2, 4 or 6. In yet other embodiments, in (Ia), (Ib), (Ic), (Id), or (Ie) rings a and b are identical. In yet other embodiments, in (IIa) or (IIb) rings a and b are identical, and rings c and d are identical. In yet other embodiments, in (IIa) or (IIb) rings a, b, c, and d are identical.

In certain embodiments, in (Ia), (Ib), (Ic), (Id), or (Ie) Y is 4-hydroxy-3-methoxy-phenyl, 4-methacryloxy-3-methoxy-phenyl, 3,4-dihydroxy-6-methyl-phenyl, or 3,5-dimethoxy-4-hydroxy-phenyl. In other embodiments, in (IIa) or (IIb) Y and Z are independently selected from the group consisting of 2-furyl, 4-hydroxy-3-methoxy-phenyl, 4-methacryloxy-3-methoxy-phenyl, 3,4-dihydroxy-6-methyl-phenyl, and 3,5-dimethoxy-4-hydroxy-phenyl. In yet other embodiments, in (Ia), (Ib), (Ic), (Id), or (Ie) ring a and ring b are independently selected from the group consisting of 4-hydroxy-3-methoxy-phenyl, 4-methacryloxy-3-methoxy-phenyl, 3,4-dihydroxy-6-methyl-phenyl, and 3,5-dimethoxy-4-hydroxy-phenyl. In yet other embodiments, in (Ia), (Ib), (Ic), (Id), or (Ie) ring a and ring b are identical and are selected from the group consisting of 4-hydroxy-3-methoxy-phenyl, 4-methacryloxy-3-methoxy-phenyl, 3,4-dihydroxy-6-methyl-phenyl, and 3,5-dimethoxy-4-hydroxy-phenyl. In yet other embodiments, in (IIa) or (IIb) rings a-d are independently selected from the group consisting of 4-hydroxy-3-methoxy-phenyl, 4-methacryloxy-3-methoxy-phenyl, 3,4-dihydroxy-6-methyl-phenyl, and 3,5-dimethoxy-4-hydroxy-phenyl. In yet other embodiments, in (IIa) or (IIb) rings a-d are identical and selected from the group consisting of 4-hydroxy-3-methoxy-phenyl, 4-methacryloxy-3-methoxy-phenyl, 3,4-dihydroxy-6-methyl-phenyl, and 3,5-dimethoxy-4-hydroxy-phenyl.

In certain embodiments, the compound is a compound of Formula (III), or a salt or solvate thereof:

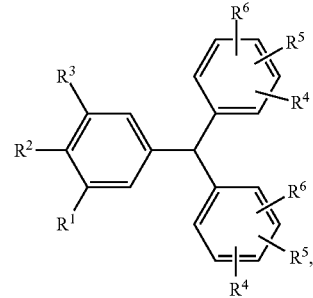

wherein in (III): $R^1$, $R^2$ and $R^3$ are independently selected from the group consisting of H, OH, $C_1$-$C_{20}$ aliphatic hydrocarbyl, $C_1$-$C_6$ alkoxy, and $C_1$-$C_6$ acyloxy; each occurrence of $R^4$ is independently OH or $C_1$-$C_6$ alkoxy; each occurrence of $R^5$ and $R^6$ is independently selected from the group consisting of H, OH, $C_1$-$C_{20}$ aliphatic hydrocarbyl, $C_1$-$C_6$ alkoxy, and $C_1$-$C_6$ acyloxy; with the proviso that for each ring at least one selected from the group consisting of $R^5$ and $R^6$ is not H.

In certain embodiments, the compound is a compound of Formula (IV), or a salt or solvate thereof:

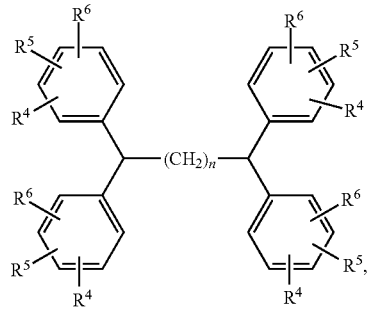

wherein in (IV): n ranges from 0 to 10, wherein each $CH_2$ group is independently optionally substituted with one or two $C_1$-$C_6$ alkyl groups; each occurrence of $R^4$ is independently OH or $C_1$-$C_6$ alkoxy; each occurrence of $R^5$ and $R^6$ is independently selected from the group consisting of H, OH, $C_1$-$C_{20}$ aliphatic hydrocarbyl, $C_1$-$C_6$ alkoxy, and $C_1$-$C_6$ acyloxy; with the proviso that for each ring at least one selected from the group consisting of $R^5$ and $R^6$ is not H.

In certain embodiments, at least one phenolic or aniline group is derivatized with an epoxy group. In other embodiments, the compound is cured into a polymer. In yet other embodiments, at least one phenolic or aniline group is derivatized with a (meth)acrylate or (meth)acrylic group. In yet other embodiments, the compound is cured into a polymer. In yet other embodiments, at least one phenolic hydroxyl group or aniline amino group forms a urethane group. In yet other embodiments, at least one phenolic hydroxyl group forms a carbonate group. In yet other embodiments, at least one phenolic hydroxyl group forms an allyl ester, or wherein at least one aniline amine forms an allyl amide. In yet other embodiments, the compound is cured into a polymer.

In certain embodiments, the compound is (Ie) or (IIb) and has a pH-dependent ultraviolet-visible spectrum.

In certain embodiments, at least one ring from the group selected from rings a-d is
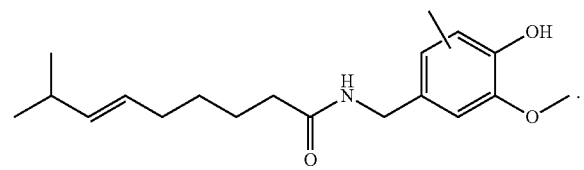
In other embodiments, at least one ring from the group selected from rings a-d is
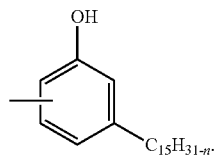
In yet other embodiments, at least one of $R_6$-$R_{15}$ is methoxy or acyloxy.
In certain embodiments, the compound is at least one selected from the group consisting of:
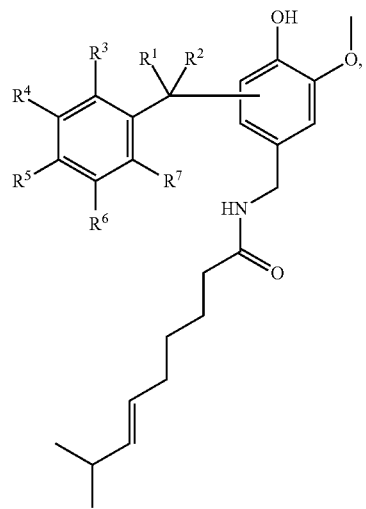
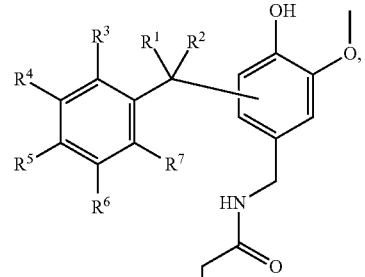
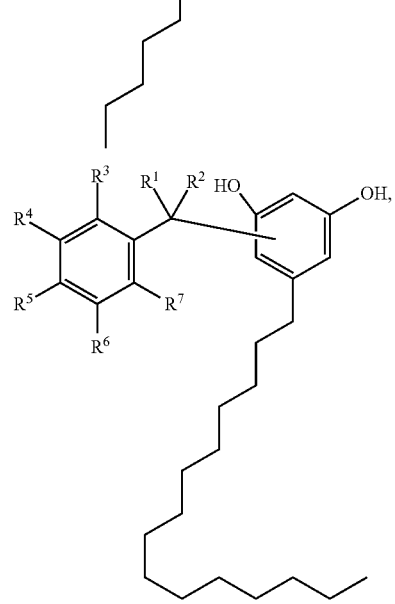
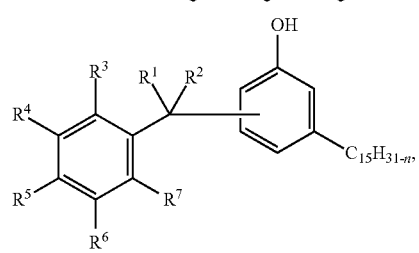
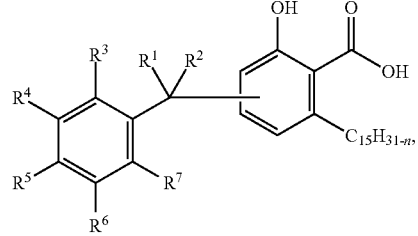
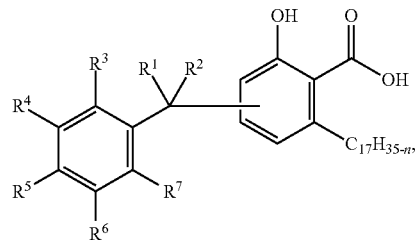

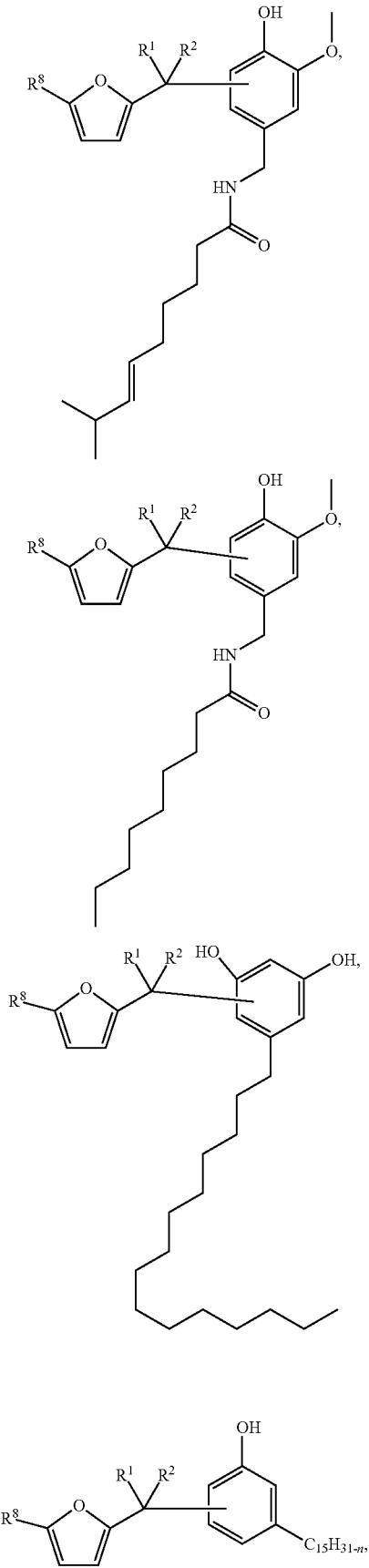

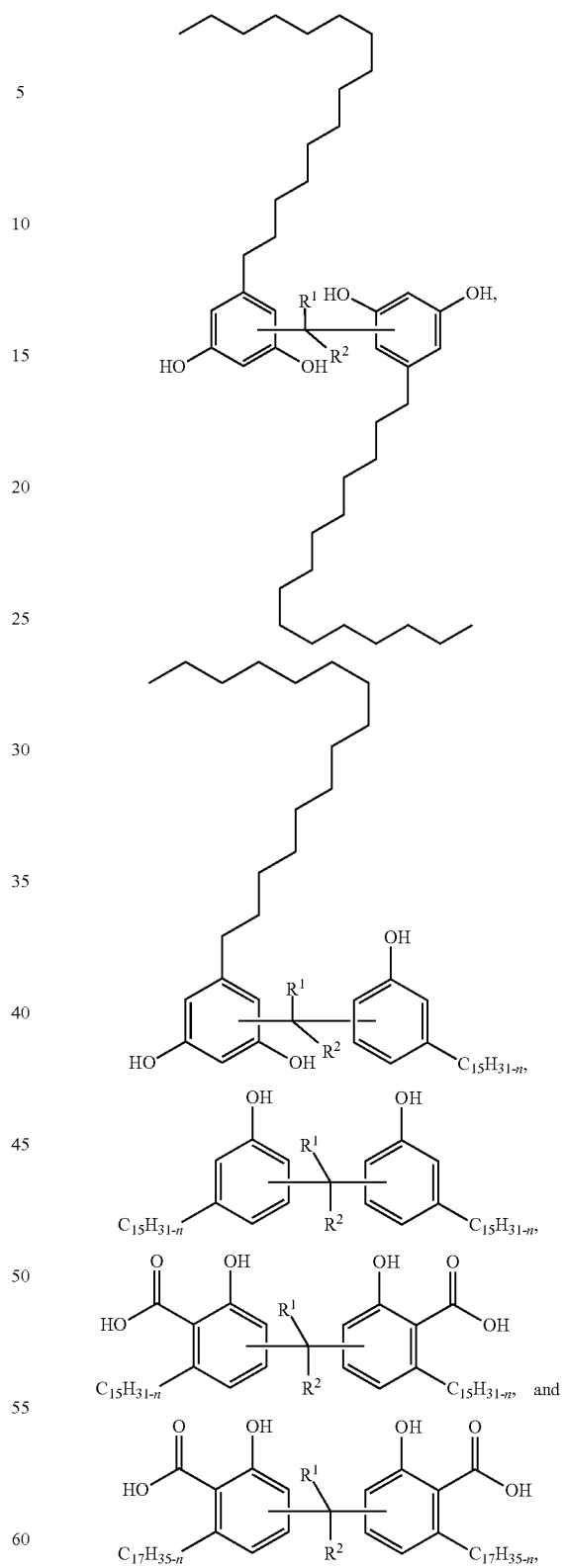
or a derivative, salt or solvate thereof.
In certain embodiments, ring A is derived from the starting material:

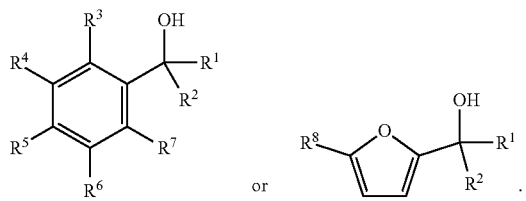
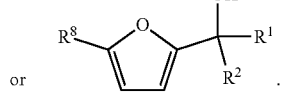

or

In other embodiments, at least one occurrence of $R^3$-$R^7$ is H. In yet other embodiments, at least two occurrences of $R^3$-$R^7$ are H. In yet other embodiments, at least three occurrences of $R^3$-$R^7$ are H. In yet other embodiments, at least four occurrences of $R^3$-$R^7$ are H. In yet other embodiments, $R^1$ and $R^2$ are H. In yet other embodiments, $R^1$ and $R^2$ are methyl. In yet other embodiments, $R^1$ is H and $R^2$ is methyl. In yet other embodiments, $R^1$ and $R^2$ combine so as to form =O.

In certain embodiments, in (VI) m=1, n=1, X=A, and the compound comprises a structure selected from the group consisting of:

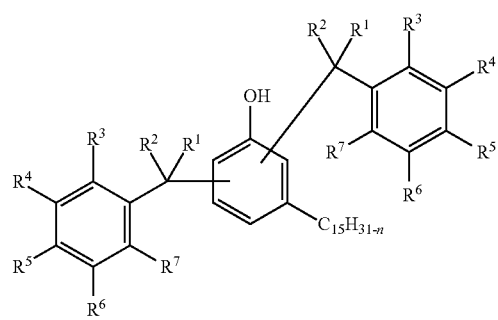

and

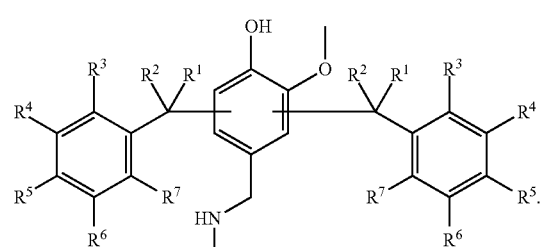

In certain embodiments, in (VI) m=1, n=1, X=A, and the compound comprises a structure selected from the group consisting of:

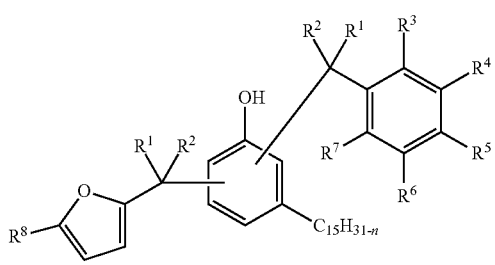

and

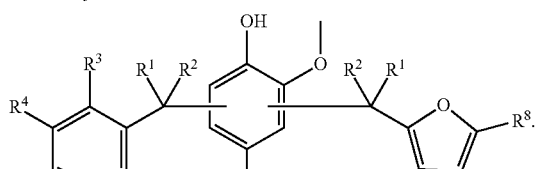

In certain embodiments, the method of preparing the compound of Formula (Ia), (Ib), (Ic), (Id) or (Ie) comprises contacting: the starting materials of Formula one starting material selected from the group consisting of for (Ib), (Ic), (Id) or (Ie); and is

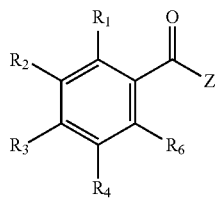

for (Ia); and an acid; wherein Z is H for (Ia), (Ib) or (Ie), Z is $CH_3$ and $-CH_2CH_3$ for (Ic), and Z is H, $CH_3$ and $-CH_2CH_3$ for (Id).

In certain embodiments, the method of preparing the compound of Formula (IIa) or (IIb) comprises contacting: the starting materials of Formula

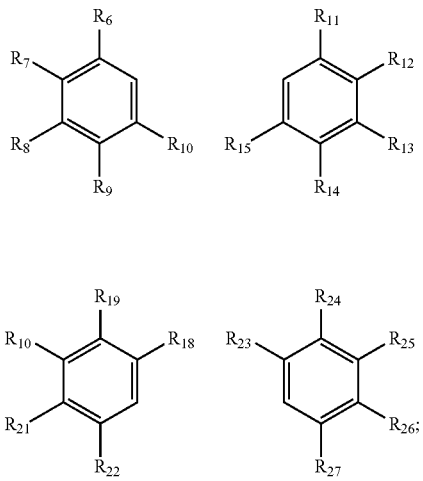

an acid; and at least one starting material selected from the group consisting of:

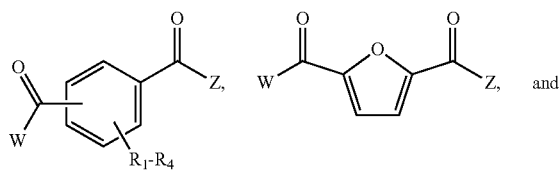

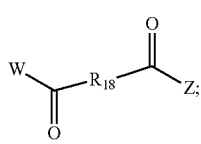

wherein Z is selected from the group consisting of H, $-CH_3$ and $-CH_2CH_3$.

In certain embodiments, the method of preparing a compound of Formula (V) comprises contacting: at least one compound selected from the group consisting of:

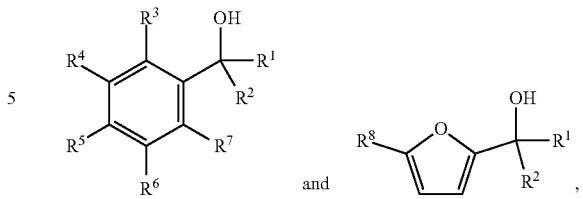

wherein at least one selected from the group consisting of $R^3$-$R^7$ is —OH, at least one selected from the group consisting of cardanol, cardol, anacardic acid, synthetic capsaicin, and capsaicin, or any salt, solvate or derivative thereof; and an acid catalyst.

In certain embodiments, the method of preparing a compound of Formula (V) comprises contacting: at least two compounds independently selected from the group consisting of cardanol, cardol, anacardic acid, synthetic capsaicin, and capsaicin, or any salt, solvate or derivative thereof; at least one selected from the group consisting of an aldehyde and ketone; and an acid catalyst.

In certain embodiments, the method of preparing a compound of Formula (VI) comprises contacting at least two compounds of Formula (V); an aldehyde or ketone; and an acid catalyst. In other embodiments, the method of preparing a compound of Formula (VI) comprises contacting a compound of Formula (V); at least one selected from the group consisting of cardanol, cardol, anacardic acid, synthetic capsaicin, and capsaicin, or any salt, solvate or derivative thereof; an aldehyde or ketone; and an acid catalyst. In yet other embodiments, the method of preparing a compound of Formula (VI) comprises contacting a compound of Formula (V); at least one phenolic-containing compound or any salt, solvate or derivative thereof; an aldehyde or ketone; and an acid catalyst. In yet other embodiments, the method of preparing a compound of Formula (VI) comprises contacting a compound of Formula (V); at least one compound selected from the group consisting of:

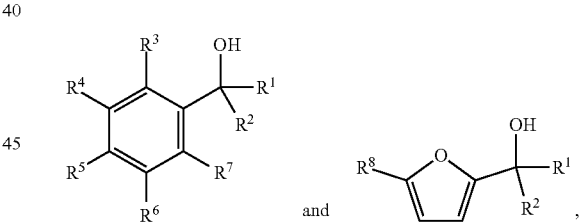

wherein at least one selected from the group consisting of $R^3$-$R^7$ is —OH; and an acid catalyst.

In certain embodiments, at least one starting material is independently isolated from a bio-based resource. In other embodiments, the starting materials are independently isolated from bio-based resources.

In certain embodiments, the method of evaluating the pH of a system contacting a compound of Formula (Ie) or (IIb), with the system and evaluating the ultraviolet visible (UV-vis) spectrum of the compound.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
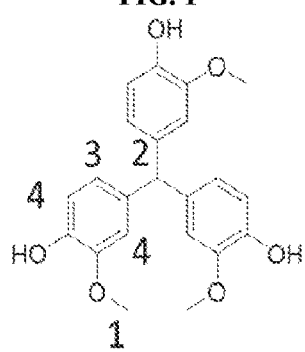
FIG. 1 illustrates a non-limiting tri-aromatic compound of the invention, 4,4',4"-methanetriyltris(2-methoxyphenol), which can be prepared by condensing vanillin and guaiacol (2-methoxyphenol). Also illustrated is the $^1$H NMR spectrum of the tri-aromatic compound in DMSO-$d_6$.
Figure 2:
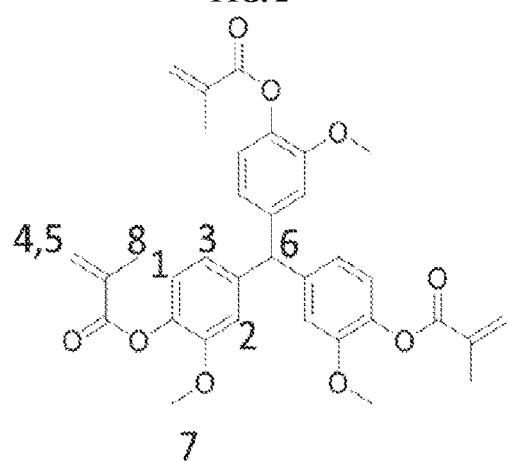
FIG. 2 illustrates a non-limiting tri-aromatic compound of the invention, 4,4',4"-methanetriyl-tris(2-methoxybenzene-4,1-diyl) 1,1',1"-tris(2-methylacrylate), which can be prepared by condensing two molecules of guaiacol with vanillin, and then converting the three phenolic groups to the corresponding (meth)acrylate esters. Also illustrated is the $^1$H NMR spectrum of the tri-aromatic compound in DMSO-$d_6$.
Figure 2:
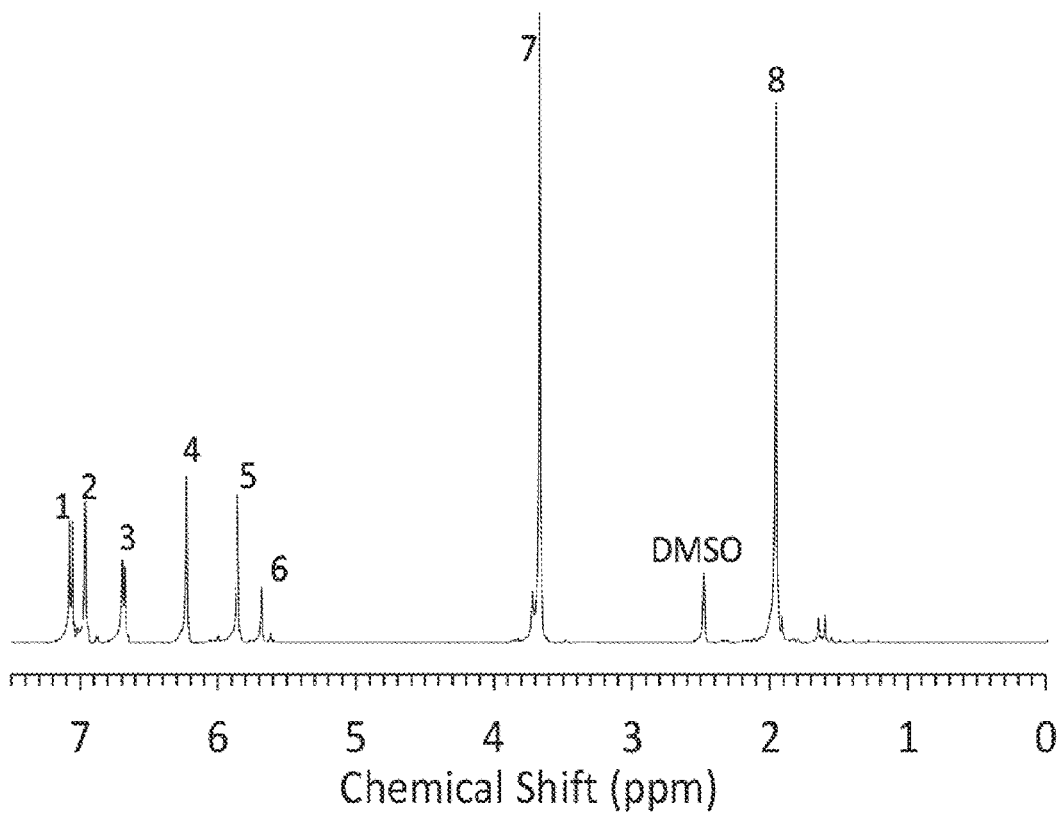
Figure 3:
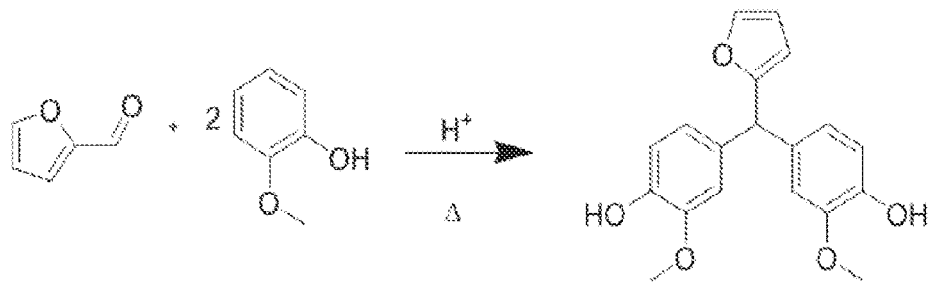
FIG. 3 illustrates a non-limiting tri-aromatic compound of the invention, 4,4'-(furan-2-ylmethylene)bis(2-methoxyphenol), which can be prepared by condensing furfural and guaiacol (2-methoxyphenol).
Figure 4:
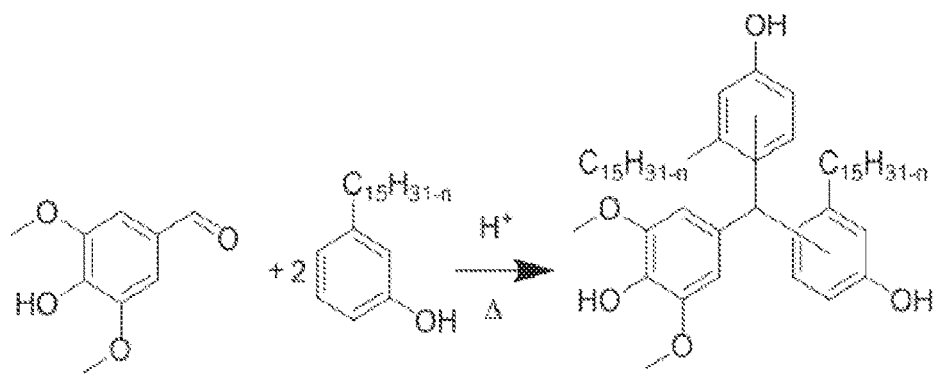
FIG. 4 illustrates a non-limiting reaction that allows for preparation of illustrative compounds of the invention.
Figure 5:
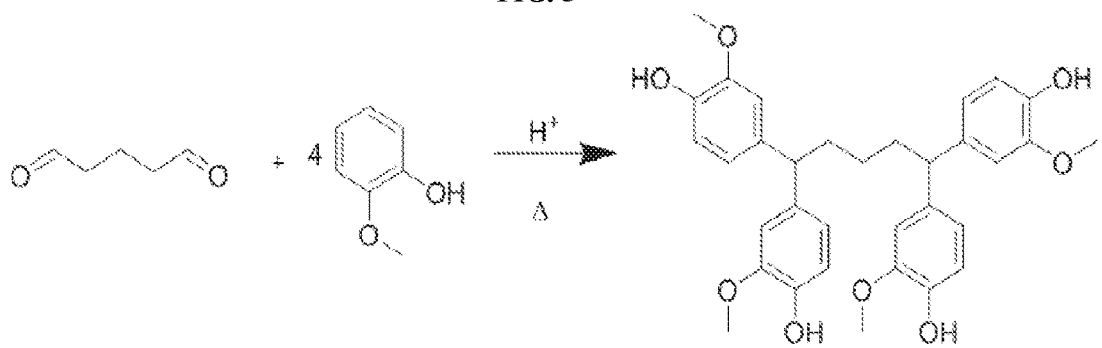
FIG. 5 illustrates a non-limiting tetra-aromatic compound of the invention, 4,4',4",4"'-(pentane-1,1,5,5-tetrayl)tetrakis(2-methoxyphenol), which can be prepared by condensing glutaraldehyde and guaiacol.
Figure 6:
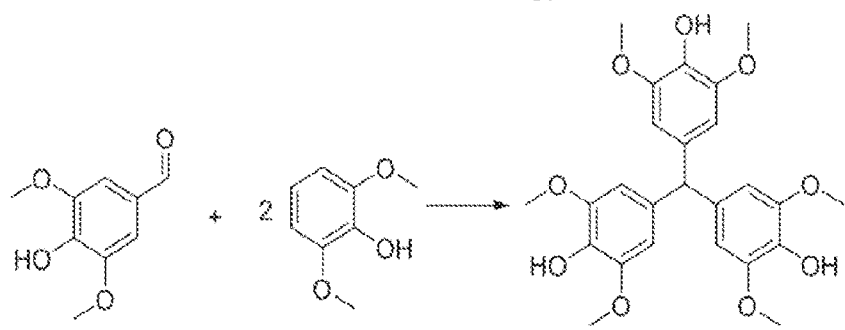
FIG. 6 illustrates a non-limiting tri-aromatic compound of the invention, 4,4',4"-methanetriyltris(2,6-dimethoxyphenol), which can be prepared by condensing syringol (1,3-dimethoxy-2-hydroxy-benzene) and syringaldehyde (4-hydroxy-3,5-dimethoxy benzaldehyde).

The present invention relates to the unexpected discovery of novel multi-aromatic, multi-substituted compounds. In certain embodiments, the compounds of the invention are generated by condensing at least two phenolic-containing/aniline-containing monomers and an aromatic, aliphatic or heteroaromatic aldehyde-/ketone-containing monomer (which can be a mono-aldehyde, polyaldehyde, mono-ketone, poly-ketone, and any combinations thereof). In other embodiments, the compounds of the invention are multi-aromatic, bis- or poly-phenolic compounds.

In certain embodiments, at least one of the monomers is synthetically prepared. In other embodiments, at least one of the monomers is derived from bio-based resources, such as, but not limited to, tannin (which comprises aromatic aldehydes and aldehydes, and phenols), lignin (which comprises aromatic aldehydes and aldehydes, and phenols), cashew nutshell liquid (which comprises cardanol), capsaicin, cellulose, hemicellulose (which comprises furan-based aldehydes and ketones), plant oils (which comprise aliphatic aldehydes and ketones), terpenes, animal fats, herbs, spices, chitin, chitosan, and/or aquatic biomass. In other embodiments, the compounds of the invention are useful in chemical or biotechnological applications. In yet other embodiments, the compounds of the invention are further modified so as to generate other chemically useful compounds, such as, but not limited to, polymers, coatings, resins, composites, and/or dyes. In yet other embodiments, the compounds of the invention (or derivatives thereof) are generated by condensing a phenolic or furan monomer with a phenolic monomer derived from natural sources. In yet other embodiments, the phenolic monomer is derived from cashew nutshell liquid, herbs, spices, and tannins.

In certain embodiments, the compounds of the invention have reduced toxicity as compared to other compounds used within the art, such as but not limited to BPA. In other embodiments, the compounds of the invention have anti-fouling properties. In other embodiments, the compounds of the invention have anti-inflammatory, anti-bacterial and/or anti-fungal properties. In yet other embodiments, the compounds of the invention are further modified so as to generate other chemically useful compounds, such as, but not limited to, polymers and/or dyes.

In certain embodiments, the compounds of the invention form polymeric materials that have increased toughness as compared to other compounds used within the art. In yet other embodiments, the compounds of the invention form polymeric materials with increased rigidity as compared to other compounds used within the art. In yet other embodiments, the compounds of the invention form polymeric materials with increased flexibility and/or toughness as compared to other compounds used within the art. In yet other embodiments, the compounds of the invention form polymeric materials with reduced water permeability and/or absorption as compared to other compounds used within the art. In yet other embodiments, the compounds of the invention form polymeric materials with increased bio-carbon content as compared to other compounds used within the art. In yet other embodiments, the compounds of the invention form polymeric materials that are capable of self-healing. In yet other embodiments, the compounds of the invention form polymeric materials with increased glass transition temperature ($T_g$) as compared to other compounds used within the art. In yet other embodiments, the compounds of the invention have low melting points, such that, for example, they are in liquid form at about room temperature, thereby improving their processability for liquid polymer manufacturing processes and stereolithography additive manufacturing. In yet other embodiments, the compounds of the invention have reduced toxic effects in a subject as compared to compounds used within the art. In yet other embodiments, the compounds of the invention cause reduced endocrine disruption as compared to compounds used within the art.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "anacardic acid" refers to a phenolic lipid found in the shell of the cashew nut (*Anacardium occidentale*). Chemically, anacardic acid is a mixture of several closely related organic compounds, each consisting of a salicylic acid substituted with a saturated or unsaturated alkyl chain that has 15 or 17 carbon atoms:

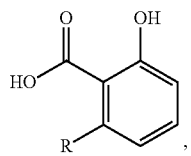

wherein R=$C_{15}H_{31-n}$ or $C_{17}H_{35-n}$, wherein n is independently 0, 2, 4, or 6. The term "anacardic acid" also applies to derivatives thereof, including derivatives of the (poly) alkenyl chain if present, such as partially or fully hydrogenated derivatives, partially or fully epoxidized derivatives, partially or fully hydroxylated derivatives, and/or partially or fully metathesized derivatives thereof.

As used herein, the term "bisphenol A" or "BPA" refers to 4,4'-(propane-2,2-diyl) diphenol, also known as p,p'-isopropylidenebisphenol, or 2,2-bis(4-hydroxyphenyl)propane.

As used herein, the term "capsaicin" refers to 8-methyl-N-vanillyl-6-nonenamide, or a salt or solvate thereof:

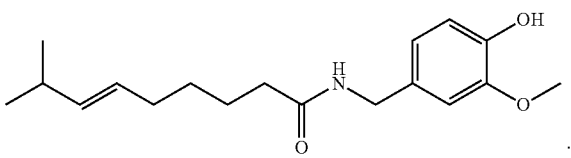 [SMILES: COc1cc(CNC(=O)CCCC/C=C/C(C)C)ccc1O]

The term "capsaicin" also applies to derivatives thereof, including derivatives of the alkenyl chain, such as hydrogenated derivatives, epoxidized derivatives, hydroxylated derivatives, and/or metathesized derivatives thereof.

As used herein, the term "cardanol" refers to a phenolic lipid obtained from anacardic acid, the main component of cashew nutshell liquid (CNSL), which is a byproduct of cashew nut processing. Cardanol has the Formula shown below, wherein each of the double bonds is independently optionally reduced:

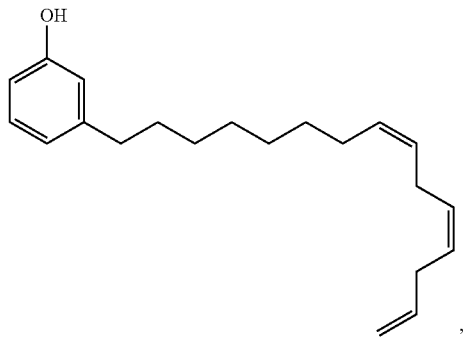 [SMILES: C=CC/C=C\C/C=C\CCCCCCCc1cccc(O)c1]

and thus can be also represented as

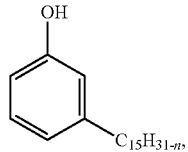

wherein n is 0, 2, 4 or 6. Only a fraction of the cardanol obtained from cashew nut processing is currently used in the industrial field. The term "cardanol" also applies to derivatives thereof, including derivatives of the (poly)alkenyl chain if present, such as partially or fully hydrogenated derivatives, partially or fully epoxidized derivatives, partially or fully hydroxylated derivatives, and/or partially or fully metathesized derivatives thereof.

As used herein, the term "cardol" or "adipostatin A" refers to 5-pentadecylbenzene-1,3-diol, which is an alkylresorcinol (a type of phenolic lipids composed of long aliphatic chains and phenolic rings) that is similar in structure to urushiol (the irritant found in poison ivy). Cardol can be found in *Gingko biloba* fruits and *Streptomyces cyaneus*. Cardol is also found in cashew nutshell liquid (*Anacardium occidentale*), in *Anacardium othonianum* and in *Ardisia elliptica*:

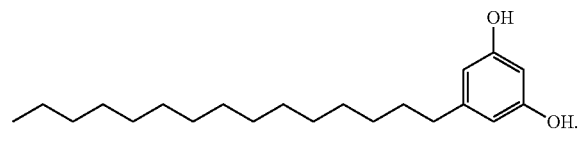 [SMILES: CCCCCCCCCCCCCCCc1cc(O)cc(O)c1]

The term "cardol" also applies to analogues wherein the alkyl chain is modified with at least one unsaturation (double bond), including derivatives thereof, including partially or fully hydrogenated derivatives, partially or fully epoxidized derivatives, partially or fully hydroxylated derivatives, and/or partially or fully metathesized derivatives thereof.

As used herein, the term "curable" as applied to a material refers to a material comprising at least one functional group that can undergo polymerization. The curable material can be non-polymerized (i.e., non-cured material), or can be submitted to polymerization conditions (such as chemical reagents or physical conditions) that induce polymerization of at least a fraction of the at least one polymerizable functional group (i.e., partially or fully cured material). In certain embodiments, polymerization or crosslinking of the curable material results in about 100% consumption of the at least one functional group (i.e., fully cured). In other embodiments, polymerization or crosslinking of the curable material results in less than about 100% consumption of the at least one functional group (i.e., partially cured).

As used herein, the term "instructional material" includes a publication, a recording, a diagram, or any other medium of expression that can be used to communicate the usefulness of the compositions and methods of the invention. In some instances, the instructional material can be part of a kit useful for preparing a compound of the invention. The instructional material of the kit may, for example, be affixed to a container that contains the compositions of the invention or be shipped together with a container that contains the compositions. Alternatively, the instructional material can be shipped separately from the container with the intention that the recipient uses the instructional material and the compositions cooperatively. For example, the instructional material is for use of a kit; or instructions for use of a compound or composition of the invention.

The term "monomer" refers to any discreet chemical compound of any molecular weight.

As used herein, the term "polymer" refers to a molecule composed of repeating structural units typically connected by covalent chemical bonds. The term "polymer" is also meant to include the terms copolymer and oligomers. In certain embodiments, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction can consume between about 0% and about 100% of the at least one functional group available in the system. In certain embodiments, polymerization or crosslinking of at least one functional group results in about 100% consumption of the at least one functional group. In other embodiments, polymerization or crosslinking of at least one functional group results in less than about 100% consumption of the at least one functional group.

As defined herein, the term "protected" as applied to a phenol or aniline refers a derivative of the phenolic hydroxyl or the anilinic amino group, such as but not limited to an alkyl derivative (e.g., ether for the phenol, and N-alkyl-aniline or N-alkyl-N-alkyl-aniline for the aniline), an acyl derivative (e.g., ester for the phenol, or amide for the aniline), and so forth, as known to those in the art. In certain embodiments, the protected derivative can be deprotected to the respective phenol or aniline using methods known in the art. In other embodiments, the protected derivative can be used as such within the methods of the invention.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "synthetic capsaicin," also known as nonivamide, pelargonic acid vanillylamide or PAVA, refers to N-[(4-Hydroxy-3-methoxyphenyl)methyl]nonanamide, or a salt or solvate thereof:

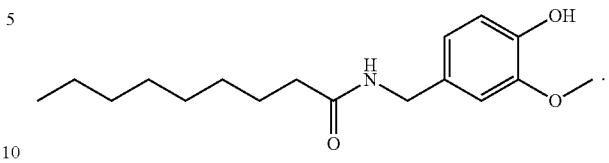

As used herein, the term "alkyl," by itself or as part of another substituent means, unless otherwise stated, a straight or branched chain hydrocarbon having the number of carbon atoms designated (i.e. $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific example is ($C_1$-$C_6$)alkyl, particularly ethyl, methyl, isopropyl, isobutyl, n-pentyl, n-hexyl and cyclopropylmethyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. A specific example is ($C_1$-$C_3$) alkoxy, particularly ethoxy and methoxy.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings can be attached together in a pendent manner, such as a biphenyl, or can be fused, such as naphthalene. Examples include phenyl, anthracyl, and naphthyl. A specific example is phenyl and naphthyl.

As used herein, the term "cycloalkyl," by itself or as part of another substituent means, unless otherwise stated, a cyclic chain hydrocarbon having the number of carbon atoms designated (i.e. $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$) cycloalkyl, particularly cyclopropyl, cyclobutyl, cyclopentyl and cyclohexyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms can be optionally oxidized, and the nitrogen atom can be optionally quaternized. The heterocyclic system can be attached, unless otherwise stated, at any heteroatom or carbon atom that affords a stable structure. A heterocycle can be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl can include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution can be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of C$_{1-6}$ alkyl, —OH, C$_{1-6}$ alkoxy, halo, amino, acetamido and nitro. In yet other embodiments, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain can be branched, straight or cyclic, with straight being preferred.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery of novel multi-aromatic, multisubstituted compounds, or a salt or solvate thereof. In certain embodiments, the compounds of the invention are generated by condensing (i) at least two phenolic (aromatic) monomers or aniline (aromatic) monomers, and (ii) an aromatic, aliphatic or heteroaromatic aldehyde or ketone monomer, which can be a mono-aldehyde, mono-ketone, poly-aldehyde, poly-ketone, or any combinations thereof.

In certain embodiments, at least one of the monomers is derived from bio-based resources, such as, but not limited to, lignin, cashew nutshell liquid, tannin, cellulose, hemicellulose, plant oils, terpenes, animal fats, herbs, spices, chitin, chitosan, and/or aquatic biomass. In other embodiments, each of the monomers is derived from bio-based resources.

In certain embodiments, the compounds of the invention are bis- or poly-phenolic compounds (or derivatives thereof), which are generated by condensing a phenolic or furan monomer with a phenolic monomer, which can be derived from natural sources such as cashew nut shell liquid and/or capsaicin. In other embodiments, the phenolic monomer is derived from cashew nutshell liquid, herbs, spices, and/or tannins.

As used herein, the term "aniline" refers to a compound where an amino group (or a protected amino group) is covalently linked to a phenyl group. In certain embodiments, a derivatized aniline group refers to a derivative of the aniline amino group. As used herein, the term "phenol" or "phenolic" refers to a compound where a hydroxy group (or a protected hydroxy group) is covalently linked to a phenyl group. In certain embodiments, a derivatized phenolic group refers to a derivative of the phenolic hydroxyl group.

In certain embodiments, the compounds of the invention can be used to generate polymeric materials that have water absorption and/or retention that is comparable or lower than those of polymeric materials known in the art, such as those prepared using BPA.

In certain embodiments, the compounds of the invention can be used to generate polymeric materials that have toughness that is comparable or higher than those of polymeric materials known in the art, such as those prepared using BPA.

In certain embodiments, the compounds of the invention can be used to generate polymeric materials that have a glass transition temperature that is comparable or higher than those of polymeric materials known in the art, such as those prepared using BPA.

In certain embodiments, at least one ring from the group selected from rings a-d, as applicable, for any compound recited herein is

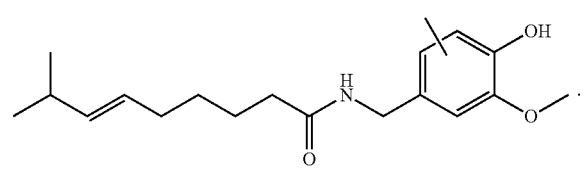

Such derivatives can be obtained using capsaicin as a starting material. In non-limiting embodiments, the compounds comprising at least one of these rings have anti-fouling and/or anti-inflammatory properties.

In certain embodiments, at least one ring from the group selected from rings a-d, as applicable, for any compound recited herein is

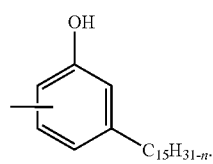

Such derivatives can be obtained using cardanol as a starting material. In certain embodiments, the compounds comprising at least one of these rings are liquid at room temperature. In other embodiments, such compounds form polymers with good toughness and low water absorption. Cardanol has the Formula shown below, wherein each of the double bonds is independently optionally reduced:

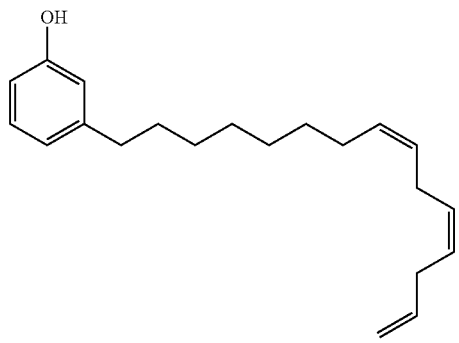

Cardanol has the Formula

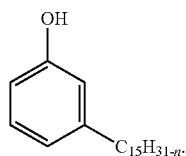

wherein n is 0, 2, 4 or 6. This is a phenolic lipid obtained from anacardic acid, the main component of cashew nutshell liquid (CNSL), which is a byproduct of cashew nut processing. Only a fraction of the cardanol obtained from cashew nut processing is currently used in the industrial field. In certain embodiments, at least one of $R_{6-10}$ or $R_{11-15}$ is $C_1$-$C_{20}$ aliphatic hydrocarbyl, such as for example $C_{15}H_{31-n}$, wherein n is 0, 2, 4 or 6.

In one aspect, the invention provides a compound of Formula (Ia), or a salt or solvate thereof, which can be prepared from a monomer comprising at least one aromatic aldehyde group:

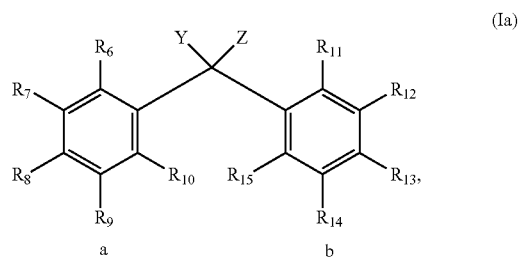

wherein:

Z is H;

each one of $R_6$-$R_{15}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, halogen, —NH$_2$, furyl, benzyl, substituted furyl, and substituted benzyl, wherein at least one selected from the group consisting of $R_6$-$R_{10}$ is —OH (or a protected version thereof), and wherein at least one selected from the group consisting of $R_{11}$-$R_{15}$ is —OH (or a protected version thereof);

Y is

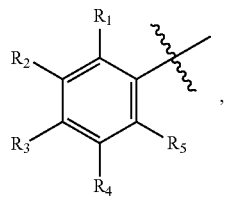, wherein each one of $R_1$-$R_5$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, halogen, —$NH_2$, furyl, benzyl, substituted furyl and substituted benzyl.

In certain embodiments, each furyl or benzyl is independent substituted with at least one selected from the group consisting of $C_1$-$C_{20}$ alkyl (in certain embodiments, $C_1$-$C_6$ alkyl), $C_1$-$C_6$ alkoxy, C acyloxy, —OH, and halogen.

The compound of Formula (Ia), or a salt or solvate thereof, can be prepared from two phenolic-containing and/or aniline-containing monomers, each of which contains at least one unsubstituted position on the phenyl ring, such as:

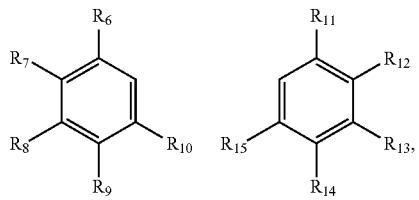

and an aromatic monomer comprising at least one aromatic aldehyde group, such as:

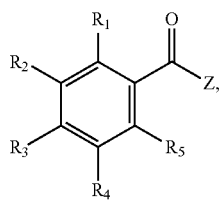

wherein Z and $R_1$-$R_{15}$ are as defined for (Ia) elsewhere herein.

Non-limiting examples of phenolic-containing monomers that can be used to prepare (Ia) include, but are not limited to, carvacrol, thymol, eugenol, crocin, gallic acid, cardanol, naturally occurring capsaicin, synthetic derivatives or analogues of capsaicin, quercetin, kaemferol, catechin, and so forth.

In certain embodiments, at least one selected from the group consisting of $R_6$-$R_{10}$ is —OH (or a protected version thereof). In other embodiments, at least one selected from the group consisting of $R_{11}$-$R_{15}$ is —OH (or a protected version thereof). In yet other embodiments, the phenolic-containing monomer has at least one unprotected phenolic hydroxy group (i.e., it is a phenol itself). In yet other embodiments, the phenolic aromatic monomer has at least one phenolic hydroxy group protected as a $C_1$-$C_6$ alkyl ether (forming a $C_1$-$C_6$ alkoxy group) or $C_1$-$C_6$ aliphatic ester (forming a $C_1$-$C_6$ acyloxy group). Non-limiting examples of such esters and ethers include $C_1$-$C_6$ alkyl ether (such as, but not limited to, methyl ether, ethyl ether, n-propyl ether, isopropyl ether, n-butyl ether, isobutyl ether, t-butyl ether, sec-butyl ether and so forth), and $C_1$-$C_6$ aliphatic esters (such as, but not limited to, formyloxy, acetoxy, propionoxy, acryloyloxy, methacrylyloxy and so forth).

Non-limiting examples of mono-aldehydes that can be used to prepare (Ia) include, but are not limited to, 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, and any ester or ether thereof.

In certain embodiments, at least one of $R_{1-5}$ is OH. In other embodiments, at least one of $R_{1-5}$ is $C_1$-$C_{20}$ aliphatic hydrocarbyl. In yet other embodiments, at least one of $R_{1-5}$ is $C_1$-$C_6$ alkoxy. In yet other embodiments, at least one of $R_{1-5}$ is $C_1$-$C_6$ acyloxy. In yet other embodiments, at least one of $R_{1-5}$ is not H.

In certain embodiments, at least one of $R_6$-$R_{10}$ and $R_{11}$-$R_{15}$ is acyloxy. Without wishing to be limited by any theory, such compounds have reduced toxic effects in a subject. In certain embodiments, such compounds cause reduced endocrine disruption as compared to compounds of the prior art.

In another aspect, the invention further provides a compound of Formula (Ib), or a salt or solvate thereof, which can be prepared from a monomer comprising at least one aldehyde group:

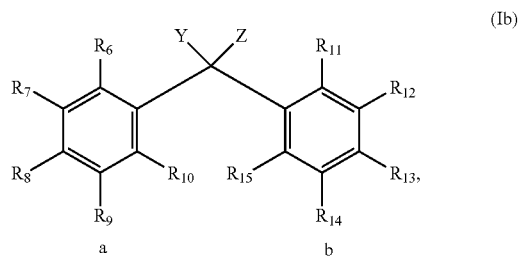

wherein:
Z is H;
each one of $R_6$-$R_{15}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, halogen, —$NH_2$, furyl, benzyl, substituted furyl, and substituted benzyl,
wherein at least one selected from the group consisting of $R_6$-$R_{10}$ is —OH (or a protected version thereof), and
wherein at least one selected from the group consisting of $R_{11}$-$R_{15}$ is —OH (or a protected version thereof);
Y is selected from the group consisting of:

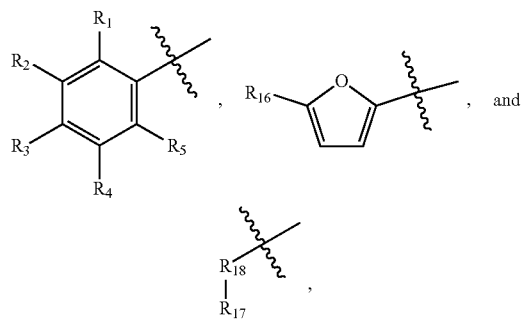

wherein:
each one of $R_1$-$R_5$ and $R_{17}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, halogen, —$NH_2$, furyl, benzyl, substituted furyl and substituted benzyl,
$R_{18}$ is a $C_1$-$C_6$ alkylene group, and
$R_{16}$ is selected from the group consisting of H, —$CH_2OH$, —$CH_2O(C_1$-$C_6$ alkyl), —$CH_2$(halogen), —$CH_2NH_2$, $C_1$-$C_{20}$ alkyl (in certain embodiments, $C_1$-$C_6$ alkyl), $C_1$-$C_6$ alkoxy, $C_1$-$C_6$ acyloxy, furyl, benzyl, substituted furyl, and substituted benzyl.

In certain embodiments, each furyl or benzyl is independently substituted with at least one selected from the group consisting of $C_1$-$C_{20}$ alkyl (in certain embodiments, $C_1$-$C_6$ alkyl), $C_1$-$C_6$ alkoxy, $C_1$-$C_6$ acyloxy, —OH, and halogen.

The compound of Formula (Ib), or a salt or solvate thereof, can be prepared from two phenolic-containing and/or aniline-containing monomers, each of which contains at least one unsubstituted position on the phenyl ring, such as:

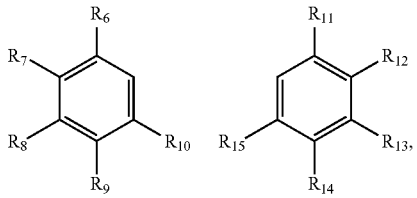

and an aromatic, aliphatic or heteroaromatic monomer comprising at least one aldehyde group, such as:

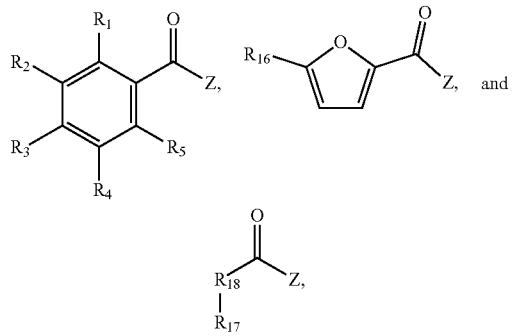

wherein Z and $R_1$-$R_{18}$ are as defined for (Ib) elsewhere herein.

Non-limiting examples of phenolic-containing monomers that can be used to prepare (Ib) include, but are not limited to, phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, carvacrol, thymol, eugenol, crocin, gallic acid, pyrogallol, cardanol, capsaicin, quercetin, kaemferol, catechin, and so forth.

In certain embodiments, at least one selected from the group consisting of $R_6$-$R_{10}$ is —OH (or a protected version thereof). In other embodiments, at least one selected from the group consisting of $R_{11}$-$R_{15}$ is —OH (or a protected version thereof). In yet other embodiments, the phenolic-containing monomer has at least one unprotected phenolic hydroxy group (i.e., it is a phenol itself). In yet other embodiments, the phenolic aromatic monomer has at least one phenolic hydroxy group protected as a $C_1$-$C_6$ alkyl ether (forming a $C_1$-$C_6$ alkoxy) or $C_1$-$C_6$ aliphatic ester (forming a $C_1$-$C_6$ acyloxy). Non-limiting examples of such esters and ethers include $C_1$-$C_6$ alkyl ether (such as, but not limited to, methyl ether, ethyl ether, n-propyl ether, isopropyl ether, n-butyl ether, isobutyl ether, t-butyl ether, sec-butyl ether and so forth), and $C_1$-$C_6$ aliphatic esters (such as, but not limited to, formyloxy, acetoxy, propionoxy, acryloyloxy, methacrylyloxy and so forth).

In certain embodiments, the aldehyde monomer is aliphatic. In other embodiments, the aldehyde monomer is aromatic or heteroaromatic.

Non-limiting examples of mono-aldehydes that can be used to prepare (Ib) include, but are not limited to, furfural, cuminaldehyde, piperine, cinnamaldehyde, citral, α-crocin, anisaldehyde, and any ester or ether thereof. In certain embodiments, the mono-aldehyde does not comprise formaldehyde, paraformaldehyde, and/or vanillin.

In certain embodiments, at least one of $R_{1-5}$ and $R_{17}$ is OH. In other embodiments, at least one of $R_{1-5}$ is $C_1$-$C_{20}$ aliphatic hydrocarbyl. In yet other embodiments, at least one of $R_{1-5}$ is $C_1$-$C_6$ alkoxy. In yet other embodiments, at least one of $R_{1-5}$ is $C_1$-$C_6$ acyloxy. In yet other embodiments, the aldehyde monomer is aliphatic. In yet other embodiments, at least one of $R_{1-5}$ is not H.

In other embodiments, at least one of $R_{1-5}$ is $C_1$-$C_{20}$ aliphatic hydrocarbyl. In yet other embodiments, at least one of $R_{1-5}$ is $C_1$-$C_6$ alkoxy. In yet other embodiments, at least one of $R_{1-5}$ is $C_1$-$C_6$ acyloxy. In yet other embodiments, at least one of $R_{1-5}$ is not H.

In certain embodiments, at least one of $R_6$-$R_{10}$ and $R_{11}$-$R_{15}$ are acyloxy. Without wishing to be limited by any theory, such compounds have reduced toxic effects in a subject. In certain embodiments, such compounds cause reduced endocrine disruption as compared to compounds of the prior art.

In yet another aspect, the invention further provides a compound of Formula (Ic), or a salt or solvate thereof, which can be prepared from a monomer comprising at least one aromatic ketone group:

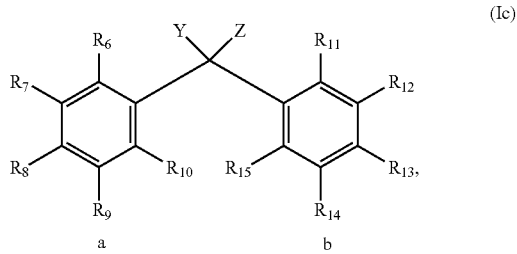

wherein:
Z is selected from the group consisting of —$CH_3$ and —$CH_2CH_3$;
each one of $R_6$-$R_{15}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, halogen, —$NH_2$, furyl, benzyl, substituted furyl, and substituted benzyl,
wherein at least one selected from the group consisting of $R_6$-$R_{10}$ is —OH (or a protected version thereof), and
wherein at least one selected from the group consisting of $R_{11}$-$R_{15}$ is —OH (or a protected version thereof);

Y is selected from the group consisting of:

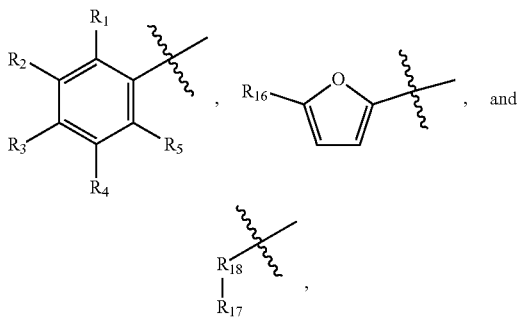

wherein:
each one of $R_1$-$R_5$ and $R_{17}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, halogen, —NH$_2$, furyl, benzyl, substituted furyl and substituted benzyl, $R_{18}$ is a $C_1$-$C_6$ alkylene group, and $R_{16}$ is selected from the group consisting of H, —CH$_2$OH, —CH$_2$O($C_1$-$C_6$ alkyl), —CH$_2$(halogen), —CH$_2$NH$_2$, $C_1$-$C_{20}$ alkyl (in certain embodiments, $C_1$-$C_6$ alkyl), $C_1$-$C_6$ alkoxy, $C_1$-$C_6$ acyloxy, furyl, benzyl, substituted furyl and substituted benzyl.

In certain embodiments, each furyl or benzyl is independently substituted with at least one selected from the group consisting of $C_1$-$C_{20}$ alkyl (in certain embodiments, $C_1$-$C_6$ alkyl), $C_1$-$C_6$ alkoxy, $C_1$-$C_6$ acyloxy, —OH, and halogen.

The compound of Formula (Ic), or a salt or solvate thereof, can be prepared from two phenolic-containing and/or aniline-containing monomers, each of which contains at least one unsubstituted position on the phenyl ring, such as:

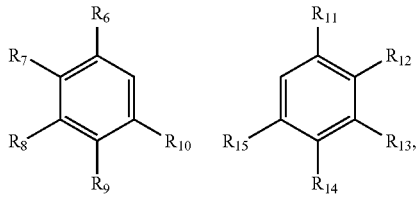

and an aromatic, aliphatic or heteroaromatic monomer comprising at least one aromatic ketone group, such as:

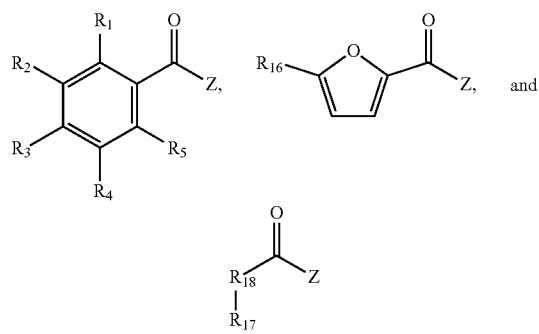

wherein Z and $R_1$-$R_{18}$ are as defined for (Ic) elsewhere herein.

Non-limiting examples of phenolic-containing monomers that can be used to prepare (Ic) include, but are not limited to, phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, carvacrol, thymol, eugenol, crocin, gallic acid, cardanol, capsaicin, quercetin, kaemferol, catechin, and so forth.

In certain embodiments, at least one selected from the group consisting of $R_6$-$R_{10}$ is —OH (or a protected version thereof). In other embodiments, at least one selected from the group consisting of $R_{11}$-$R_{15}$ is —OH (or a protected version thereof). In yet other embodiments, the phenolic-containing monomer has at least one unprotected phenolic hydroxy group (i.e., it is a phenol itself). In yet other embodiments, the phenolic aromatic monomer has at least one phenolic hydroxy group protected as a $C_1$-$C_6$ alkyl ether (forming a $C_1$-$C_6$ alkoxy) or $C_1$-$C_6$ aliphatic ester (forming a $C_1$-$C_6$ acyloxy). Non-limiting examples of such esters and ethers include $C_1$-$C_6$ alkyl ether (such as, but not limited to, methyl ether, ethyl ether, n-propyl ether, isopropyl ether, n-butyl ether, isobutyl ether, t-butyl ether, sec-butyl ether and so forth), and $C_1$-$C_6$ aliphatic esters (such as, but not limited to, formyloxy, acetoxy, propionoxy, acryloyloxy, methacrylyloxy and so forth).

In certain embodiments, the ketone monomer is aliphatic. In other embodiments, the ketone monomer is aromatic or heteroaromatic. In yet other embodiments, the mono-ketone does not include acetone.

Non-limiting examples of aliphatic mono-ketones contemplated within the invention include, but are not limited to, 2-heptanone, acetophenone, ethyl phenyl ketone, 2-furyl methyl ketone and any ester or ether thereof.

In certain embodiments, $R_{16}$ is —CH$_2$OH. In other embodiments, at least one of $R_{1-5}$ and $R_{16}$ is $C_1$-$C_{20}$ aliphatic hydrocarbyl. In yet other embodiments, at least one of $R_{1-5}$ and $R_{16}$ is $C_1$-$C_6$ alkoxy. In yet other embodiments, at least one of $R_{1-5}$ and $R_{16}$ is $C_1$-$C_6$ acyloxy. In yet other embodiments, at least one of $R_{1-5}$ and $R_{16}$ is not H.

In certain embodiments, at least one of $R_{1-5}$ and $R_{17}$ is OH. In other embodiments, at least one of $R_{1-5}$ and $R_{17}$ is $C_1$-$C_{20}$ aliphatic hydrocarbyl. In yet other embodiments, at least one of $R_{1-5}$ and $R_{17}$ is $C_1$-$C_6$ alkoxy. In yet other embodiments, at least one of $R_{1-5}$ and $R_{17}$ is $C_1$-$C_6$ acyloxy. In yet other embodiments, at least one of $R_{1-5}$ and $R_{17}$ is not H.

In certain embodiments, at least one of $R_6$-$R_{10}$ and $R_{11}$-$R_{15}$ are acyloxy. Without wishing to be limited by any theory, such compounds have reduced toxic effects in a subject. In certain embodiments, such compounds cause reduced endocrine disruption as compared to compounds of the prior art.

In yet another aspect, the invention further provides a compound of Formula (Id), or a salt or solvate thereof, which can be prepared from monomer comprising at least one aldehyde and/or ketone group:

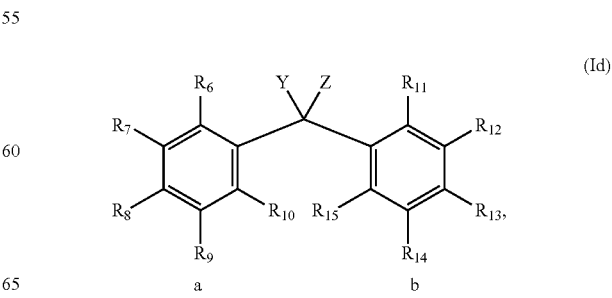

wherein:

Z is selected from the group consisting of H, —CH$_3$ and —CH$_2$CH$_3$;

each one of R$_6$-R$_{15}$ is independently selected from the group consisting of H, —OH, C$_1$-C$_{20}$ alkyl (in certain embodiments, C$_1$-C$_6$ alkyl), C$_1$-C$_6$ alkoxy, C$_1$-C$_6$ acyloxy, halogen, —NH$_2$, furyl, benzyl, substituted furyl, and substituted benzyl, wherein at least one selected from the group consisting of R$_6$-R$_{10}$ is —NH$_2$ (or a protected version thereof), and wherein at least one selected from the group consisting of R$_{11}$-R$_{15}$ is —NH$_2$ (or a protected version thereof);

Y is selected from the group consisting of:

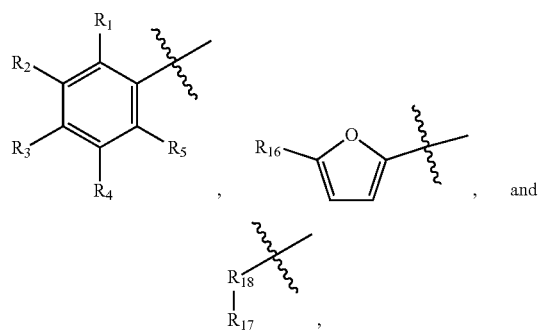

wherein:

each one of R$_1$-R$_5$ and R$_{17}$ is independently selected from the group consisting of H, —OH, C$_1$-C$_{20}$ alkyl (in certain embodiments, C$_1$-C$_6$ alkyl), C$_1$-C$_6$ alkoxy, C$_1$-C$_6$ acyloxy, halogen, —NH$_2$, furyl, benzyl, substituted furyl, and substituted benzyl, R$_{18}$ is a C$_1$-C$_6$ alkylene group, and R$_{16}$ is selected from the group consisting of H, —CH$_2$OH, —CH$_2$O(C$_1$-C$_6$ alkyl), —CH$_2$(halogen), —CH$_2$NH$_2$, C$_1$-C$_{20}$ alkyl (in certain embodiments, C$_1$-C$_6$ alkyl), C$_1$-C$_6$ alkoxy, C$_1$-C$_6$ acyloxy, furyl, benzyl, substituted furyl and substituted benzyl.

In certain embodiments, each furyl or benzyl is independently substituted with at least one selected from the group consisting of C$_1$-C$_{20}$ alkyl (in certain embodiments, C$_1$-C$_6$ alkyl), C$_1$-C$_6$ alkoxy, C$_1$-C$_6$ acyloxy, —OH, and halogen.

The compound of Formula (Id), or a salt or solvate thereof, can be prepared from two phenolic-containing and/or aniline-containing monomers, each of which contains at least one unsubstituted position on the phenyl ring, such as:

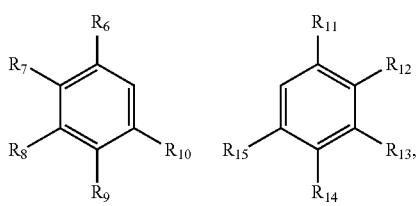

and an aromatic, aliphatic or heteroaromatic mono-aldehyde or mono-ketone monomer, such as:

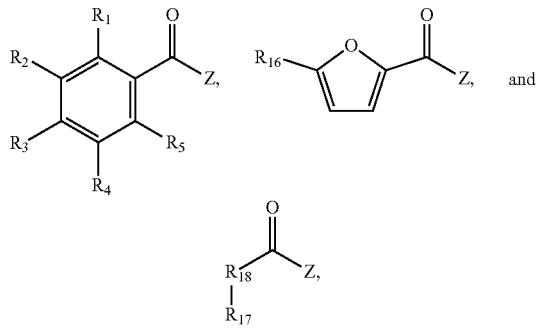

wherein Z and R$_1$-R$_{17}$ are as defined for (Id) elsewhere herein.

Non-limiting examples of phenolic-containing monomers contemplated within the invention include, but are not limited to, phenol, catechol (1,2-dihydroxybenzene), resorcinol, 4-methylcathecol, guaiacol (2-methoxy-phenol), 1,2,3-trihydroxy-phenol (pyrogalol), syringol (1,3-dimethoxy-2-hydroxy-benzene), hydroquinone, 4-methoxyphenol, carvacrol, thymol, eugenol, crocin, gallic acid, pyrogallol, cardanol, capsaicin, quercetin, kaemferol, catechin, and so forth.

Non-limiting examples of aniline-containing monomers contemplated within the invention include, but are not limited to aniline, 2-methylaniline, 3-methylaniline, 4-methylaniline, 2-methoxyaniline, 3-methoxyaniline, 4-methoxy aniline, 2,5-dimethylaniline, 2,6-dimethylaniline, 3,5-dimethylaniline, 2,5-dimethoxyaniline, 2,6-dimethoxyaniline, 3,5-dimethoxyaniline, and p-cymene aniline (1-amino-2-methyl-5-isopropyl benzene).

In certain embodiments, at least one selected from the group consisting of R$_6$-R$_{10}$ is —NH$_2$ (or a protected version thereof). In other embodiments, at least one selected from the group consisting of R$_{11}$-R$_{15}$ is —NH$_2$ (or a protected version thereof). In yet other embodiments, the aniline-containing monomer has at least one unprotected aniline amine group (i.e., it is an aniline itself). In yet other embodiments, the aniline monomer has at least one aniline amine group protected as a C$_1$-C$_6$ alkyl amine, (C$_1$-C$_6$ alkyl)(C$_1$-C$_6$ alkyl) amine or C$_1$-C$_6$ aliphatic amide. Non-limiting examples of such groups include C$_1$-C$_6$ alkyl groups (such as, but not limited to, methyl, ethyl, n-propyl, isopropyl, n-butyl, isobutyl, t-butyl, sec-butyl and so forth), and C$_1$-C$_6$ acyl groups.

In certain embodiments, the aldehyde or ketone monomer is aliphatic. In other embodiments, the aldehyde or ketone monomer is aromatic or heteroaromatic.

Non-limiting examples of mono-aldehydes contemplated within the invention include, but are not limited to, 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, furfural, cuminaldehyde, piperine, cinnamaldehyde, citral, α-crocin, anisaldehyde and any ester or ether thereof. In certain embodiments, the mono-aldehyde does not comprise formaldehyde and/or paraformaldehyde.

Non-limiting examples of mono-ketones contemplated within the invention include, but are not limited to, 2-heptanone, acetophenone, ethyl phenyl ketone, 2-furyl methyl ketone and any ester or ether thereof. In certain embodiments, the mono-ketone does not comprise acetone.

In certain embodiments, R$_{16}$ is —CH$_2$OH. In other embodiments, at least one of R$_{1-5}$ and R$_{16}$ is C$_1$-C$_{20}$ aliphatic hydrocarbyl. In yet other embodiments, at least one of $R_{1-5}$ and $R_{16}$ is $C_1$-$C_6$ alkoxy. In yet other embodiments, at least one of $R_{1-5}$ and $R_{16}$ is $C_1$-$C_6$ acyloxy. In yet other embodiments, at least one of $R_{1-5}$ and $R_{16}$ is not H.

In certain embodiments, at least one of $R_{1-5}$ and $R_{17}$ is OH. In other embodiments, at least one of $R_{1-5}$ and $R_{17}$ is $C_1$-$C_{20}$ aliphatic hydrocarbyl. In yet other embodiments, at least one of $R_{1-5}$ and $R_{17}$ is $C_1$-$C_6$ alkoxy. In yet other embodiments, at least one of $R_{1-5}$ and $R_{17}$ is $C_1$-$C_6$ acyloxy. In yet other embodiments, at least one of $R_{1-5}$ and $R_{17}$ is not H.

In certain embodiments, at least one of $R_6$-$R_{10}$, $R_{11}$-$R_{15}$, is acyloxy or at least two $R_6$-$R_{10}$, $R_{11}$-$R_{15}$ are alkyl. Without wishing to be limited by any theory, such compounds have reduced toxic effects in a subject. In certain embodiments, such compounds cause reduced mutagenicity as compared to compounds of the prior art.

In yet another aspect, the invention further provides a compound of Formula (Ie), or a salt or solvate thereof, which acts as a pH indicator and can be prepared from a monomer comprising at least one aldehyde group:

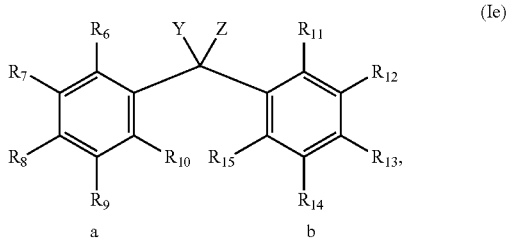

(Ie)

wherein:

Z is H;

each one of $R_6$-$R_{15}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, —NH$_2$, furyl, benzyl, substituted furyl, and substituted benzyl, wherein rings a and b are independently substituted with at least one electron donating group and no strong electron withdrawing groups and (Ie) has greater electron donating character than the corresponding unsubstituted analogue of (Ie);

wherein at least one selected from the group consisting of $R_6$-$R_{10}$ is —OH or —NH$_2$ (or a protected version thereof), and wherein at least one selected from the group consisting of $R_{11}$-$R_{15}$ is —OH or —NH$_2$ (or a protected version thereof);

Y is selected from the group consisting of:

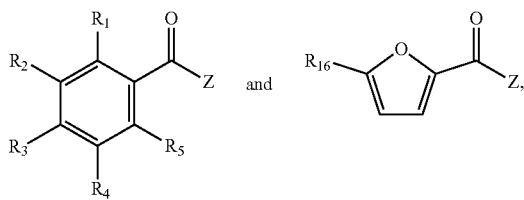

wherein:

each one of $R_1$-$R_5$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, —NH$_2$, furyl, benzyl, substituted furyl, and substituted benzyl, wherein at least one of $R_1$-$R_5$ is electron donating group and none of $R_1$-$R_5$ is strongly electron withdrawing; and $R_{16}$ is selected from the group consisting of H, —CH$_2$OH, —CH$_2$O(C$_1$-$C_6$ alkyl), —CH$_2$(halogen), —CH$_2$NH$_2$, $C_1$-$C_{20}$ alkyl (in certain embodiments, $C_1$-$C_6$ alkyl), $C_1$-$C_6$ alkoxy, $C_1$-$C_6$ acyloxy, furyl, benzyl, substituted furyl, and substituted benzyl.

In certain embodiments, each furyl or benzyl is independently substituted with at least one selected from the group consisting of $C_1$-$C_{20}$ alkyl (in certain embodiments, $C_1$-$C_6$ alkyl), $C_1$-$C_6$ alkoxy, $C_1$-$C_6$ acyloxy, —OH, and halogen.

Non-limiting examples of phenolic-containing monomers contemplated within the invention include, but are not limited to, phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, carvacrol, thymol, eugenol, crocin, gallic acid, cardanol, capsaicin, quercetin, kaemferol, catechin, and so forth.

Non-limiting examples of aniline-containing monomers contemplated within the invention include, but are not limited to aniline, 2-methylaniline, 3-methylaniline, 4-methylaniline, 2-methoxyaniline, 3-methoxyaniline, 4-methoxyaniline, 2,5-dimethylaniline, 2,6-dimethylaniline, 3,5-dimethylaniline, 2,5-dimethoxyaniline, 2,6-dimethoxyaniline, 3,5-dimethoxyaniline, and p-cymene aniline (1-amino-2-methyl-5-isopropyl benzene).

In certain embodiments, at least one selected from the group consisting of $R_6$-$R_{10}$ is —OH or —NH$_2$ (or a protected version thereof). In other embodiments, at least one selected from the group consisting of $R_{11}$-$R_{15}$ is —OH or —NH$_2$ (or a protected version thereof). In yet other embodiments, the phenolic-containing monomer has at least one unprotected phenolic hydroxy group (i.e., it is a phenol itself). In yet other embodiments, the phenolic aromatic monomer has at least one phenolic hydroxy group protected as a $C_1$-$C_6$ alkyl ether (forming a $C_1$-$C_6$ alkoxy) or $C_1$-$C_6$ aliphatic ester (forming a $C_1$-$C_6$ acyloxy). Non-limiting examples of such esters and ethers include $C_1$-$C_6$ alkyl ether (such as, but not limited to, methyl ether, ethyl ether, n-propyl ether, isopropyl ether, n-butyl ether, isobutyl ether, t-butyl ether, sec-butyl ether and so forth), and $C_1$-$C_6$ aliphatic esters (such as, but not limited to, formyloxy, acetoxy, propionoxy, acryloyloxy, methacrylyloxy and so forth).

Non-limiting examples of mono-aldehydes contemplated within the invention include, but are not limited to, 3,4-dihydroxy-benzaldehyde, vanillin (4-hydroxy-3-methoxybenzaldehyde), 4-formyl-2-hydroxy-phenol, 4-formyl-2-methoxy-phenol, 3,4,5-trihydroxybenzaldehyde, cuminaldehyde, anisaldehyde, furfural, and any ester or ether thereof.

In certain embodiments, at least one of $R_{1-5}$ is OH. In other embodiments, at least one of $R_{1-5}$ is $C_1$-$C_{20}$ aliphatic hydrocarbyl. In yet other embodiments, at least one of $R_{1-5}$ is $C_1$-$C_6$ alkoxy. In yet other embodiments, at least one of $R_{1-5}$ is $C_1$-$C_6$ acyloxy. In yet other embodiments, at least one of $R_{1-5}$ is not H.

In yet another aspect, the invention further provides a multi-phenolic or multi-aniline compound of Formula (IIa), or a salt or solvate thereof, which can be prepared from a poly-aldehyde/ketone monomer (such as, for example, a di-aldehyde, a di-ketone, or a monomer comprising both an aldehyde and a ketone groups):

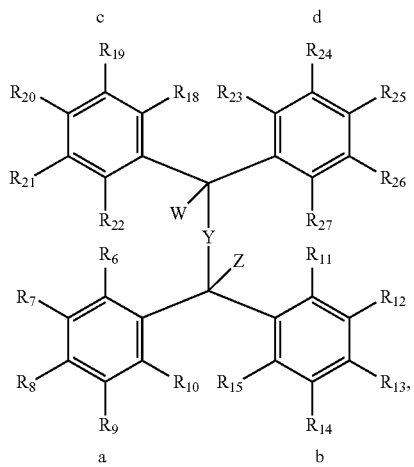

(IIa)

wherein:
Z and W are independently selected from the group consisting of H, —CH$_3$ and —CH$_2$CH$_3$; each one of R$_6$-R$_{15}$ and R$_{18}$-R$_{27}$ is independently selected from the group consisting of H, —OH, C$_1$-C$_{20}$ alkyl (in certain embodiments, C$_1$-C$_6$ alkyl), C$_1$-C$_6$ alkoxy, C$_1$-C$_6$ acyloxy, halogen, —NH$_2$, furyl, benzyl, substituted furyl, and substituted benzyl,
wherein at least one selected from the group consisting of R$_6$-R$_{10}$ is —OH or —NH$_2$ (or a protected version thereof),
wherein at least one selected from the group consisting of R$_{11}$-R$_{15}$ is —OH or —NH$_2$ (or a protected version thereof),
wherein at least one selected from the group consisting of R$_{18}$-R$_{22}$ is —OH or —NH$_2$ (or a protected version thereof), and
wherein at least one selected from the group consisting of R$_{23}$-R$_{27}$ is —OH or —NH$_2$ (or a protected version thereof);
Y is selected from the group consisting of:

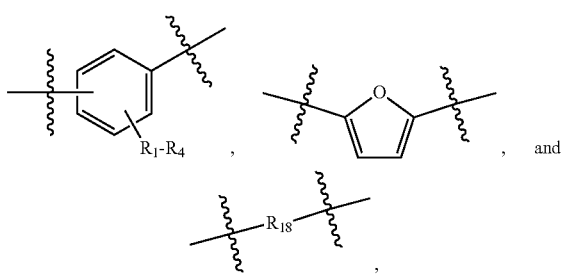

wherein:
each one of R$_1$-R$_4$ is independently selected from the group consisting of H, C$_1$-C$_{20}$ alkyl (in certain embodiments, C$_1$-C$_6$ alkyl), C$_1$-C$_6$ alkoxy, C$_1$-C$_6$ acyloxy, halogen, furyl, benzyl, substituted furyl, and substituted benzyl, and R$_{18}$ is a C$_1$-C$_6$ alkylene group.
In certain embodiments, each furyl or benzyl is independently substituted with at least one selected from the group consisting of C$_1$-C$_{20}$ alkyl (in certain embodiments, C$_1$-C$_6$ alkyl), C$_1$-C$_6$ alkoxy, C$_1$-C$_6$ acyloxy, —OH, and halogen.

The compound of Formula (II), or a salt or solvate thereof, can be prepared from four independently selected phenolic-containing and/or aniline-containing monomers, each of which contains at least one unsubstituted position on the phenyl ring, such as:

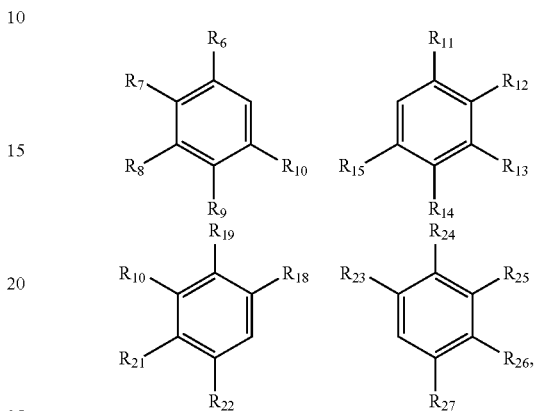

and an aromatic, aliphatic or heteroaromatic poly-aldehyde/ketone monomer, such as:

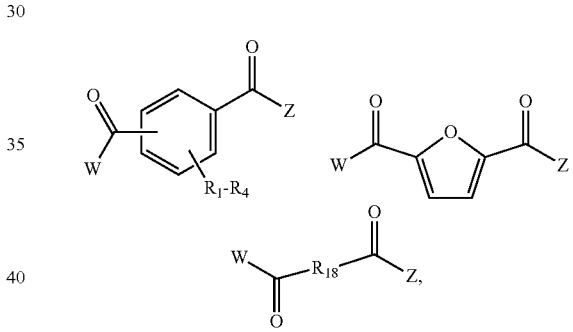

wherein W, Z, and R$_1$-R$_{27}$ are as defined for (II) elsewhere herein.

In certain embodiments, the aldehyde monomer is a poly-aldehyde, such as for example a di-aldehyde, tri-aldehyde, tetra-aldehyde, and so forth. In other embodiments, the ketone monomer is a poly-ketone, such as for example a di-ketone, tri-ketone, tetra-ketone, and so forth. In yet other embodiments, the aldehyde/ketone monomer contains at least one aldehyde group and at least one ketone group.

In certain embodiments, the aldehyde/ketone monomer is aromatic or heteroaromatic. In other embodiments, the aldehyde/ketone monomer is aliphatic. Non-limiting examples of poly-aldehydes contemplated within the invention include, but are not limited to aliphatic aldehydes, such as, succinaldehyde, glutaraldehyde, and/or HC(═O)(CH$_2$)$_i$C(═O)H, wherein i ranges from 0 to 10, and each CH$_2$ group is independently optionally substituted with one or two C$_1$-C$_6$ alkyl groups. Non-limiting examples of poly-aldehydes contemplated within the invention include, but are not limited to aromatic and heteroaromatic aldehydes, such as terephthaldehyde, furan 2,5-dialdehyde, 1,1'-biphenyl-4,4'-dicaboxaldehyde, 2,2'-bipyridyl-5,5'-dialdehyde, and curcumin.

Non-limiting examples of phenolic-containing monomers contemplated within the invention include, but are not limited to, phenol, catechol (1,2-dihydroxybenzene), resorcinol, 4-methylcathecol, guaiacol (2-methoxy-phenol), guaiacol (meth)acrylate, 1,2,3-trihydroxy-phenol (pyrogalol), syringol (1,3-dimethoxy-2-hydroxy-benzene), cardanol, capsaicin and so forth.

Non-limiting examples of aniline-containing monomers contemplated within the invention include, but are not limited to aniline, 2-methylaniline, 3-methylaniline, 4-methylaniline, 2-methoxyaniline, 3-methoxyaniline, 4-methoxyaniline, 2,5-dimethylaniline, 2,6-dimethylaniline, 3,5-dimethylaniline, 2,5-dimethoxyaniline, 2,6-dimethoxyaniline, 3,5-dimethoxyaniline, and p-cymene aniline (1-amino, 2-methyl, 5-isopropyl benzene).

In certain embodiments, at least one selected from the group consisting of $R_6$-$R_{10}$ is —OH or —NH$_2$ (or a protected version thereof). In other embodiments, at least one selected from the group consisting of $R_{11}$-$R_{15}$ is —OH or —NH$_2$ (or a protected version thereof). In other embodiments, at least one selected from the group consisting of $R_{18}$-$R_{22}$ is —OH or —NH$_2$ (or a protected version thereof). In other embodiments, at least one selected from the group consisting of $R_{23}$-$R_{27}$ is —OH or —NH$_2$ (or a protected version thereof). In yet other embodiments, the phenolic-containing monomer has at least one unprotected phenolic hydroxy group (i.e., it is a phenol itself). In yet other embodiments, the phenolic aromatic monomer has at least one phenolic hydroxy group protected as a $C_1$-$C_6$ alkyl ether (forming a $C_1$-$C_6$ alkoxy) or $C_1$-$C_6$ aliphatic ester (forming a $C_1$-$C_6$ acyloxy). Non-limiting examples of such esters and ethers include $C_1$-$C_6$ alkyl ether (such as, but not limited to, methyl ether, ethyl ether, n-propyl ether, isopropyl ether, n-butyl ether, isobutyl ether, t-butyl ether, sec-butyl ether and so forth), and $C_1$-$C_6$ aliphatic esters (such as, but not limited to, formyloxy, acetoxy, propionoxy, acryloyloxy, methacrylyloxy and so forth).

In certain embodiments, at least one of $R_6$-$R_{10}$, $R_{11}$-$R_{15}$, and $R_{18}$-$R_{22}$ and $R_{23}$-$R_{27}$ is acyloxy for such phenolic compounds. Without wishing to be limited by any theory, such compounds have reduced toxic effects in a subject. In certain embodiments, such compounds cause reduced endocrine disruption as compared to compounds of the prior art. In certain embodiments, at least two of $R_6$-$R_{10}$, $R_{11}$-$R_{15}$, and $R_{18}$-$R_{22}$ and $R_{23}$-$R_{27}$ are alkyl for such phenolic compounds. In certain embodiments, such compounds cause reduced mutagenicity as compared to compounds of the prior art.

In yet another aspect, the invention further provides a multi-phenolic or multi-aniline compound of Formula (IIb), or a salt or solvate thereof, which acts as a pH indicator and can be prepared from a monomer comprising at least one aldehyde group:

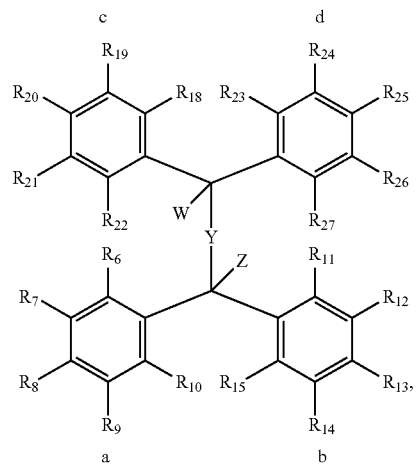

(IIb)

wherein:

Z and W are both H;

each one of $R_6$-$R_{15}$ is independently selected from the group consisting of H, —OH, $C_1$-$C_{20}$ alkyl (in certain embodiments, $C_1$-$C_6$ alkyl), $C_1$-$C_6$ alkoxy, $C_1$-$C_6$ acyloxy, —NH$_2$, furyl, benzyl, substituted furyl, and substituted benzyl, wherein rings a and b are independently substituted with at least one electron donating group and no strong electron withdrawing groups and (IIb) has greater electron donating character than the corresponding unsubstituted analogue of (IIb);

wherein at least one selected from the group consisting of $R_6$-$R_{10}$ is —OH or —NH$_2$ (or a protected version thereof), and wherein at least one selected from the group consisting of $R_{11}$-$R_{15}$ is —OH or —NH$_2$ (or a protected version thereof);

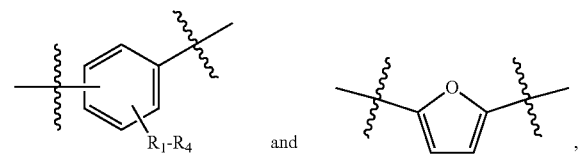

Y is selected from the group consisting of: wherein:

each one of $R_1$-$R_4$ is independently selected from the group consisting of H, $C_1$-$C_{20}$ alkyl (in certain embodiments, $C_1$-$C_6$ alkyl), $C_1$-$C_6$ alkoxy, $C_1$-$C_6$ acyloxy, furyl, benzyl, substituted furyl, and substituted benzyl, wherein at least one of $R_1$-$R_4$ is electron donating group and none of $R_1$-$R_4$ is strongly electron withdrawing.

In certain embodiments, each furyl or benzyl is independently substituted with at least one selected from the group consisting of $C_1$-$C_{20}$ alkyl (in certain embodiments, $C_1$-$C_6$ alkyl), $C_1$-$C_6$ alkoxy, $C_1$-$C_6$ acyloxy, —OH, and halogen.

The compound of Formula (IIb), or a salt or solvate thereof, can be prepared from four independently selected phenolic-containing and/or aniline-containing monomers, each of which contains at least one unsubstituted position on the phenyl ring, such as:

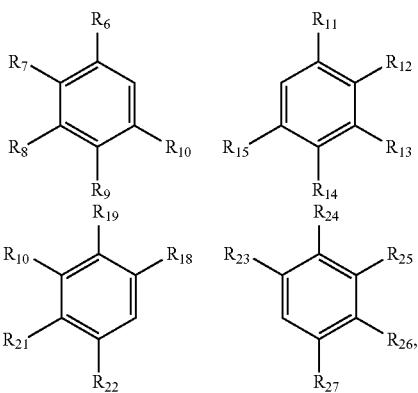

and an aromatic, aliphatic or heteroaromatic poly-aldehyde/ketone monomer, such as:

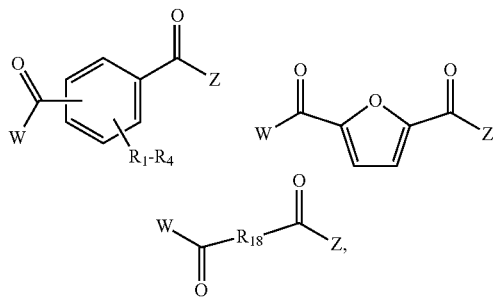

wherein W, Z, and $R_1$-$R_{27}$ are as defined for (IIb) elsewhere herein.

In certain embodiments, the aldehyde monomer is a poly-aldehyde, such as for example a di-aldehyde, tri-aldehyde, tetra-aldehyde, and so forth. In other embodiments, the ketone monomer is a poly-ketone, such as for example a di-ketone, tri-ketone, tetra-ketone, and so forth. In yet other embodiments, the aldehyde/ketone monomer contains at least one aldehyde group and at least one ketone group.

Non-limiting examples of phenolic-containing monomers contemplated within the invention include, but are not limited to, phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, carvacrol, thymol, eugenol, crocin, gallic acid, cardanol, capsaicin, quercetin, kaemferol, catechin, and so forth.

Non-limiting examples of aniline-containing monomers contemplated within the invention include, but are not limited to aniline, 2-methylaniline, 3-methylaniline, 4-methylaniline, 2-methoxyaniline, 3-methoxyaniline, 4-methoxyaniline, 2,5-dimethylaniline, 2,6-dimethylaniline, 3,5-dimethylaniline, 2,5-dimethoxyaniline, 2,6-dimethoxyaniline, 3,5-dimethoxyaniline, and p-cymene aniline (1-amino, 2-methyl, 5-isopropyl benzene).

In certain embodiments, the aldehyde monomer is aromatic or heteroaromatic. Non-limiting examples of poly-aldehydes contemplated within the invention include, but are not limited to aromatic and heteroaromatic aldehydes, such as terephthaldehyde, furan 2,5-dialdehyde, 1,1'-biphenyl-4,4'-dicaboxaldehyde, 2,2'-bipyridyl-5,5'-dialdehyde, and curcumin.

In certain embodiments, at least one selected from the group consisting of $R_6$-$R_{10}$ is —OH or —NH$_2$ (or a protected version thereof). In other embodiments, at least one selected from the group consisting of $R_{11}$-$R_{15}$ is —OH or —NH$_2$ (or a protected version thereof). In other embodiments, at least one selected from the group consisting of $R_{18}$-$R_{22}$ is —OH or —NH$_2$ (or a protected version thereof). In other embodiments, at least one selected from the group consisting of $R_{23}$-$R_{27}$ is —OH or —NH$_2$ (or a protected version thereof). In yet other embodiments, the phenolic-containing monomer has at least one unprotected phenolic hydroxy group (i.e., it is a phenol itself). In yet other embodiments, the phenolic aromatic monomer has at least one phenolic hydroxy group protected as a $C_1$-$C_6$ alkyl ether (forming a $C_1$-$C_6$ alkoxy) or $C_1$-$C_6$ aliphatic ester (forming a $C_1$-$C_6$ acyloxy). Non-limiting examples of such esters and ethers include $C_1$-$C_6$ alkyl ether (such as, but not limited to, methyl ether, ethyl ether, n-propyl ether, isopropyl ether, n-butyl ether, isobutyl ether, t-butyl ether, sec-butyl ether and so forth), and $C_1$-$C_6$ aliphatic esters (such as, but not limited to, formyloxy, acetoxy, propionoxy, acryloyloxy, methacrylyloxy and so forth).

In certain embodiments, the compound of the invention is a compound of Formula (III), or a salt or solvate thereof:

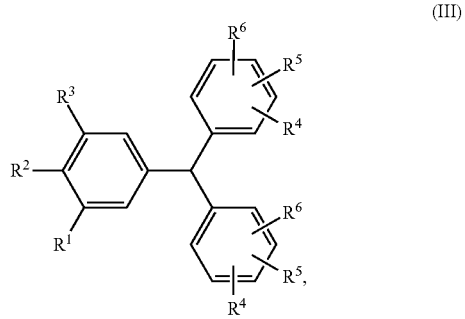

wherein in (III):
$R^1$, $R^2$ and $R^3$ are independently selected from the group consisting of H, OH, $C_1$-$C_{20}$ aliphatic hydrocarbyl, $C_1$-$C_6$ alkoxy, and $C_1$-$C_6$ acyloxy;
each occurrence of $R^4$ is independently OH or $C_1$-$C_6$ alkoxy;
each occurrence of $R^5$ and $R^6$ is independently selected from the group consisting of H, OH, $C_1$-$C_{20}$ aliphatic hydrocarbyl, $C_1$-$C_6$ alkoxy and $C_1$-$C_6$ acyloxy;
with the proviso that for each ring at least one selected from the group consisting of $R^5$ and $R^6$ is not H.

In certain embodiments, the compound of the invention is a compound of Formula (IV), or a salt or solvate thereof:

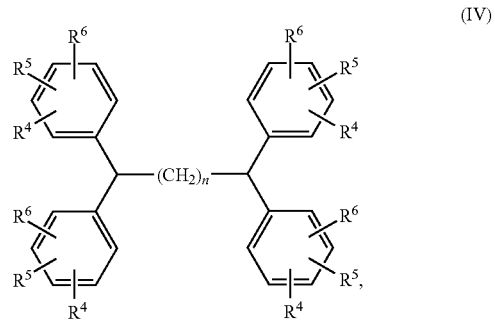

wherein in (IV):

n ranges from 0 to 10, wherein each CH$_2$ group is independently optionally substituted with one or two C$_1$-C$_6$ alkyl groups;

each occurrence of R$^4$ is independently OH or C$_1$-C$_6$ alkoxy;

each occurrence of R$^5$ and R$^6$ is independently selected from the group consisting of H, OH, C$_1$-C$_{20}$ aliphatic hydrocarbyl, C$_1$-C$_6$ alkoxy and C$_1$-C$_6$ acyloxy;

with the proviso that for each ring at least one selected from the group consisting of R$^5$ and R$^6$ is not H.

In certain embodiments, the compound of the invention is a compound of Formula (V), or a salt or solvate thereof:

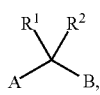

(V)

wherein:

R$^1$ and R$^2$ are independently selected from the group consisting of H and C$_1$-C$_{12}$ alkyl (such as but not limited to —CH$_3$ and —CH$_2$CH$_3$), or R$^1$ and R$^2$ combine to form =O;

ring A is selected from the group consisting of:

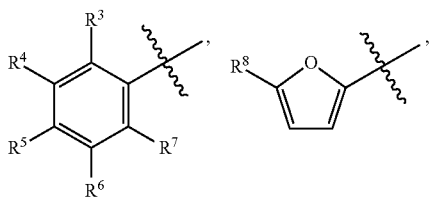

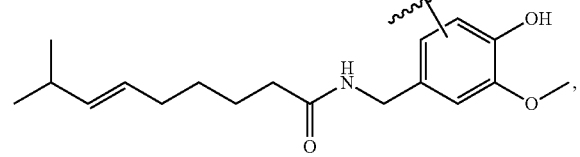

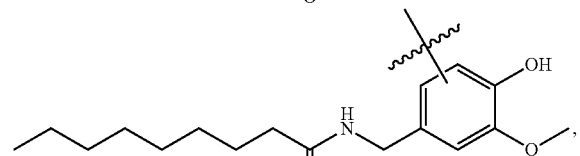

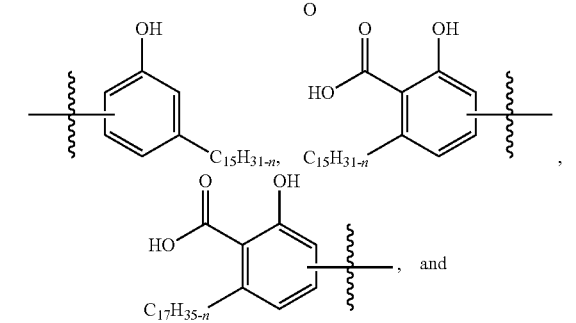

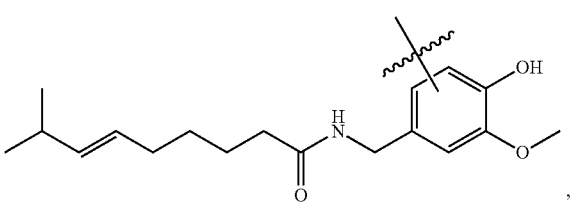

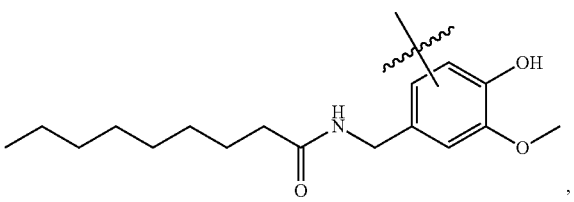

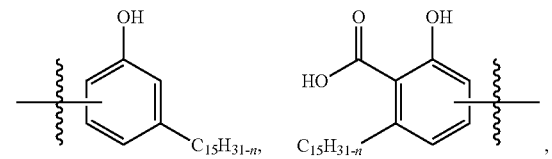

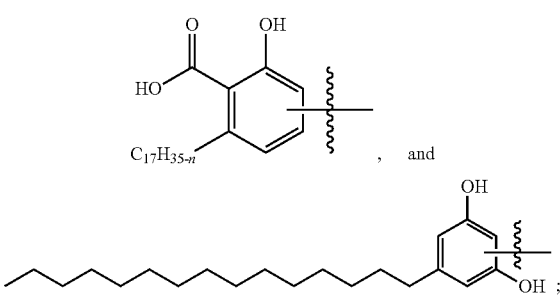

, and

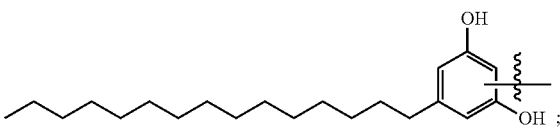

ring B is selected from the group consisting of:

each occurrence of n is independently selected from the group consisting of 0, 2, 4, and 6;

each one of R$^3$-R$^7$ is independently selected from the group consisting of H, —OH, hydroxymethyl, C$_1$-C$_{20}$ alkyl, C$_1$-C$_6$ alkoxy (such as, but not limited to, methyl ether, ethyl ether, n-propyl ether, isopropyl ether, n-butyl ether, isobutyl ether, t-butyl ether, sec-butyl ether and so forth), C$_1$-C$_6$ acyloxy (such as, but not limited to, formyloxy, acetoxy, propionoxy, acryloyloxy, and methacryloyloxy), halogen, —NH$_2$, furyl, benzyl, substituted furyl and substituted benzyl, wherein at least one selected from the group consisting of R$^3$-R$^7$ is —OH; and R$^8$ is selected from the group consisting of H, —CH$_2$OH, —CH$_2$O(C$_1$-C$_6$ alkyl), —CH$_2$(halogen), —CH$_2$NH$_2$, C$_1$-C$_{20}$ alkyl, C$_1$-C$_6$ alkoxy, C$_1$-C$_6$ acyloxy, furyl, benzyl, substituted furyl, and substituted benzyl.

In certain embodiments, the compound of Formula (V) is at least one selected from the group consisting of:

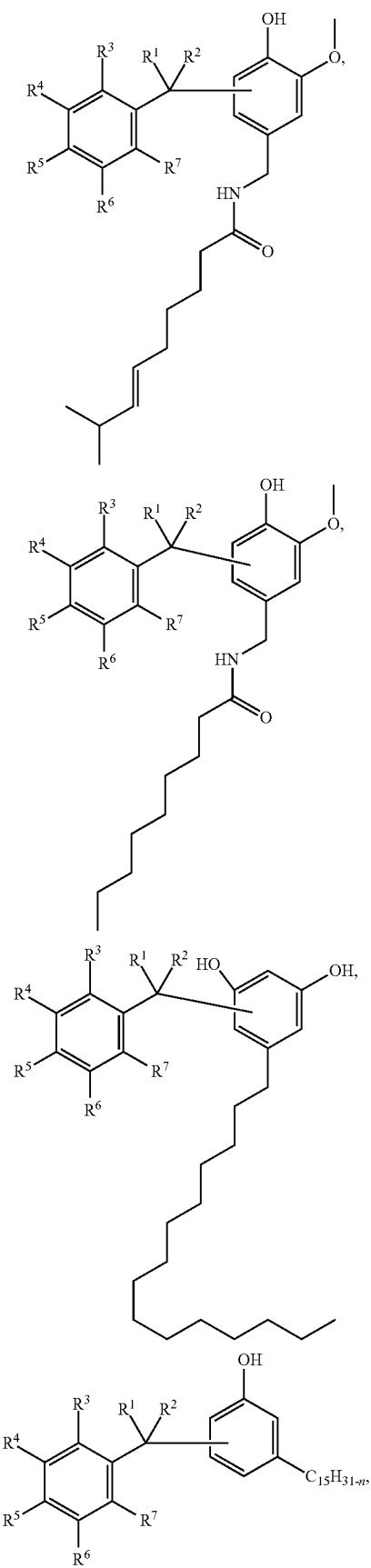
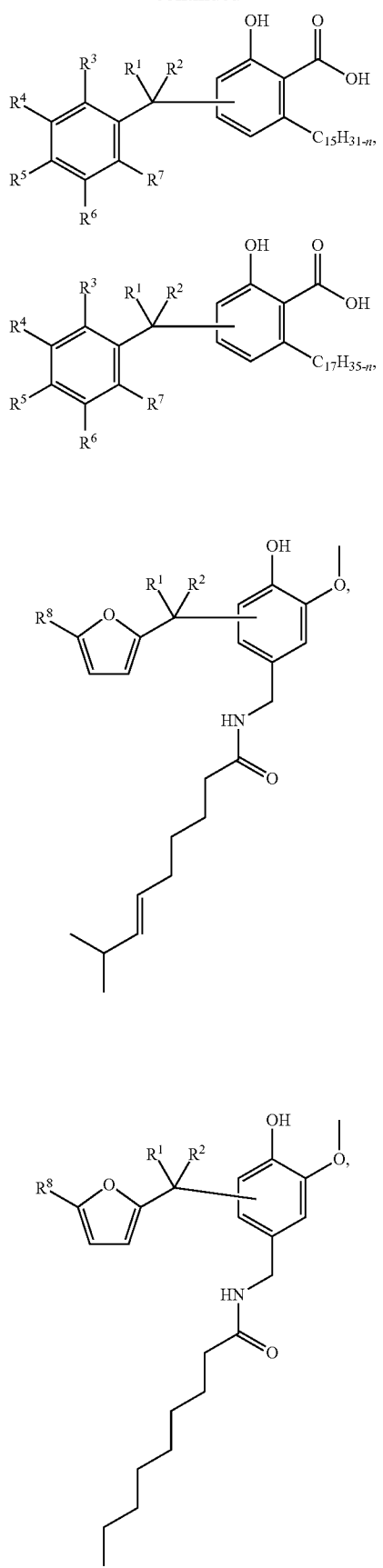

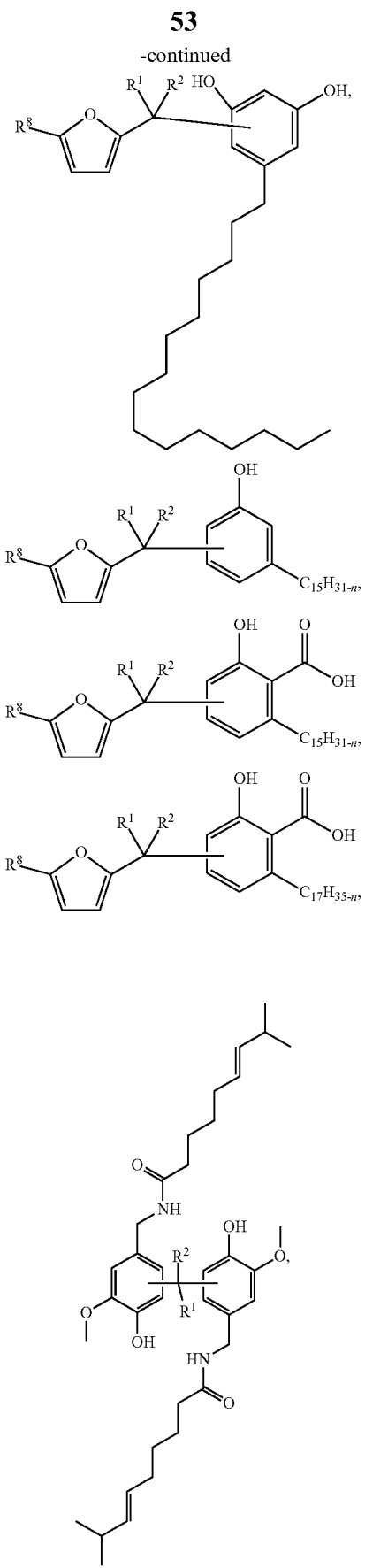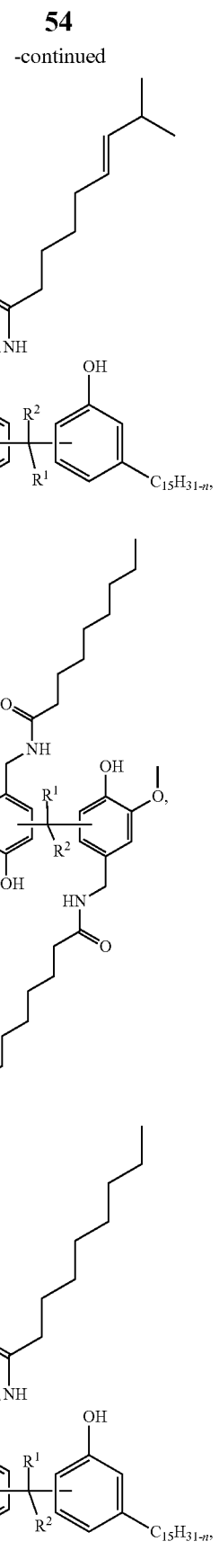

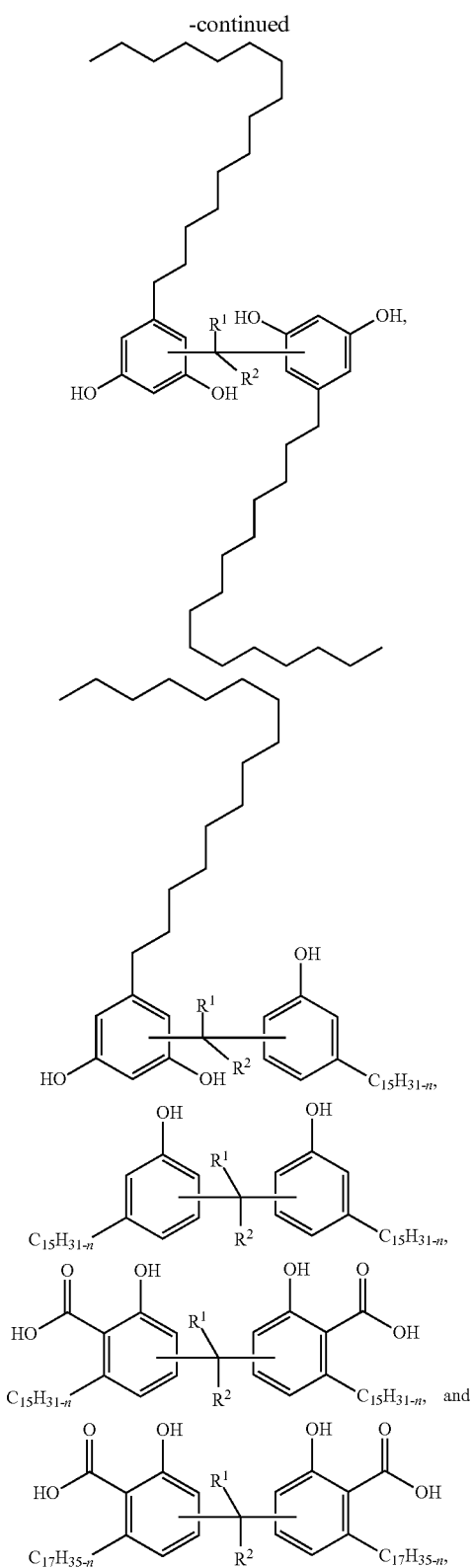

or a salt or solvate thereof.

The compound of Formula (V) can be prepared by coupling benzene- or furan-based monomers with cardanol, capsaicin and/or synthetic capsaicin, or analogues or derivatives thereof.

In certain embodiments, the benzene- or furan-based monomer comprises a α-hydroxy-methyl substituent, wherein at least one selected from the group consisting of $R^3$-$R^7$ is —OH, such as:

Such monomer can be coupled with cardanol, capsaicin, and/or synthetic capsaicin, or analogues or derivatives thereof. For this reaction, the α-hydroxymethyl starting materials can undergo unwanted self-coupling, and to prevent (or minimize) this unwanted reaction an excess of cardanol/capsaicin is used. Non-limiting examples of α-hydroxy-methyl phenolic/furanic monomers contemplated within the invention include gastrodigenin, vanillyl alcohol, syringol alcohol, and furfuryl alcohol.

In certain embodiments, the benzene-based or furan-based monomer does not comprise an α-hydroxy-methyl substituent, and an aldehyde or ketone (such as, but not limited to, formaldehyde, paraformaldehyde, or acetone) is used as a coupling agent, being incorporated in the final product. Non-limiting examples of such phenolic-containing monomers contemplated within the invention include, but are not limited to, phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, carvacrol, thymol, eugenol, crocin, gallic acid, cardanol, capsaicin, quercetin, kaemferol, catechin, and so forth. For example, two molecules of cardanol (or two molecules of capsaicin) can be coupled to form a bis-conjugated compound, using formaldehyde, paraformaldehyde, or acetone as a coupling agent. A large excess of the phenolic compound is generally used to result in bis-conjugated products rather than oligo-conjugated products.

In certain embodiments, at least one occurrence of $R^3$-$R^7$ is H. In other embodiments, at least two occurrences of $R^3$-$R^7$ are H. In yet other embodiments, at least three occurrences of $R^3$-$R^7$ are H. In yet other embodiments, at least four occurrences of $R^3$-$R^7$ are H.

In certain embodiments, $R^1$ and $R^2$ are H. In other embodiments, $R^1$ and $R^2$ are methyl. In yet other embodiments, $R^1$ is H and $R^2$ is methyl. In yet other embodiments, $R^1$ and $R^2$ combine so as to form =O.

In certain embodiments, the method to prepare a compound of Formula (V) comprises contacting the at least one α-hydroxy methyl phenol/furan, a phenolic monomer, and an acid catalyst. The ratio of phenolic monomer to α-hydroxy methyl phenol/furan is nominally 1:1, but generally higher than that (for example 3:1) to maximize formation of compound of Formula (V). In a non-limiting example, the phenolic monomer is mixed with the α-hydroxy methyl phenol/furan, and the mixture is then heated to about 60-65° C. for about 2 hours. Then, an acid catalyst is added slowly, and the reaction is allowed to progress for about 24 hours. In an exemplary case, where a solid acid catalyst is utilized (such as AMBERLYST 15 hydrogen form or DOWEX DR-2030 hydrogen form), the reaction mixture is diluted in an organic solvent, and subsequently filtered to remove the catalyst. The mixture is then concentrated under reduced pressure and purified via chromatography.

In certain embodiments, a compound of Formula (V) can be prepared using a cardanol- or capsaicin-related compound, along with an aldehyde or ketone such as, for example, formaldehyde, paraformaldehyde, or acetone. Non-limiting examples of cardanol- or capsaicin-related compounds contemplated within the invention include cardanol, cardol, anacardic acid, and capsaicin, as well as derivatives thereof, such as derivatives of the (poly)alkenyl groups of the corresponding side chain, such as partially or fully metathesized, partially or fully hydrogenated, partially or fully epoxidized, and/or partially or fully hydroxylated derivatives thereof. In this case, $R^4$ and $R^5$ are independently selected from the group consisting of H and $C_1$-$C_2$ alkyl, or $R^4$ and $R^5$ combine so as to form =O.

In certain embodiments, the compound of the invention comprises Formula (VI), or a salt or solvate thereof:

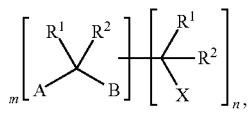

(VI)

m is an integer ranging from 1 to 2, wherein if m is equal to 2, then each

unit is covalently linked to another

unit through a —C($R^1$)($R^2$)— bond;

n is an integer ranging from 0 to 2;

X is A or B;

each occurrence of $R^1$ and $R^2$ are independently selected from the group consisting of H and $C_1$-$C_{12}$ alkyl (such as but not limited to —$CH_3$ and —$CH_2CH_3$), or $R^1$ and $R^2$ bound to the same carbon combine to form =O;

each ring A is independently selected from the group consisting of:

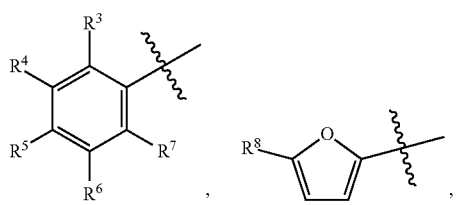

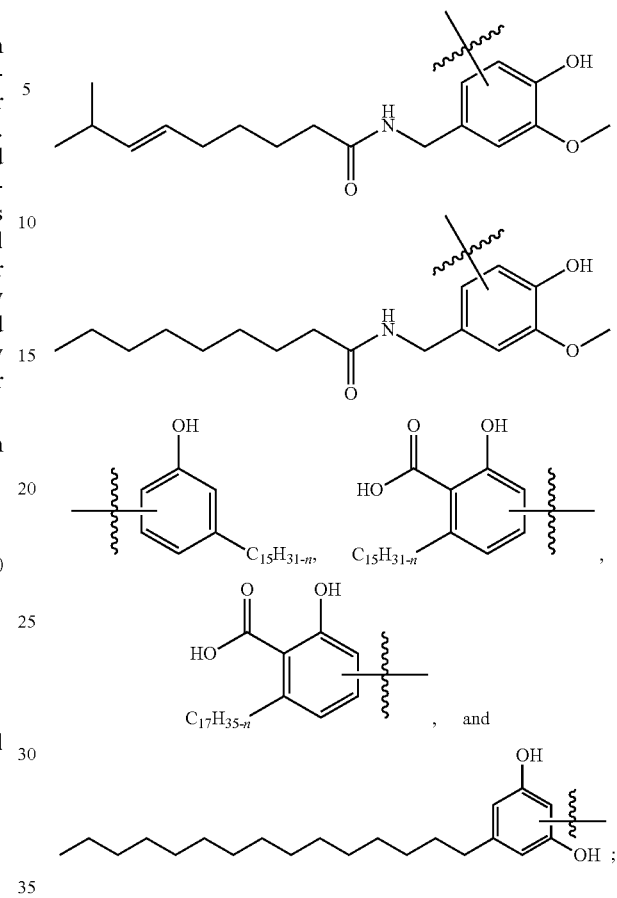

each ring B is independently selected from the group consisting of:

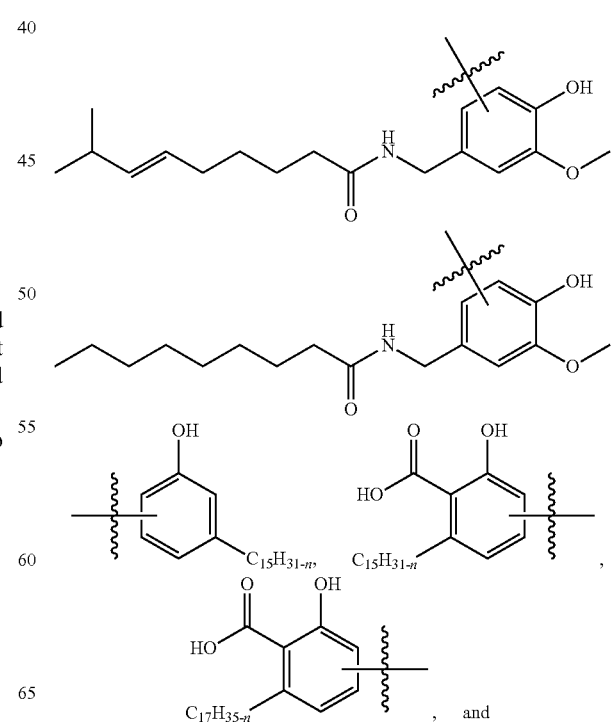

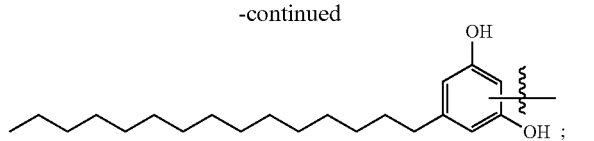

each occurrence of n is independently selected from the group consisting of 0, 2, 4, and 6;

each one of $R^3$-$R^7$ is independently selected from the group consisting of H, —OH, hydroxymethyl, $C_1$-$C_{20}$ alkyl, $C_1$-$C_6$ alkoxy (such as, but not limited to, methyl ether, ethyl ether, n-propyl ether, isopropyl ether, n-butyl ether, isobutyl ether, t-butyl ether, sec-butyl ether and so forth), $C_1$-$C_6$ acyloxy (such as, but not limited to, formyloxy, acetoxy, propionoxy, acryloyloxy, and methacryloyloxy), halogen, —$NH_2$, furyl, benzyl, substituted furyl and substituted benzyl, wherein at least one selected from the group consisting of $R^3$-$R^7$ is —OH; and $R^8$ is selected from the group consisting of H, —$CH_2OH$, —$CH_2O(C_1$-$C_6$ alkyl), —$CH_2$(halogen), —$CH_2NH_2$, $C_1$-$C_{20}$ alkyl, $C_1$-$C_6$ alkoxy, $C_1$-$C_6$ acyloxy, furyl, benzyl, substituted furyl, and substituted benzyl.

In certain embodiments, m=1, n=1, X=A, and the compound of Formula (VI) comprises a structure selected from the group consisting of:

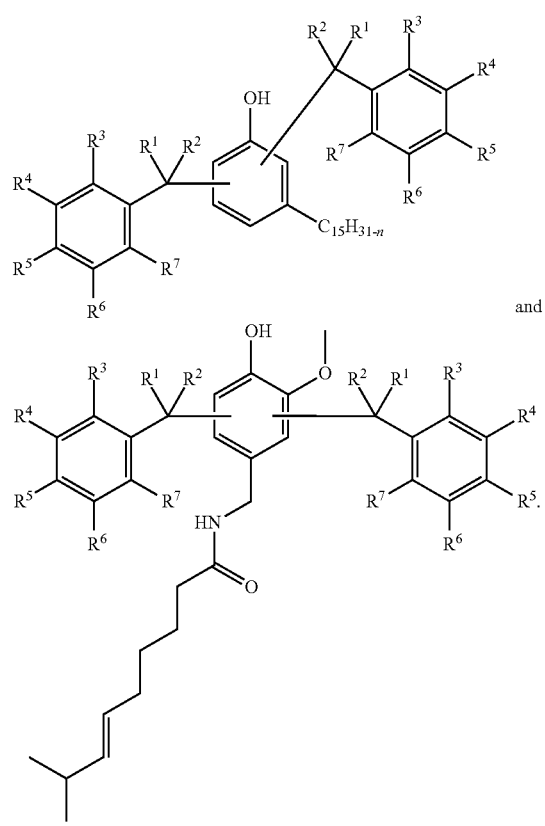

In certain embodiments, m=1, n=1, X=A, and the compound of Formula (VI) is selected from the group consisting of:

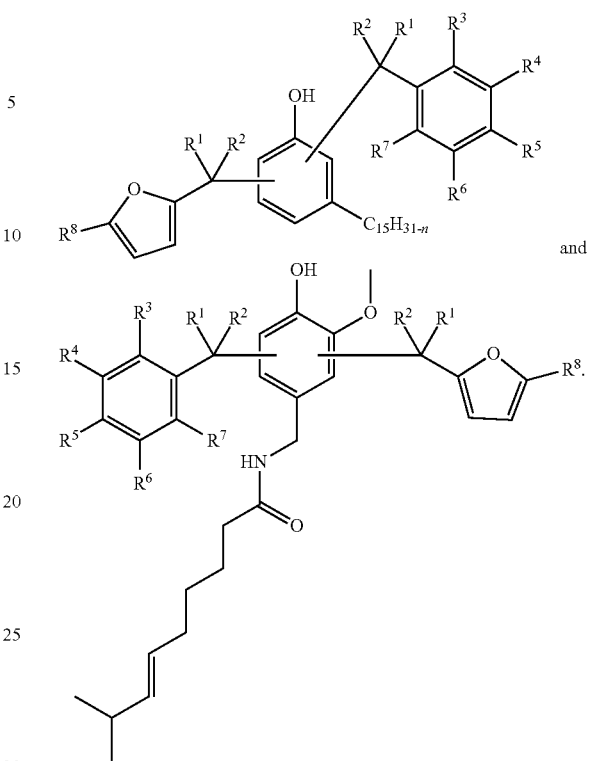

In certain embodiments, compounds of Formula (V) are self-coupled using as coupling agents an aldehyde, such as formaldehyde and paraformaldehyde, or a ketone, such as acetone, to produce a compounds of Formula (VI) wherein m=2 and n=0.

In certain embodiment, compounds of Formula (V) are coupled with a cardanol- or capsaicin-related compound in the presence of an aldehyde (such as formaldehyde or paraformaldehyde) or ketone (such as acetone), to produce a mixture of compounds comprising Formula (VI), where X=B. The resulting compounds have a distribution of the starting monomers used to make up each molecule and in the number of aromatic units in the resulting oligomers. Non-limiting examples of cardanol- or capsaicin-related compounds include but are not limited to cardanol, cardol, and anacardic acid. Because the compound of Formula (V) comprises a cardanol- or capsaicin-related structure, each of the molecules in the resulting mixture will comprise a cardanol- or capsaicin-related structure as well. In certain embodiments, the compound of Formula (V) has available hydrogen atoms on the phenyl/furan ring. In an example, the compound of Formula (V), cardanol- or capsaicin-related compound, and the aldehyde or ketone are mixed and heated to 60-65° C. for 2 hours. Then, an acid catalyst is added slowly, and the reaction is allowed to progress for 24 hours. In an exemplary case where a solid acid catalyst is utilized (such as AMBERLYST 15 hydrogen form or DOWEX DR-2030 hydrogen form), the reaction mixture is diluted in an organic solvent and subsequently filtered to remove the catalyst. The mixture is then concentrated under reduced pressure and purified via chromatography. This method produces a distribution of oligomerized compounds, all of which containing cardanol and/or capsaicin derivatives.

In certain embodiments, compounds of Formula (V) are coupled with phenolic-containing compounds, including polyphenols and novolacs, to produce a mixture of compounds comprising Formula (VI), where X=A. Non-limiting examples of phenolic-containing compounds contemplated within the invention include, but are not limited to, phenol, vanillyl alcohol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), gastrodigenin, hydroquinone, 4-methoxyphenol, carvacrol, thymol, eugenol, crocin, gallic acid, cardanol, capsaicin, quercetin, kaemferol, catechin, and so forth. In an example, the compound of Formula (V), the phenolic-containing compound, and an aldehyde or ketone are mixed and heated to about 60-65° C. for about 2 hours. Then, an acid catalyst is added slowly, and the reaction is allowed to progress for about 24 hours. In an exemplary case where a solid acid catalyst is utilized (such as AMBERLYST 15 hydrogen form or DOWEX DR-2030 hydrogen form), the reaction mixture is diluted in an organic solvent, and subsequently filtered to remove the catalyst. The mixture is then concentrated under reduced pressure and purified via chromatography. This method results in a distribution of products where some products contain the phenolic-containing compound coupled to Formula (V), some unreacted compound of Formula (V), and some oligomerized phenolic-containing compounds.

In certain embodiments, compounds of Formula (V) are coupled to an α-hydroxymethyl-phenol or α-hydroxymethyl-furan to generate a compound of Formula (VI). To minimize its self-coupling, the α-hydroxymethyl-phenol or α-hydroxymethyl-furan is added in limiting amounts and in aliquots. Higher molecules weight species are separated using distillation or chromatography. In an example, the reagents are mixed and heated to 60-65° C. for 2 hours. Then, an acid catalyst is added slowly, and the reaction is allowed to progress for 24 hours. In an exemplary case where a solid acid catalyst is utilized (such as AMBERLYST 15 hydrogen form or DOWEX DR-2030 hydrogen form), the reaction mixture is diluted in an organic solvent, and subsequently filtered to remove the catalyst. The mixture is then concentrated under reduced pressure and purified via chromatography. This method produces a distribution of molecules where not all molecules in the mixture contain cardanol- or capsaicin-related structures. The resulting reaction mixture comprises a distribution of compounds, including compounds of Formula (VI), compounds of Formula (V) and oligomers of the α-hydroxymethyl-phenol or α-hydroxymethyl-furan.

In certain embodiments, compounds of Formula (V) are coupled to an aldehyde or ketone (X=A). In an example, the compound of Formula (V) is mixed with the aldehyde or ketone, and the mixture is then heated to 60-65° C. for 2 hours. Then, an acid catalyst is added slowly, and the reaction is allowed to progress for 24 hours. In an exemplary case where a solid acid catalyst is utilized (such as AMBERLYST 15 hydrogen form or DOWEX DR-2030 hydrogen form), the reaction mixture is diluted in an organic solvent, and subsequently filtered to remove the catalyst. The mixture is then concentrated under reduced pressure and purified via chromatography. This method produces a distribution of oligomerized compounds, all of which containing cardanol- or capsaicin-related structures.

Figure 7:
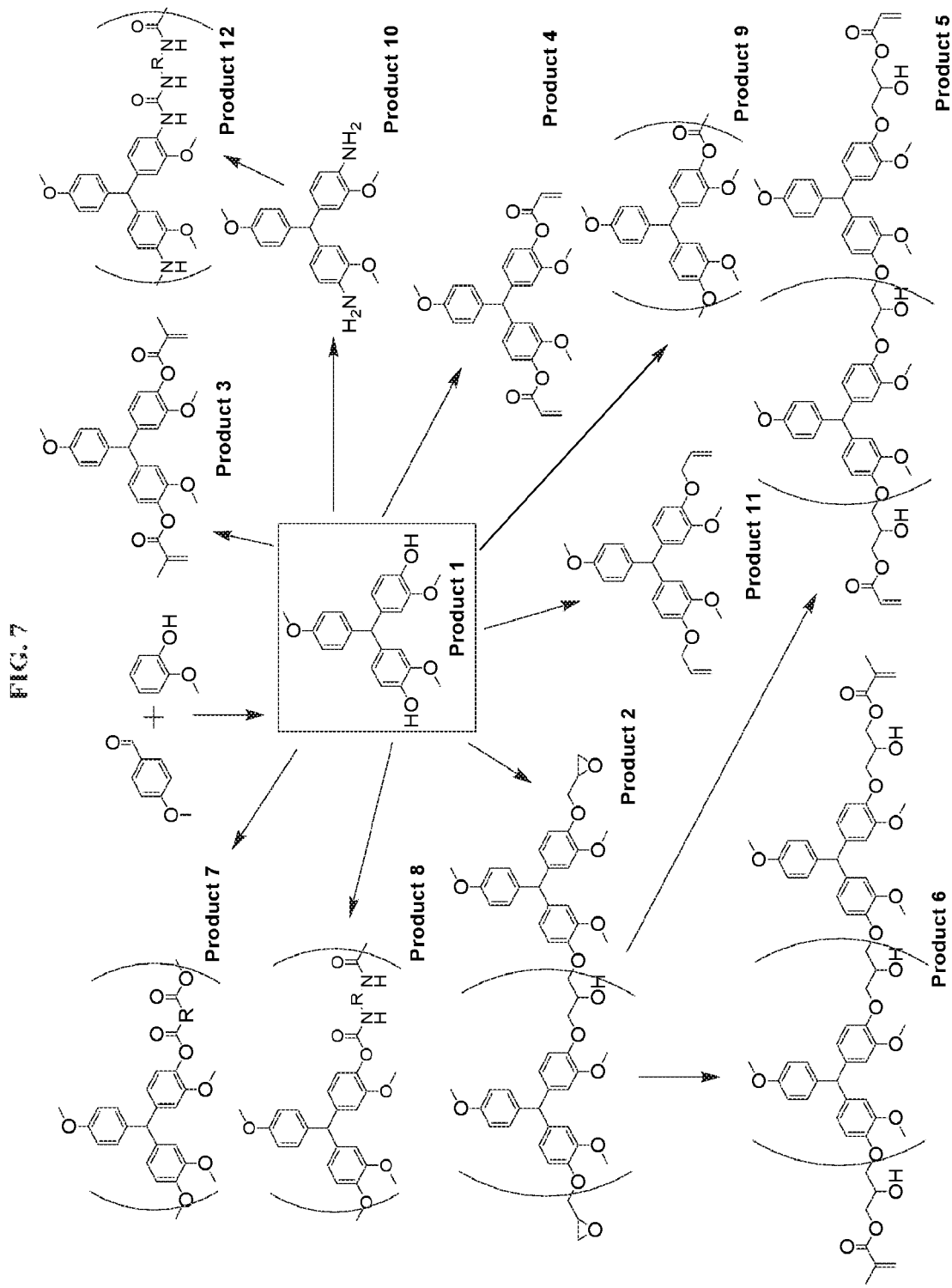
FIG. 7 illustrates non-limiting examples of compounds contemplated within the invention.
Figure 8:
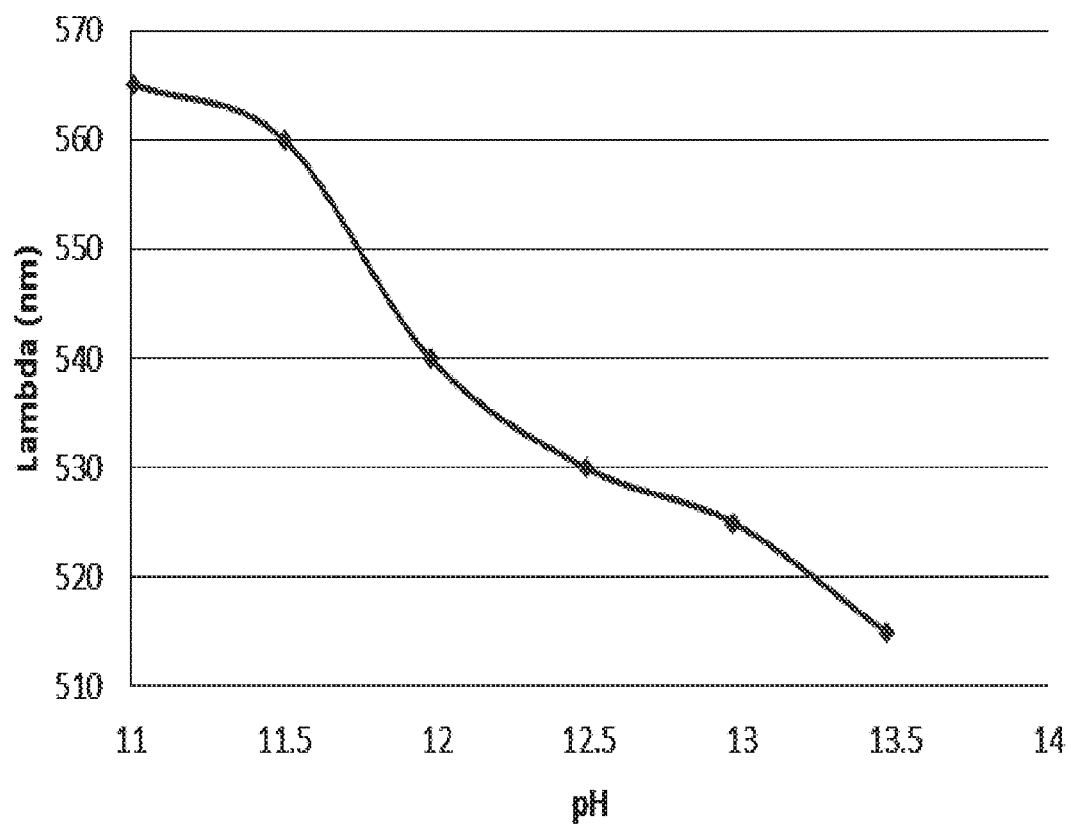
FIG. 8 comprises a graph illustrating maximum absorbance as a function of pH for a compound of the invention.
Figure 9:
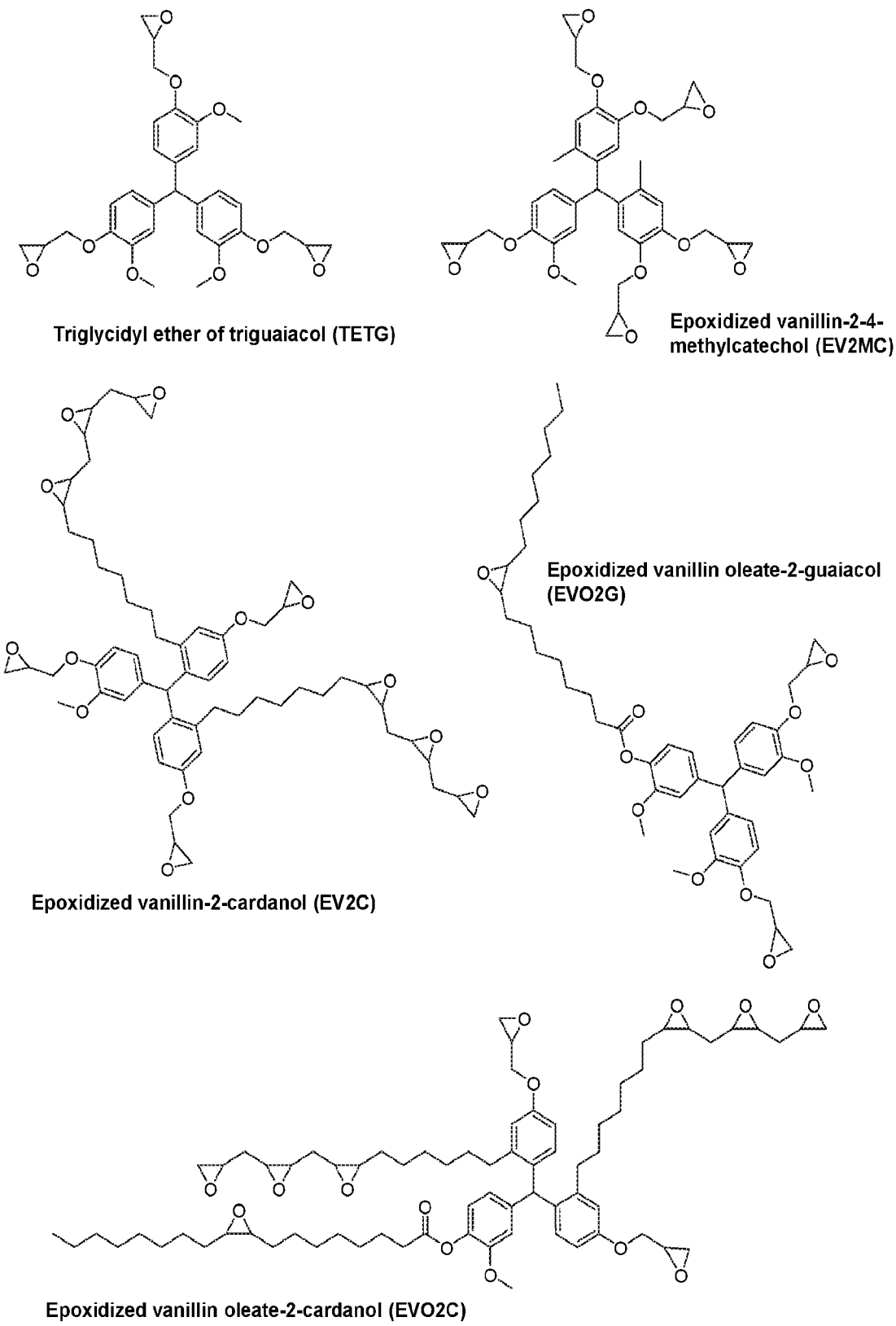
FIG. 9 comprises illustrative compounds of the invention.

The invention further provides compounds that can be prepared from other compounds contemplated herein, such as but not limited to compounds of Formula (Ia)-(Ie) or (II). FIG. 7 illustrates such compounds, including epoxides, (meth)acrylates, vinyl esters, amines, and any combinations of thereof. In FIG. 7, n can be independently 0 (except where not applicable), 1, 2, 3, 4, 5, 6, 7, 8, 9, 10, 11, 12, 13, 14, 15, 16, 17, 18, 19, 20, 21, 22, 23, or 24. Procedures recited herein are exemplified with Product 1, but are not limited to this compound, but rather can be applied to any compound contemplated within the invention. Product 1 is used as a non-limiting example. identity of products formed can be confirmed using physical methods known in the art, such as but not limited to NMR ($^1$H and/or $^{13}$C), IR spectroscopy, UV-vis spectroscopy, and so forth.

Diglycidyl ethers of phenolic compounds (Product 2) can be synthesized via reaction of Product 1 with epichlorohydrin and a base, which can be an alkali base, for example, sodium hydroxide or potassium hydroxide. The number of monomeric units in Formula 2 can range from 1 to 24 (n=0-23), or from 1 to 10 (n=0-9), or from 1 to 5 (n=0-4), or from 1 to 3 (n=0-2), or can be 1 (n=0). In certain embodiments, synthesis of the diglycidyl ethers is carried out using at least two equivalents of epichlorohydrin (in certain embodiments, 10 or 30 equivalents) to minimize oligomerization and thereby produce epoxies with average n values less than 1, and using at least two stoichiometric equivalents of base (in certain embodiments, 3-6) for every equivalent of Product 1. The reaction of a phenolic with epichlorohydrin can be catalyzed by a phase transfer catalyst, which can be a quaternary ammonium salt (for example, n-butyl ammonium bromide), in certain embodiments at a concentration of 10-11 mol % of Product 1. Synthesis of diglycidyl ether of Product 1 involves mixing Product 1 with epichlorohydrin at 15-60° C. (in certain embodiments 20-25° C.), followed by addition of the alkali base at 0-10° C. (in certain embodiments 0-5° C.). The epoxidized product is recovered from the reaction mixture, after being subjected to aqueous washes to remove salts and distillation to remove epichlorohydrin. The presence of epoxide groups is confirmed by detecting the presence of characteristic epoxide peaks in NMR and near-IR. Epoxide equivalent weight titration as described in ASTM D-1652 (which is incorporated herein in its entirety) is used to determine the average molecular weight per epoxide group.

Any phenolic/aniline compound of Formula (Ia), (Ib), (Ic), (Id), (Ie) or (II) can be functionalized to a (meth) acrylated/acrylated phenolic/aniline-containing compound, which can then undergo free radical polymerization. The invention contemplates using any of the structures described herein, as well as any other compounds derived from the coupling of mono-aldehydes (such as 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, and any ester or ether thereof) with a phenolic compound (such as phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, and any ester or ether thereof). Product 3 is formed through the esterification of Product 1 using either methacryloyl chloride or methacrylic anhydride and a basic catalyst (for example, 4-(dimethylamino)pyridine and/or triethylamine) in an aprotic solvent (for example, dichloromethane and/or tetrahydrofuran). Reaction temperatures can be for example 20-80° C. (in certain embodiments 25-55° C.).

Synthesis of Product 4 can be carried out using similar methodology utilizing acryloyl chloride or acrylic anhydride as the (trans)esterification agents.

Any phenolic/aniline compound of Formula (Ia), (Ib), (Ic), (Id), (Ie) or (II) with an epoxy functionality can be functionalized to at least one (meth)acrylic ester/amide, which can undergo free radical polymerization. The invention contemplates using any of the structures described herein, as well as any other compounds derived from the coupling of mono-aldehydes (such as 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, and any ester or ether thereof) with a phenolic compound (such as phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, and any ester or ether thereof). Product 2 can be converted to a (meth)acrylic ester through reaction with a slight excess of acrylic acid (yielding Product 5) or methacrylic acid (yielding Product 6) at 70-120° C. (in certain embodiments from 90-100° C.) preferably using a catalyst, such as AMC-2, triphenylphosphine and/or triphenylantimony(III), for 1-5 hours (in certain embodiments 2-3 hours). Acid number can be used to verify addition of the (meth)acrylic acid, with acid number of less than 20 being ideal. Further, NMR analysis can be used to verify that nearly two (meth)acrylates per molecule are present in Product 5 or Product 6.

Product 2 can be converted to an epoxy-(meth)acrylic ester through reaction with acrylic acid or methacrylic acid at 70-120° C. (in certain embodiments 90-100° C.), using a catalyst, such as AMC-2, triphenylphosphine and/or triphenylantimony(III), for 1-5 hours (in certain embodiments, 2-3 hours). The amount of (meth)acrylic acid used is less than the stoichiometric amount of epoxy on Product 2, in certain embodiments 25-75 mol % of the stoichiometric amount. Acid number can be used to verify addition of the (meth)acrylic acid, with acid number of less than 15 being ideal. Further, NMR analysis can be used to verify that nearly two (meth)acrylates per molecule are present in Product 2.

Amine compounds can be prepared directly through coupling of anilines. Additionally, phenolic-containing compounds can be converted to anilines through use of the Smiles re-arrangement. Product 10 can be prepared using the Smiles re-arrangement or other techniques to convert the hydroxyl group to an amine. Product 1 is combined with excess 2-chloroacetamide, potassium carbonate, potassium iodide and dimethylformamide. The reaction is conducted at about 90° C. for one hour, followed by about 150° C. for four hours. The reaction mixture is filtered to remove catalyst and concentrated under reduced pressure. The concentrated reaction mixture is then purified using flash chromatography with hexanes and ethyl acetate as co-solvents. The fractions are then concentrated under reduced pressure.

Any phenolic/aniline compound of Formula (Ia), (Ib), (Ic), (Id), (Ie) or (II) can be functionalized with an allyl ether on at least one of the phenolic/aniline groups, and that derivative can undergo thiol-ene polymerization. The invention contemplates using any of the structures described herein, as well as any other compounds derived from the coupling of mono-aldehydes (such as 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, and any ester or ether thereof) with a phenolic compound (such as phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, and any ester or ether thereof). Product 1 can be converted into an allyl ether-containing compound (Product 11), through reaction with allyl bromide at about 50° C. using triethylbenzyl ammonium chloride and sodium hydroxide for about 5-24 hours. The reaction mixture can then be extracted with a solvent, for example pentane, washed with a brine solution, and concentrated under reduced pressure. Further purification can be carried out using chromatography.

The compounds of the invention can be used as components of a polymerizable composition, which can be polymerized to provide a polymerized material. Polymerization to make a variety of polymers can be performed using known chemical procedures. Those procedures are described below to illustrate potential derivatives that can be made from the compounds of this invention using known procedures.

Product 2 can be reacted with curing agents such as diamines to create a cross linked polymer network. Reaction of Product 2 with a diamine, for example 4,4'-diaminodicyclohexylmethane (in certain embodiments, at stoichiometric equivalents based on epoxide equivalent weight and amine hydrogen equivalent weight—52.5 g/eq if 4,4'-diaminodicyclohexylmethane) can be carried out at about 100-250° C. (in certain embodiments, about 160-180° C.) with a step curing procedure. The extent of cure can be determined via the ratio of epoxy and amine peaks in Near-IR spectra both before and after curing. The glass transition temperature ($T_g$) of the epoxy resin can be determined via DSC. These diepoxides can also be cured with acid anhydrides in stoichiometric equivalents, creating ester linkages.

In certain embodiments, the reaction used to form the epoxy thermoset involves at least one epoxy curing agent. Suitable curing agents for epoxies are well known in the industry. Non-limiting examples include aliphatic polyamines such as diethylenetriamine (DETA), triethylenetetramine (TETA), tetraethylenepentamine (TEPA), diproprenediamine (DPDA), dimethylaminopropylamine (DEAPA); alicyclic polyamines such as N-aminoethylpiperazine (N-AEP), menthane diamine (MDA), isophoronediamine (IPDA); aliphatic aromatic amines such as m-xylenediamine (m-XDA); aromatic amines such as metaphenylene diamine (MPDA), diaminodiphenylmethane (DDM), diaminodiphenylsulfone (DDS); and mixtures thereof. Further examples of suitable curing agent include EPIKURE® Curing Agent W, AMICURE® PACM/bis-(p-aminocyclohexyl)methane. Other curing agents include nadic methyl anhydride, phthalic anhydride dicyandiamide, nadic anhydride, and dicyandiamide. These curing agents are added to epoxy resins at amounts typically at or near stoichiometry, although off-stoichiometry amounts can be useful for the creation of prepregs. Epoxy homopolymerization catalysts, for example tertiary amines such as such as benzyl dimethylamine, can also cure these epoxy resins when added in catalytic amounts, typically up to 5 wt %. All of the epoxy resins are cured by ambient, thermal, induction, electron beam, UV cure or other such standard methods whereby energy is provided to initiate the reaction between the epoxy and the curing agent/catalyst. Post-cure is typically necessary because the rate of cure slows severely upon vitrification.

Product 1 can be converted to Product 3 or Product 4 to produce (meth)acrylated and acrylated phenolics, respectively, that are capable of free radical polymerization. Product 3 and Product 4 can be formed through the esterification of Product 1 as described elsewhere herein.

Any phenolic/aniline compound of Formula (Ia), (Ib), (Ic), (Id), (Ie) or (II) can be functionalized to a polyester or unsaturated polyester, which can undergo free radical polymerization. The invention contemplates using any of the structures described herein, as well as any other compounds derived from the coupling of mono-aldehydes (such as 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, and any ester or ether thereof) with a phenolic compound (such as phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, and any ester or ether thereof). Product 7 can be synthesized under conditions that can result in formation of polyester or unsaturated polyester resins (UPE)s depending on the reaction composition. Product 1 is melted together in the presence or absence of another diol or polyol moiety, for example diethylene glycol, isosorbide, and/or propylene glycol, with a single or mixture of organic diacids, for example maleic anhydride, phthalic anhydride, terephthalic acid and/or adipic acid. The reaction is catalyzed using an acid catalyst, for example p-toluenesulfonic acid, AMBERLYST 15 hydrogen form, and/or DOWEX DR-2030 hydrogen form, and can be done in the presence or absence of an azeotropic solvent, for example toluene and/or xylenes (which aid in water removal). The reaction temperature can be carried out at about 55-220° C. (in certain embodiments, 125-180° C.). NMR analysis can be used to identify formation of polymeric material, based on the components in the starting reaction mixture. GPC analysis can be used to show formation of polymeric material with molecular weights greater than 2,000 g/mol, greater than 500 g/mol, and/or 1,500-3,000 g/mol.

Any phenolic/aniline compound of Formula (Ia), (Ib), (Ic), (Id), (Ie) or (II) can be functionalized to an isocyanate, polyisocyanate and/or poluyurethane. The invention contemplates using any of the structures described herein, as well as any other compounds derived from the coupling of mono-aldehydes (such as 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, and any ester or ether thereof) with a phenolic compound (such as phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, and any ester or ether thereof). Product 8 can be synthesized using Product 1 in combination with various di-isocyanates, poly-isocyanates and/or polyurethanes to form prepolymeric oligomers or high molecular weight polymers, depending on stoichiometric ratios. Product 1 is dissolved in solvent, for example tetrahydrofuran, chloroform, and/or diethyl ether, with a multifunctional isocyanate, for example toluene diisocyanate, hexamethylene diisocyanate, methylene diphenyl diisocyanate, and/or isophorone diisocyanate, before adding a catalytic amount of organic base, for example triethylamine, pyridine, a/or 1,8-diazabicyclo[5.4.0]undec-7-ene (DBU), typically at a concentration of 1-25 mol % (in certain embodiments, 515 mol %). Selected ratios of reagents for synthesis of Product 8 include 25-75 mol % Product 1 and 25-75 mol % diisocyanate; and 33-67 mol % Product 1 and 33-67 mol % di-isocyanate. The reaction temperature can be about 0-125° C. (in certain embodiments, about 25-80° C.). Molecular weight of the product can be, for example, greater than 8,000 g/mol, greater than 12,000 g/mol, and/or 1,500-9,000 g/mol.

Any phenolic/aniline compound of Formula (Ia), (Ib), (Ic), (Id), (Ie) or (II) can be polymerized into a polycarbonate. The invention contemplates using any of the structures described herein, as well as any other compounds derived from the coupling of mono-aldehydes (such as 3,4-dihydroxy-benzaldehyde, vanillin (4-hydroxy-3-methoxy-benzaldehyde), 4-formyl-2-hydroxy-phenol, 4-formyl-2-methoxy-phenol, 3,4,5-trihydroxybenzaldehyde, and any ester or ether thereof) with a phenolic compound (such as phenol, catechol (1,2-dihydroxybenzene), resorcinol, 4-methylcathecol, guaiacol (2-methoxy-phenol), 1,2,3-trihydroxy-phenol (pyrogallol), syringol (1,3-dimethoxy-2-hydroxy-benzene), hydroquinone, 4-methoxyphenol, and any ester or ether thereof). Product 9 can be synthesized by treating Product 1 with phosgene or phosgene derivatives, and/or of p-nitrophenyl chloroformate or other chloroformates. Product 1 can be dissolved in a solvent, for example 1,4-dioxane, acetonitrile and/or dichloromethane. In the case of liquid of solid co-reactants, the co-reactant can be dissolved in a solvent, for example 1,4-dioxane, acetonitrile, and/or dichloromethane. These solutions can be added to a catalytic amount of organic base including, but not limited to pyridine, 4-(dimethylamino)pyridine, 1-methylimidazole, and/or 2-methylimidazole, in concentrations of about 0.5-10 mol % (in certain embodiments, about 1-5 mol %). A stoichiometric amounts of a second organic base, for example trimethylamine, pyridine, can also be added. Exemplary reaction temperatures are about 0-100° C. (in certain embodiments, 15-40° C.). The reaction can be conductediunder atmospheric air, but preferably under an inert atmosphere. Polymeric material can be recovered by addition of an anti-solvent, but other such techniques are possible including filtration, vacuum distillation, chromatography, and/or flash chromatography. GPC, FTIR and NMR analyses can be used to identify formation of the polymeric material without degradation of the starting compounds. In certain embodiments, polymerization is insensitive to the specific structure of Product 1 or variants thereof. In other embodiments, high molecular weight polymers can be achieved via higher purity reactants, reagents, and optimized reaction conditions. Selected number average molecular weights (measured by GPC) are greater than 12,000 g/mol, greater than 6,000 g/mol, and/or 500-12,000 g/mol. Dispersity can be 1-5, and in certain embodiments 1.5-2.5. Glass transition temperature can be in the range of 25-150° C., and in certain embodiments 75-150° C.

Product 10 can be cured with Product 2 or other epoxides, using methods for curing high temperature epoxy resins. Product 10 can also be cured with esters or anhydrides to yield polyamide and polyimides. Anhydrides such as nadic anhydride (NA) and 3,3',4,4'-benzophenonetetracarboxylic dianhydride (BTDA) can be reacted with Product 10 to yield a polyamide and polyimide. In certain embodiments, the anhydrides are charged to a reactor in pellet form, and 100 mL of methanol are added for 30.44 g of these two anhydrides. The anhydrides are heated in the methanol for about 90 min at 90° C. while in methanol, allowing them time to esterify. After heating for 90 min, the mixture is cooled to room temperature and crushed Product 10 is slowly added. The mixture is then left to stir overnight. The ratio of the anhydride functionality to the amine functionality and the anhydrides to each other controls the molecular weight formed. If thermoplastic polyimides are desired, no NA should be used and the ratio of BTDA and diamine should be approximately 1:1. For PMR type polyimides, the standard ratio of 2:2.087:3.087 for NA:BTDA:diamine mimics that used for making PMR-15. The oligomers can then be cured under high heat (250° C.) for a few hours to produce a crosslinked thermoset.

Figure 12:
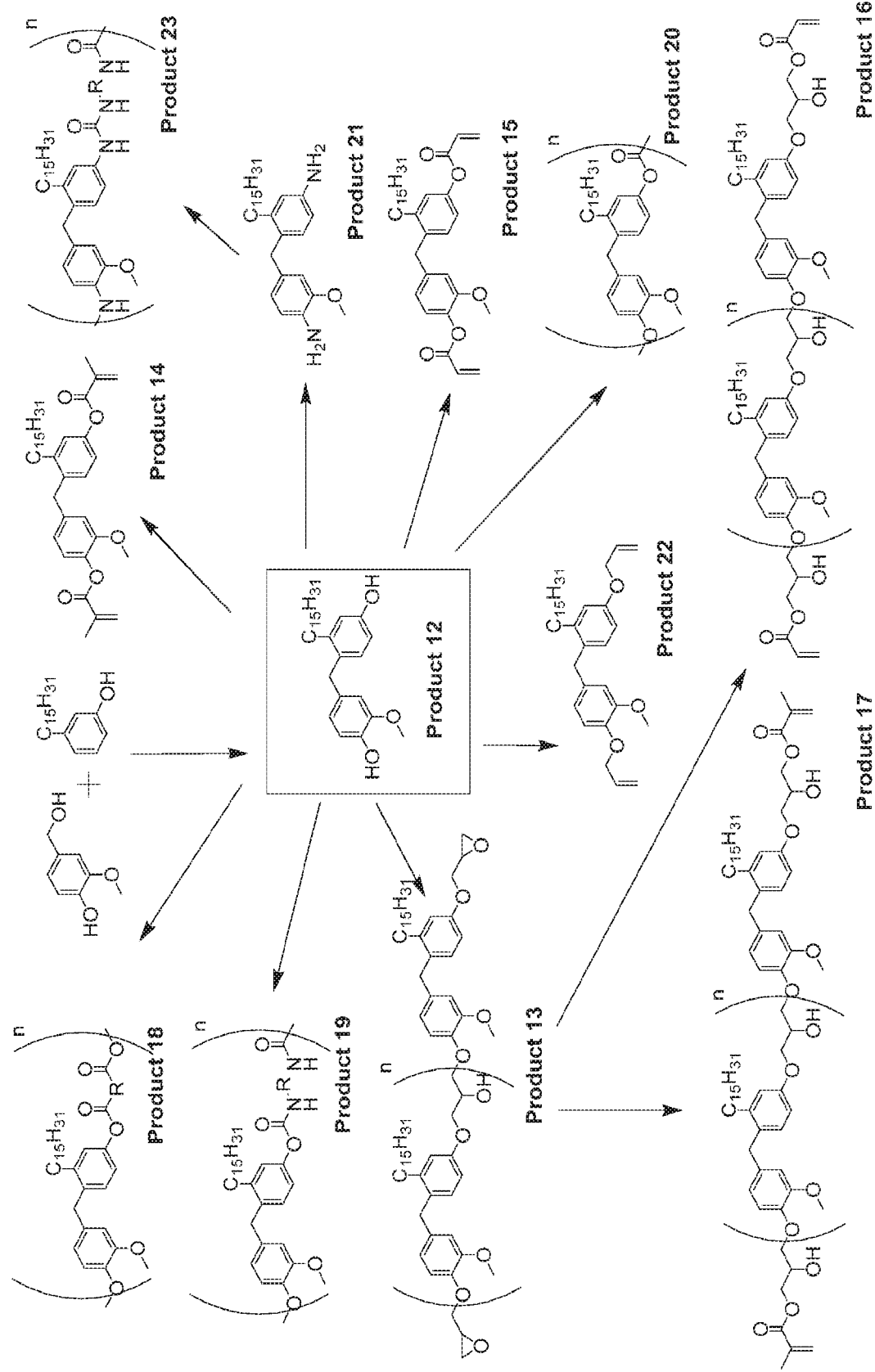
FIG. 12 comprises illustrative compounds of the invention.

In certain embodiments, a compound of the invention can be converted to other monomers, such as, but not limited to, epoxides, methacrylates, vinyl esters, amines, and combinations thereof, as illustrated in FIG. 12.

Diglycidyl ethers of phenolic compounds (Product 13) can be synthesized by reacting Product 12 with epichlorohydrin and a base, which can be an alkali salt base, for example sodium hydroxide or potassium hydroxide. The value of n can range from 0 to 24, or from 0 to 10, or from 0 to 5, or from 0 to 3, or from 0 to 1. In certain embodiments, synthesis of these diglycidyl ethers is carried out with at least two equivalents of epichlorohydrin (preferably 10 or 30 equivalents) to minimize oligomerization, thus producing epoxides with average n values less than 1, and with at least two stoichiometric equivalents of base (preferably 3-6) for every equivalent of Product 12. The reaction of a phenol with epichlorohydrin can be catalyzed by a phase transfer catalyst, which can be a quaternary ammonium salt (for example, n-butyl ammonium bromide), preferably at a concentration of 10-11 mol % of the phenol. Synthesis of diglycidyl ether of the phenolic involves mixing the phenol with epichlorohydrin at 15-60° C., in certain embodiments 20-25° C., followed by addition of the alkali base at 0-10° C., in certain embodiments 0-5° C. The epoxide product is recovered from the reaction mixture after aqueous washes to remove salts, and is subjected to distillation to remove epichlorohydrin. Addition of epoxide groups is confirmed based on the presence of characteristic epoxide peaks in NMR and near-IR spectra. Epoxide equivalent weight titration as described in ASTM D-1652 is used to determine the average molecular weight per epoxide group.

Phenols can be functionalized through various methods and converted to produce methacrylated and acrylated phenolics that are capable of free radical polymerization. Product 14 is formed through the esterification of Product 12 using for example methacryloyl chloride or methacrylic anhydride and a base catalyst (for example 4-(dimethylamino)pyridine and triethylamine) in an aprotic solvent (for example dichloromethane or tetrahydrofuran). Reaction temperatures occur in certain embodiments 20-80° C., in other embodiments at 25-55° C.

Synthesis of Product 15 can be carried out using similar methodology utilizing acryloyl chloride or acrylic anhydride as the (trans)esterification agents. Identity of products can be ascertained by NMR analysis. Product 13 can be converted to a (meth)acrylic ester through reaction with a slight excess of acrylic acid (Product 16) or methacrylic acid (Product 17) at 70-120° C., in certain embodiments 90-100° C., in some cases using a catalyst, such as AMC-2, triphenylphosphine, or triphenylantimony(III), for 1-5 hours, in certain embodiments 2-3 hours. Acid number can be used to verify addition of the (meth)acrylic acid; in certain embodiments, acid number of less than 20 is obtained. NMR analysis can be used to verify that nearly two (meth)acrylates per molecule are present.

Product 13 can be converted to an epoxy-(meth)acrylic ester through reaction with acrylic acid or methacrylic acid at 70-120° C., in certain embodiments 90-100° C., using a catalyst, such as AMC-2, triphenylphosphine, or triphenylantimony(III), for 1-5 hours, in certain embodiments 2-3 hours. The amount of (meth)acrylic acid used is less than the stoichiometric amount of epoxy on Product 13, in certain embodiments 25-75 mol % of the stoichiometric amount. Acid number can be used to verify addition of the (meth)acrylic acid; in certain embodiments, acid number of less than 15 is observed. NMR analysis can be used to verify the number of (meth)acrylates and epoxides per molecule present.

Phenols can be converted to anilines through use of the Smiles re-arrangement. Product 21 can be prepared using the Smiles re-arrangement, or any other applicable reaction, to convert the hydroxyl group to an amine. Product 12 is combined with excess 2-chloroacetamide, potassium carbonate, potassium iodide and dimethylformamide. For example, the reaction is conducted at 90° C. for 1 hour followed by 150° C. for 4 hours. The reaction mixture is filtered to remove catalyst and concentrated under reduced pressure. The concentrated reaction mixture is then purified using flash chromatography with hexanes and ethyl acetate as co-solvents. The fractions are then concentrated under reduced pressure.

Product 12 can be converted into an allyl ether bearing molecule (Product 22), through reaction with allyl bromide at 50° C. using triethylbenzyl ammonium chloride and sodium hydroxide for 5-24 hours. The reaction mixture can then be extracted with a solvent, for example pentane, washed with a brine solution, and concentrated under reduced pressure. Further purification can be carried out using chromatography.

The compounds of the invention can be used as components of a polymerizable composition, which can be polymerized to provide a polymerized material. Polymerization to make a variety of polymers is straight forward using known chemical procedures. Those procedures are described below in non-limiting manner.

Product 13 can be reacted with curing agents such as diamines to create a cross linked polymer network. Reaction of Product 13 with a diamine, for example 4,4'-diaminodicyclohexylmethane, in certain embodiments at stoichiometric equivalents based on epoxide equivalent weight and amine hydrogen equivalent weight (52.5 g/eq in the case of 4,4'-diaminodicyclohexylmethane) can be carried out at 100-250° C., in certain embodiments 160-180° C. with a step curing procedure. The extent of cure is determined via the ratio of epoxy and amine peaks in near-IR spectra both before and after curing. The glass transition temperature ($T_g$) of the epoxy resin can be determined via DSC. These diepoxides can also be cured with acid anhydrides in stoichiometric equivalents, creating ester linkages.

In certain embodiments, the reaction used to form the epoxy thermoset also involves at least one epoxy curing agent. Suitable curing agents for epoxies are well known in the industry. Examples include: aliphatic polyamines, such as diethylenetriamine (DETA), triethylenetetramine (TETA), tetraethylenepentamine (TEPA), diproprenediamine (DPDA), and dimethylamino propylamine (DEAPA); alicyclic polyamines, such as N-aminoethylpiperazine (N-AEP), menthane diamine (MDA), and isophoronediamine (IPDA); aliphatic aromatic amines, such as m-xylenediamine (m-XDA); aromatic amines, such as metaphenylene diamine (MPDA), diaminodiphenylmethane (DDM), and diaminodiphenylsulfone (DDS); and mixtures thereof. Further examples of suitable curing agent include EPI-KURE® Curing Agent W, and AMICURE® PACM/bis-(p-aminocyclohexyl)methane. Other curing agents include nadic methyl anhydride, phthalic anhydride dicyandiamide, nadic anhydride, and dicyandiamide. These curing agents are added to epoxy resins at amounts typically at or near stoichiometry, although off-stoichiometry amounts can be useful for the creation of prepregs. Epoxy homopolymerization catalysts, for example tertiary amines such as such as benzyl dimethylamine, can also cure these epoxy resins when added in catalytic amounts, typically up to 5 wt %. All of the epoxy resins are cured by ambient, thermal, induction, electron beam, UV cure or other such standard methods whereby energy is provided to initiate the reaction between the epoxy and the curing agent/catalyst. Post-cure is typically necessary because the rate of cure slows severely upon vitrification.

Product 12 can be functionalized through a number of methods and converted to Product 14 or Product 15 to produce methacrylated and acrylated phenols, respectively, that are capable of undergoing free radical polymerization. Product 14 is formed through the esterification of Product 12 using either methacryloyl chloride or methacrylic anhydride and a base catalyst (for example 4-(dimethylamino)pyridine and triethylamine) in an aprotic solvent (for example, dichloromethane and tetrahydrofuran). Reaction temperatures occur at about 20-80° C., in certain embodiments at 25-55° C. The synthesis of Product 15 can be carried out using similar methodology utilizing acryloyl chloride or acrylic anhydride as the (trans)esterification agents. Reaction progression can be monitored using NMR analysis.

Product 18 can be synthesized under conditions that can result in the formation of polyester or unsaturated polyester (UPE) resins, depending on the reaction composition and/or conditions. Product 12 is melted together in the presence or absence of another diol or polyol, for example diethylene glycol, isosorbide, or propylene glycol, with a single or a mixture of organic diacids, for example maleic anhydride, phthalic anhydride, terephthalic acid, or adipic acid. The reaction is catalyzed using an acid catalyst, for example p-toluenesulfonic acid, AMBERLYST 15 hydrogen form or DOWEX DR-2030 hydrogen form, and can be run in the presence or absence of an azeotropic solvent, for example toluene and xylenes, to aid in water removal. The reaction temperature can be carried out at 55-220° C., in certain embodiments 125-180° C. Reaction progression can be monitored using NMR analysis. GPC analysis can be used to identify molecular weights, which can be greater than 2,000 g/mol, and/or above 500 g/mol. In certain embodiments, molecular weights of 1,500-3,000 g/mol are obtained.

Product 19 can be synthesized using Product 12 in combination with diisocyanates or polyisocyanates to form prepolymeric oligomers or high molecular weight polymers, depending on stoichiometric ratios. Product 12 is dissolved in a solvent, for example tetrahydrofuran, chloroform, or diethyl ether, with a multifunctional isocyanate, for example toluene diisocyanate, hexamethylene diisocyanate, methylene diphenyl diisocyanate, or isophorone diisocyanate, before adding a catalytic amount of an organic base, for example triethylamine, pyridine, or 1,8-diazabicyclo[5.4.0]undec-7-ene (DBU), typically at a concentration of 1-25 mol %, in certain embodiments 5-15 mol %. Exemplary ratios for synthesis of Product 19 are 25-75 mol % Product 12 and 25-75 mol % diisocyanate, in certain embodiments a ratio of 33-67 mol % Product 12 and 33-67 mol % diisocyanate is used. The reaction temperature is about 0-125° C., in certain embodiments 25-80° C. Molecular weights can be greater than 8,000 g/mol, and/or greater than 12,000 g/mol; in certain embodiments, molecular weights of 1,500-9,000 g/mol are also obtained.

Product 20 can be synthesized using Product 12 in the presence of phosgene or phosgene derivatives, or in the presence of p-nitrophenyl chloroformate or other chloroformates. Product 12 can be dissolved in a solvent, for example 1,4-dioxane, acetonitrile, or dichloromethane. In the case of liquid or solid co-reactants, the co-reactant can be dissolved in a solvent, for example 1,4-dioxane, acetonitrile, or dichloromethane. These solutions can be added to a catalytic amount of an organic base including, but not limited to pyridine, 4-(dimethylamino)pyridine, 1-methylimidazole, or 2-methylimidazole, in concentrations of abouy 0.5-10 mol %, in certain embodiments 1-5 mol %. A stoichiometric amounts of a second organic base, for example trimethylamine or pyridine, can also be added. Exemplary reaction temperatures are 0-100° C., in certain embodiments 15-40° C. The reaction can be conducted in contact with atmospheric air, but in certain embodiments can be done under an inert atmosphere. Polymeric material can be recovered by addition of an anti-solvent, but other such techniques can be used including filtration, vacuum distillation, chromatography, and flash chromatography. GPC, FTIR and NMR analyses can be used to monitor reaction progression. Analysis of this reaction indicated that polymerization is insensitive to the specific structure of Product 12. Higher molecular weight polymers can be achieved via higher purity reactants, reagents, and optimized reaction conditions. Exemplary number average molecular weights (measured by GPC) are greater than 6,000 g/mol, 500-12,000 g/mol, and/or greater than 12,000 g/mol. A dispersity of 1-5 can be obtained; in certain embodiments, a dispersity of 1.5-2.5 is obtained. An exemplary glass transition temperature is in the range of 25-150° C., in certain embodiments 75-150° C.

Product 21 can be cured with Product 13 or other epoxides using methods for curing high temperature epoxy resins. Product 21 can also be cured with esters or anhydrides to yield polyamide and polyimides. Such anhydrides, such as nadic anhydride (NA) and 3,3',4,4'-benzophenonetetracarboxylic dianhydride (BTDA), can be reacted with Product 21 to yield a polyamide and polyimide. In a non-limiting procedure, the anhydrides are charged to a reactor in pellet form, and 100 mL of methanol are added for 30.44 g of these two anhydrides. The anhydrides are heated in the methanol for about 90 min at 90° C., allowing them time to esterify. After heating for 90 min, the mixture is cooled to room temperature, and crushed Product 21 is slowly added to it. The mixture is then left to stir overnight. The ratio of the anhydride functionality to the amine functionality, and the anhydrides to each other, controls the molecular weight formed. If thermoplastic polyimides are desired, no NA is used and the ratio of BTDA and diamine is approximately 1:1. For PMR type polyimides, the standard ratio of 2:2.087:3.087 for NA:BTDA:diamine mimics what is used for making PMR-15. The oligomers can then be cured under high heat (250° C.) for a few hours to produce a crosslinked thermoset.

The neat (meth)acrylic ester products (Products 3-6) can be treated with a free-radical initiator (for example, cumene hydroperoxide or methyl ethyl ketone peroxide) at a concentration of about 0.5-8.0 wt %, in certain embodiments 1.0-3.0 wt %, in order to induce curing of the resin to form a novel polymer. Curing of resins can be accomplished with or without a promoter, for example cobalt naphthenate or dimethyl aniline, to accelerate gel time in concentrations of about 0.10-1.5 wt %, but most preferably 0.25-0.5 wt %. Cure temperatures for resins can be about 20-85° C., in certain embodiments 25-60° C.; post-cured at about 100-250° C., in certain embodiments about 120-180° C. The novel materials have comparable properties to commercial (meth)acrylic ester derived polymers and exhibit similar stiffness, toughness and $T_g$.

The (meth)acrylated products (Products 3-6) can be blended with reactive diluents (including, but not limited to, styrene, methacrylated lauric acid, or furfuryl methacrylate) to produce novel resin systems. In certain embodiments, the composition is 30-90% wt % (meth)acrylic ester (products 3-6) and 25-50 wt % reactive diluent. These resins have low viscosities, which makes them ideal for liquid molding, composite layups and vacuum assisted resin transfer molding (VARTM) processing, as well as a wide range of other applications. These resins can be cured using a free-radical initiator, in the presence or absence of a promoter, to produce co-polymers that have properties similar to polymeric materials produced by existing commercial processes, providing equivalent stiffness, toughness and $T_g$.

UPE (Product 18) resin systems can be blended with olefinically unsaturated reactive diluents (including, but not limited to, styrene, methacrylated lauric acid, and methyl methacrylate) to produce novel resin systems where the composition is 30-90 wt % Product 18 and 10-70 wt % reactive diluent, in certain embodiments 50-75 wt % Product 18 and 25-50 wt % reactive diluent. These resins have viscosities amenable to liquid molding, composite layups, VARTM processing as well as a wide range of other applications. The blended Product 18 resin can be treated with a free-radical initiator (for example, cumene hydroperoxide or methyl ethyl ketone peroxide) at a concentration of about 0.5-8.0 wt %, in certain embodiments 1.0-3.0 wt %, in order to induce curing of the resin to form a novel thermoset polymer. Curing of resins can be accomplished with or without a promoter, for example cobalt naphthenate or dimethyl aniline, to accelerate gel time in concentrations of 0.10-1.5 wt %, in certain embodiments 0.25-0.75 wt %. Cure temperatures for these UPE resins can range from abouty 20-85° C., in certain embodiments 25-60° C.; post-cured at about 100-200° C., in certain embodiments 120-180° C.

Any of the phenolic/aniline-containing compounds of the invention, with any unsubstituted phenyl positions, can be polymerized into phenol-formaldehyde resins. Base-catalysed phenol-formaldehyde resins are made with a formaldehyde/phenol ratio of greater than one with the formaldehyde dissolved in water. This reaction is typically performed at about 70° C. to oligomerize the resin then at about 120° C. to crosslink the resins and drive off water.

Any of the compounds of the invention, and derivatives thereof, prepared and cured as discussed in the exemplary embodiments described herein, can be used to prepare thermosetting compositions, examples of which include coatings and composite materials.

Coatings made from the cured compounds and/or phenol-containing compounds of the invention can contain solvents, for example methyl ethyl ketone, acetone, and/or tert-butyl acetate, and additional additives such as fibers, clays, silicates, fillers, whiskers or other conventional fillers, reinforcing materials, including their nanometer scale analogues, pigments such as titanium dioxide, iron oxides, and/or carbon black, or corrosion inhibitors such as zinc phosphate. Typical fibers used for such composites include, but are not limited to, E-glass, S-glass, KEVLAR®, carbon fiber, and ultra-high molecular weight polyethylene. Additional additives that can be employed include flow additives, film formers, defoamers, foaming agents, coupling agents, antioxidants, stabilizers, flame retardants, reheating aids, plasticizers, flexibilizers, anti-fogging agents, nucleating agents, chopped fibers or particulates of glass, carbon and aramid, fillers, impact modifiers, antioxidants, stabilizers, crystallization aids, oxygen scavengers, mold release agents, and any combinations thereof. The coatings can be applied using various methods, for example brush, roller, or sprayer. The coatings are typically cured under ambient conditions, but can be cured under a variety of other conditions, for example oven curing at elevated temperature. The compounds of the invention, and derivatives thereof, can be cured by any of the methods and chemistries described herein.

Alternatively, high molecular weight polyester polymers can be prepared and used as is, in applications such as clothing and beverage bottles. In this case, stoichiometry of the Product 12 and a carboxylic acid or acid chloride must be nearly 1 to enable high degrees of polymerization.

Composites made from the cured compounds of the invention, and derivatives thereof, can contain additives such as fibers, clays, silicates, fillers, whiskers or other conventional filler or reinforcing materials, including nanomaterials. Typical fibers used for such composites include, but are not limited to, E-glass, S-glass, KEVLAR®, carbon fiber, and ultra-high molecular weight polyethylene. Additional additives can be employed in conventional amounts and can be added directly to the process during formation of the composite. Such additional additives can include, for example, colorants, pigments, carbon black, chopped fibers or particulates of glass, carbon and aramid, fillers, impact modifiers, antioxidants, stabilizers, flame retardants, reheating aids, crystallization aids, oxygen scavengers, plasticizers, flexibilizers, anti-fogging agents, nucleating agents, foaming agents, mold release agents, and any combinations thereof.

The following exemplary embodiments relate to specific compounds shown in FIG. 7, but the methods described herein are applicable to all embodiments of the invention.

The neat (meth)acrylic ester products (Products 3-6) can be treated with a free-radical initiator (for example, cumene hydroperoxide and/or methyl ethyl ketone peroxide) at a concentration of about 0.5-8.0 wt % (in certain embodiments, about 1.0-3.0 wt %) in order to induce curing of the resin to form a novel polymer. Curing of resins can be accomplished with or without a promoter, for example cobalt naphthenate and dimethyl aniline, to accelerate gel time in concentrations of 0.10-1.5 wt % (in certain embodiments, about 0.25-0.5 wt %). Cure temperatures for resins can range from about 20-85° C. ((in certain embodiments, about 25-60° C.) and post-cured at about 100-250° C. (in certain embodiments, about 120-180° C.). In certain embodiments, the materials obtained herein have comparable properties to commercial (meth)acrylic ester derived polymers and exhibit similar stiffness, toughness and $T_g$.

The (meth)acrylated products (Products 3-6) can be blended with reactive diluents (including, but not limited to, styrene, (meth)acrylated lauric acid, and/or furfuryl (meth) acrylate) to produce novel resin systems. Typically the composition is about 30-90% wt % (meth)acrylic ester (Products 3-6) and about 25-50 wt % reactive diluent. In certain embodiments, these resins have low viscosities that would make them ideal for liquid molding, composite layups and vacuum assisted resin transfer molding (VARTM) processing, as well as a wide range of other applications. These resins can be cured using a free-radical initiator, in the presence or absence of a promoter, to produce co-polymers that have properties similar to polymeric materials produced by existing commercial processes, providing equivalent stiffness, toughness and $T_g$.

UPE (Product 7) resin systems can be blended with olefinically unsaturated reactive diluents (including, but not limited to, styrene, (meth)acrylated lauric acid, and/or methyl (meth)acrylate) to produce novel resin systems where the composition is about 30-90 wt % Product 7 and about 10-70 wt % reactive diluent; in certain embodiments, about 50-75 wt % Product 7 and about 25-50 wt % reactive diluent. These resins have demonstrated viscosities amenable to liquid molding, composite layups, VARTM processing as well as a wide range of other applications. The blended Product 7 resin can be treated with a free-radical initiator (for example, cumene hydroperoxide and/or methyl ethyl ketone peroxide) at a concentration of abouty 0.5-8.0 wt % (in certain embodiments, about 1.0-3.0 wt %) in order to induce curing of the resin to form a novel thermoset polymer. Curing of resins can be accomplished with or without a promoter, for example cobalt naphthenate and/or dimethyl aniline, to accelerate gel time preferably in concentrations of about 0.10-1.5 wt % (in certain embodiments, about 0.25-0.75 wt %). Cure temperatures for these UPE resins can range from about 20-85° C., about 25-60° C. and post-cured at about 100-200° C. (in certain embodiments, 120-180° C.).

Alternatively, high molecular weight polyester polymers can be prepared and used as is, in applications such as clothing and beverage bottles. In this case, in certain non-limiting embodiments. stoichiometric ratio of the Product 1 and a carboxylic acid or acid chloride must be nearly 1 to enable high degrees of polymerization.

In certain embodiments, the compounds of the invention can be used as components of a polymerizable composition, which can be polymerized to provide a polymerized material with one or more of the following characteristics: good mechanical performance (evaluated in terms of modulus, toughness, swelling, low wear and/or long durability); good biological performance (evaluated in terms of biocompatibility, non-toxicity, non-degradability, and/or absence of non-biofilm formation); aesthetics and handling characteristics (evaluated in terms of rheological behavior and appearance), good curing characteristics (evaluated in terms of on-demand curing, rapid reaction, and/or successful curing of thick materials), anti-fouling characteristics, anti-inflammatory characteristics, acid-based indicator characteristics to assess the corrosivity of the environment, and others (such as low shrinkage and stress, excellent adhesion to the interface and the like). In other embodiments, use of alkyl aldehydes/ketones within the compositions and methods of the invention reduces the melting point of the polymerized composition, which in certain embodiments is a liquid at about room temperature, and that increases the flexibility and/or toughness of the resulting polymer, and reduces water uptake of the resulting polymer. In yet other embodiments, use of an aromatic or heteroaromatic aldehyde/ketone within the compositions and methods of the invention increases the modulus and glass transition temperature of the resulting polymer. In yet other embodiments, use of a furan aldehyde/ketone within the compositions and methods of the invention enables self-healing through Diels-Alder chemistry. In yet other embodiments, the use of furan amine monomers within the compositions and methods of the invention reduces water permeability and/or oxygen permeability of the resulting polymer. Without wishing to be limited by any theory, use of ketone monomers within the methods of the invention results in greater environmental stability for the product due to the absence of a labile tertiary hydrogen in the product.

The polymerized products of the inventions have one or more of the following characteristics: good mechanical performance (evaluated in terms of modulus, toughness, swelling, low wear and/or long durability); good biological performance (evaluated in terms of biocompatibility, non-toxicity, non-degradability, and/or absence of non-biofilm formation); aesthetics and handling characteristics (evaluated in terms of rheological behavior and appearance), good curing characteristics (evaluated in terms of on-demand curing, rapid reaction, and/or successful curing of thick materials) and others (such as low shrinkage and stress, excellent adhesion to the interface and the like); anti-fouling and anti-inflammatory. In certain embodiments, incorporation of capsaicin within the compounds of the invention enables anti-inflammatory and anti-fouling. In certain embodiments, use of a furan aldehyde/ketone enables self-healing through Diels-Alder chemistry. In certain embodiments, the use of furan amine monomers reduces water permeability and the use of any furan monomers reduces oxygen permeability.

The compounds described herein can form salts with acids or bases, and such salts are included in the present invention. The term "salts" embraces addition salts of free acids or bases that are useful within the methods of the invention.

Suitable acid addition salts can be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids can be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, stearic, alginic, cyclohexylaminosulfonic, β-hydroxybutyric, salicylic, galactaric, galacturonic acid, glycerophosphonic acids and saccharin (e.g., saccharinate, saccharate). Salts can be comprised of a fraction of one, one or more than one molar equivalent of acid or base with respect to any compound of the invention.

Suitable base addition salts of compounds of the invention include, for example, ammonium salts and metallic salts including alkali metal, alkaline earth metal and transition metal salts such as, for example, calcium, magnesium, potassium, sodium and zinc salts. Base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts can be prepared from the corresponding compound by reacting, for example, the appropriate acid or base with the compound.

The compounds of the invention can also exist as solvates, wherein they are associated with solvent molecules. Solvates include water, ether (e.g., tetrahydrofuran, methyl tert-butyl ether) or alcohol (e.g., ethanol) solvates, acetates and the like. In certain embodiments, the compounds described herein exist in solvated forms with solvents such as water, and ethanol. In other embodiments, the compounds described herein exist in unsolvated form.

Methods

In one aspect, the invention provides a method of condensing at least two phenolic- or aniline-containing (aromatic) monomers and an aromatic, aliphatic or heteroaromatic aldehyde/ketone monomer (which can be a mono-aldehyde, mono-ketone, polyaldehyde, poly-ketone, or contain both aldehyde and ketone groups).

In certain embodiments, the method comprises contacting the at least two phenolic- or aniline-containing (aromatic) monomers; the aromatic, aliphatic or heteroaromatic aldehyde/ketone monomer, and an acid catalyst. In other embodiments, the ratio of phenolic- or aniline-containing monomer to the aldehyde/ketone monomer is about 2:1. In yet other embodiments, that ratio is about 5:1 to minimize oligomerization. The phenolic- or aniline-containing (aromatic) monomers are mixed with the aldehyde/ketone monomer and the mixture is then heated to about 60-65° C. for about 2 hours. Then, an acid catalyst is added slowly and the reaction is allowed to progress for about 24 hours. In an exemplary case where a solid acid catalyst is utilized (such as AMBERLYST 15 hydrogen form or DOWEX DR-2030 hydrogen form), the reaction mixture is diluted in an organic solvent, and subsequently filtered to remove the catalyst. The mixture is then concentrated under reduced pressure and purified vie chromatography or any other purification method known in the art.

In another aspect, the invention provides a method of evaluating the pH of a system, wherein the method comprises contacting a compound of Formula (Ie or IIb) with the system and evaluating the ultraviolet visible (UV-vis) spectrum of the compound of Formula (Ie or IIb).

Kits

The invention includes a kit relating to the compositions and methods of the invention. Although exemplary kits are described below, the contents of other useful kits will be apparent to the skilled artisan in light of the present disclosure. Each of these kits is included within the invention. The kits of the present invention are useful, because, as disclosed elsewhere herein, such kits can be used to prepare compounds of the invention and/or to use compounds of the invention in preparing compositions and/or other materials, such as but not limited to polymerizable and/or polymerized materials.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

Unless described otherwise, the materials used in the experiments were obtained from commercial sources or obtained by methods known in the art, and used without further purification.

Example 1

Figure 10:
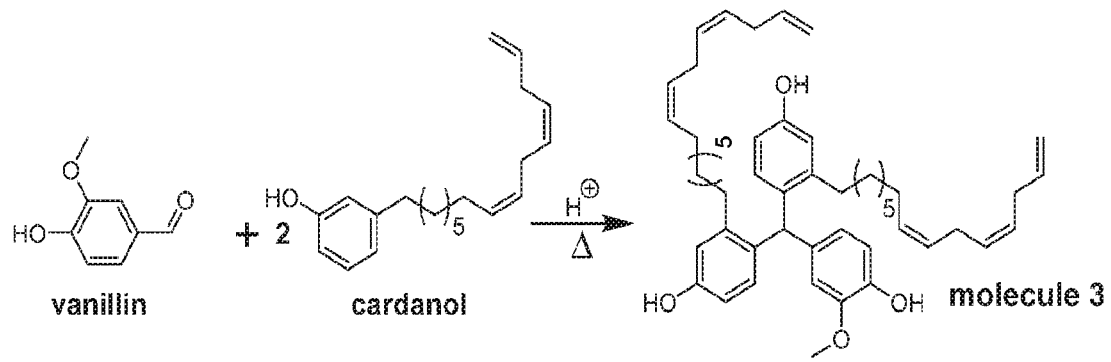
FIG. 10 illustrates a non-limiting synthesis of vanillin-2-cardanol (molecule 3) from vanillin and cardanol.
Figure 11:
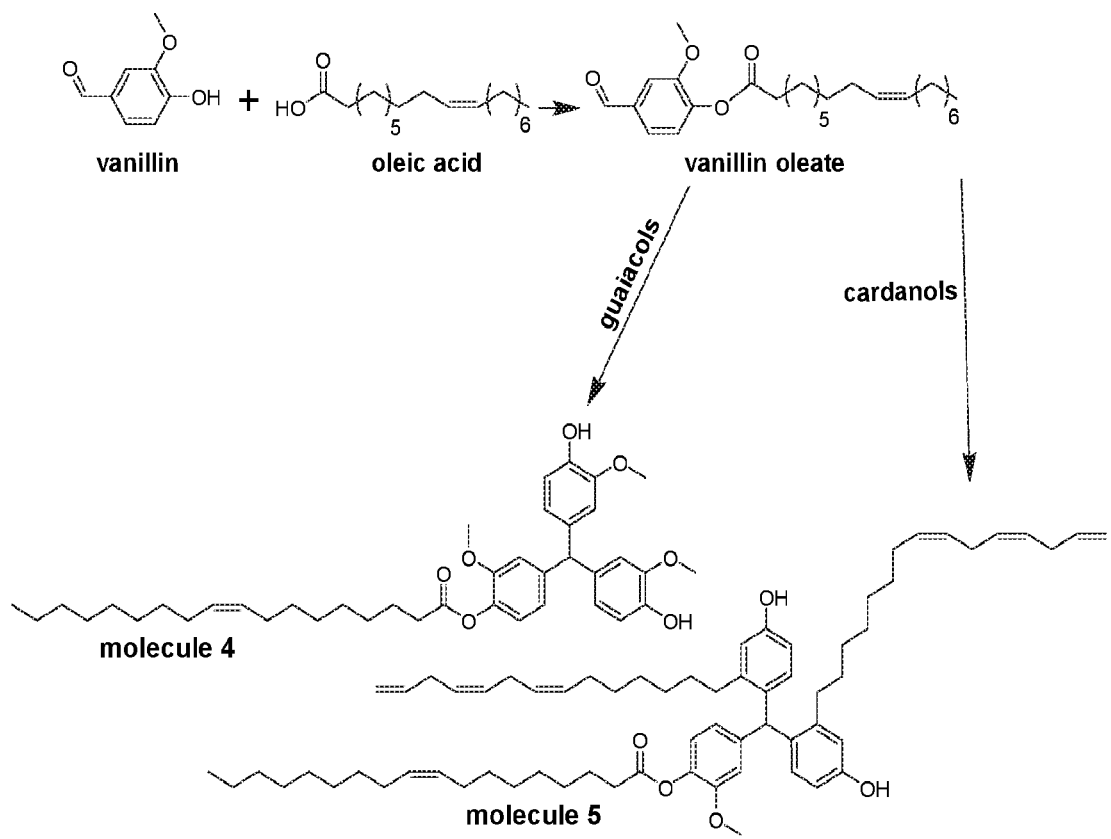
FIG. 11 illustrates a non-limiting syntheses of vanillin oleate-2-guaiacol (molecule 4) and vanillin oleate-2-cardanol (molecule 5) from vanillin, oleic acid, and cardanol.

A 100 mL three-neck round bottom flask equipped with magnetic stir bar was charged with vanillin (1 g, 6.57 mmol) and cardanol (9.8 g, 32.86 mmol), to yield Product 1 of FIG. 10. The mixture was heated to 60° C. for two hours with constant stirring. Next, 1.08 g of Dowex DR-2030 hydrogen form catalyst was added slowly with continuous mixing. The reaction was allowed to continue at 60° C. for approximately 24 hours. The reaction mixture was subsequently removed from heat and allowed to cool to room temperature. The reaction mixture was diluted with dichloromethane, and the catalyst was removed via vacuum filtration. The filtrate was then washed with deionized water, and the organic phase was dried over anhydrous sodium sulfate. The organic phase was then concentrated under reduced pressure and purified via hexanes/ethyl acetate chromatography. The product was characterized by $^1$H-NMR as having high purity.

Example 2

A 250 mL three-neck round bottom flask equipped with magnetic stir bar was charged with vanillin (5 g, 32.86 mmol) and 4-methylcatachol (20.4 g, 164.33 mmol), to yield a related compound of Product 1 from FIG. 7. The mixture was heated to 60° C. for two hours with constant stirring. Next, 2.54 g of Dowex DR-2030 hydrogen form catalyst was added slowly with continuous mixing. The reaction was allowed to continue at 60° C. for approximately 24 hours. The reaction mixture was subsequently removed from heat and allowed to cool to room temperature. The reaction mixture was diluted in dichloromethane, and the catalyst was removed via vacuum filtration. The filtrate was then washed with deionized water, and the organic phase was dried with anhydrous sodium sulfate. The organic phase was then concentrated under reduced pressure and purified via hexanes/ethyl acetate chromatography. The product was characterized by $^1$H-NMR as having high purity.

Example 3

A 100 mL three-neck round bottom flask equipped with magnetic stir bar was charged with p-anisaldehyde (1 g, 7.34 mmol) and guaiacol (4.56 g, 36.73 mmol), to yield a related compound of Product 1 from FIG. 7. The mixture was heated to 60° C. for two hours with constant stirring. Next, 0.56 g of Dowex DR-2030 hydrogen form catalyst was added slowly with continuous mixing. The reaction was allowed to continue at 60° C. for approximately 24 hours. The reaction mixture was subsequently removed from heat and allowed to cool to room temperature. The reaction mixture was diluted in dichloromethane, and the catalyst was removed via vacuum filtration. The filtrate was then washed with deionized water, and the organic phase was dried with anhydrous sodium sulfate. The organic phase was then concentrated under reduced pressure and purified via hexanes/ethyl acetate chromatography. The product was characterized by $^1$H-NMR as having high purity.

Example 4

A 250 mL three-neck round bottom flask equipped with magnetic stir bar was charged with vanillin (10 g, 65.72 mmol) and guaiacol (40.8 g, 328.66 mmol), to yield a related compound of Product 1 from FIG. 7. The mixture was heated to 60° C. for two hours with constant stirring. Next, 5.08 g of Dowex DR-2030 hydrogen form catalyst was added slowly with continuous mixing. The reaction was allowed to continue at 60° C. for approximately 24 hours. The reaction mixture was subsequently removed from heat and allowed to cool to room temperature. The reaction mixture was diluted in dichloromethane, and the catalyst was removed via vacuum filtration. The filtrate was then washed with deionized water, and the organic phase was dried with anhydrous sodium sulfate. The organic phase was then concentrated under reduced pressure and purified via hexanes/ethyl acetate chromatography. The product was characterized by $^1$H-NMR as having high purity.

Example 5

A 250 mL three-neck round bottom flask equipped with magnetic stir bar and dropping funnel was charged with triguaiacol (Example 4) (5 g, 13.08 mmol), triethylamine (3.97 g, 39.23 mmol), and 12 mL of dichloromethane. The reaction flask was sparged with dry argon gas for 30 minutes and placed in an ice bath below 0° C. Methacryloyl chloride (4.31 g, 41.25 mmol) dissolved in 24 mL of dichloromethane was added dropwise using the addition funnel. The reaction mixture was allowed to warm to room temperature overnight, and the organic phase was washed three times each with 2.5 M sodium hydroxide, 1.0 M hydrochloric acid, and deionized water sequentially. The organic phase was then dried over sodium sulfate and concentrated under reduced pressure. The product (Product 4, FIG. 7) was characterized by $^1$H-NMR as having high purity.

Example 6

Triguaiacol (0.25 g, Example 4) was dissolved in 100 mL of deionized water. The mixture was titrated with 0.1 M sodium hydroxide solution. At every 0.5 pH, UV-VIS spectroscopy was performed on a portion of the mixture. The wavelength in the absorbance spectrum where the absorbance is at a maximum was measured. The absorbance wavelength was shown to decrease with increasing pH.

Example 7

A 250 mL round bottom flask equipped with magnetic stir bar was charged with vanillyl alcohol (8 g, 51.89 mmol) and cardanol (46.4 g, 155.67 mmol). The mixture was heated to 60° C. for two hours with constant stirring. Next, 5.30 g of Dowex DR-2030 hydrogen form catalyst were added slowly with continuous mixing. The reaction was allowed to continue at 60° C. for approximately 24 hours. The reaction mixture was subsequently removed from heat and allowed to cool to room temperature. The reaction mixture was diluted with dichloromethane, and the catalyst was removed via vacuum filtration. The filtrate was then washed with deionized water, and the organic phase was dried over anhydrous sodium sulfate. The organic phase was then concentrated under reduced pressure and purified via hexanes/ethyl acetate chromatography. The product (Product 1, FIG. 12) was characterized by $^1$H-NMR as having high purity.

Example 8

A 100 mL round bottom flask equipped with magnetic stir bar was charged with vanillyl alcohol (1 g, 6.48 mmol) and capsaicin (5.94 g, 19.45 mmol). The mixture was heated to 60° C. for two hours with constant stirring. Next, 0.69 g of Dowex DR-2030 hydrogen form catalyst were added slowly with continuous mixing. The reaction was allowed to continue at 60° C. for approximately 24 hours. The reaction mixture was subsequently removed from heat and allowed to cool to room temperature. The reaction mixture was diluted with dichloromethane, and the catalyst was removed via vacuum filtration. The filtrate was then washed with deionized water, and the organic phase was dried over anhydrous sodium sulfate. The organic phase was then concentrated under reduced pressure and purified via hexanes/ethyl acetate chromatography, thus yielding a related compound to Product 1, FIG. 12.

Example 9

A 100 mL round bottom flask equipped with magnetic stir bar was charged with (5-methyl-2-furyl) methanol (1 g, 8.19 mmol) and cardanol (7.33 g, 24.56 mmol). The mixture was heated to 60° C. for two hours with constant stirring. Next, 0.83 g of Dowex DR-2030 hydrogen form catalyst were added slowly with continuous mixing. The reaction was allowed to continue at 60° C. for approximately 24 hours. The reaction mixture was subsequently removed from heat and allowed to cool to room temperature. The reaction mixture was diluted with dichloromethane, and the catalyst was removed via vacuum filtration. The filtrate was then washed with deionized water, and the organic phase was dried over anhydrous sodium sulfate. The organic phase was then concentrated under reduced pressure and purified via hexanes/ethyl acetate chromatography, thus yielding a related compound to Product 1, FIG. 12.

The disclosures of each and every patent, patent application, and publication cited herein are hereby incorporated herein by reference in their entirety.

While the invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A compound of Formula (V), or a salt or solvate thereof:

wherein: P2 $R^1$ and $R^2$ are independently selected from the group consisting of H and $C_1$-$C_{12}$ alkyl, or $R^1$ and $R^2$ combine to form =O;

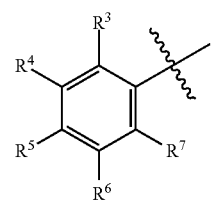

ring A is

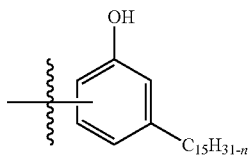

ring B is n is selected from the group consisting of 0, 2, 4, and 6;

each one of $R^3$-$R^7$ is independently selected from the group consisting of H, —OH, hydroxymethyl, $C_1$-$C_{20}$ alkyl, $C_1$-$C_6$ alkoxy, $C_1$-$C_6$ acyloxy, halogen, —$NH_2$, furyl, benzyl, substituted furyl and substituted benzyl, wherein at least one of $R^6$ or $R^7$ is methoxy or $C_1$-$C_6$ acyloxy, and wherein at least one selected from the group consisting of $R^3$-$R^7$ is —OH.

2. The compound of claim 1, wherein ring A is derived from the starting material:

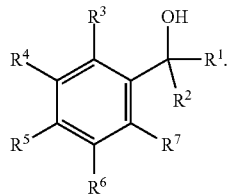

3. The compound of claim 1, wherein at least one applies:
(i) at least one occurrence of $R^3$-$R^7$ is H;
(ii) at least two occurrences of $R^3$-$R^7$ are H;
(iii) at least three occurrences of $R^3$-$R^7$ are H;
(iv) at least four occurrences of $R^3$-$R^7$ are H;
(v) $R^1$ and $R^2$ are H;
(vi) $R^1$ and $R^2$ are methyl;
(vii) $R^1$ is H and $R^2$ is methyl;
(viii) $R^1$ and $R^2$ combine so as to form =O.

4. The compound of claim 1, wherein at least one applies:
(a) at least one phenolic or aniline group is derivatized with an epoxy group;
(b) at least one phenolic or aniline group is derivatized with a (meth)acrylate or (meth)acrylic group;
(c) at least one phenolic hydroxyl group or aniline amino group forms a urethane group;
(d) at least one phenolic hydroxyl group forms a carbonate group;
(e) at least one phenolic hydroxyl group forms an allyl ester, or wherein at least one aniline amine forms an allyl amide.

5. The compound of claim 4, wherein the compound is cured into a polymer.

6. A method of preparing the compound of claim 1, wherein the method comprises contacting:

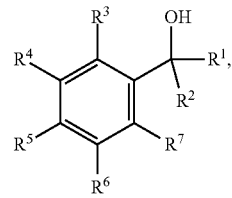

wherein at least one selected from the group consisted of $R^3$-$R^7$ is –OH, cardanol, or any salt, solvate or derivative thereof; and an acid catalyst; or (b) wherein the method comprises contacting:

at least two compounds independently selected from the group consisting of cardanol and cardol, or any salt, solvate or derivative thereof;

at least one selected from the group consisting of any aldehyde and ketone; and an acid catalyst.

7. The method of claim 6, wherein at least one starting material is independently isolated from a bio-based resource.

* * * * *